US007198928B2

(12) United States Patent
Liang et al.

(10) Patent No.: US 7,198,928 B2
(45) Date of Patent: Apr. 3, 2007

(54) HUMAN COX-1 ALTERNATIVELY SPLICED VARIANTS AND METHODS OF USING SAME

(75) Inventors: Yanbin Liang, Irvine, CA (US); David F. Woodward, Lake Forest, CA (US)

(73) Assignee: Allergan, Inc., Irvine, CA (US)

( * ) Notice: Subject to any disclaimer, the term of this patent is extended or adjusted under 35 U.S.C. 154(b) by 450 days.

(21) Appl. No.: 10/663,377

(22) Filed: Sep. 15, 2003

(65) Prior Publication Data

US 2005/0233429 A1    Oct. 20, 2005

(51) Int. Cl.
*C12N 9/02* (2006.01)
*C12N 1/20* (2006.01)
*C12N 15/70* (2006.01)
*C12P 21/06* (2006.01)
*C07H 21/04* (2006.01)

(52) U.S. Cl. .................. 435/189; 435/69.1; 435/252.3; 435/320.1; 536/23.2

(58) Field of Classification Search ................ 435/189, 435/69.1, 252.3, 320.1; 536/23.2
See application file for complete search history.

(56) References Cited

U.S. PATENT DOCUMENTS

2004/0172684 A1* 9/2004 Kovalic et al. ............. 800/284

OTHER PUBLICATIONS

Carelli et al., "Optic nerve degeneration and mitochondrial dysfunction: Genetic and acquired optic neuropathies," *Neurochem. Int.* 40:573-584 (2002).
Chandrasekharan et al., "COX-3, a cyclooxygenase-1 variant inhibited by acetaminophen and other analgesic/antipyretic drugs: Cloning, structure, and expression," *Proc. Natl. Acad. Sci USA* 99:13926-13931 (2002).
"Chemiluminescent Cyclooxygenase Activity Kit: Catalog No. 907-003," Assay Designs, Inc. 1-12.
"Cox Activity Assay: Catalog No. 760151," Cayman Chemical 1-8.
"Cox (human) inhibitor screening assay: Catalog No. CM51061," IBL Immuno-Biological Laboratories 1-8.
Crofford, "COX-1 and COX-2 tissue expression: Implications and predictions," *J. Rheumatol.* 24:15-19 (1997).
"Cyclooxygenase Activity Kit: Catalog No. EKS-320" Stressgen Biotechnologies 1-10.
Dewitt and Smith, "Primary structure of prostaglandin G/H synthase from sheep vesicular gland determined from the complementary DNA sequence," *Proc. Natl. Acad. Sci. USA* 85:1412-1416 (1988).
Dewitt et al., "The aspirin and heme-binding sites of ovine and murine prostaglandin endoperoxide synthases," *J. Biol. Chem.* 265:5192-5198 (1990).
Diaz et al., "Alternative splicing of human prostaglandin G/H synthase mRNA and evidence of differential regulation of the resulting transcripts by transforming growth factor beta 1, interleukin 1 beta, and tumor necrosis factor alpha," *J. Biol. Chem* 267:10816-10822 (1992).

Droge et al., Alternative Splicing of Cyclooxygenase-1 mRNA in the Human Iris, *Ophthalmic. Res.* 35:160-163 (2003).
Dubois et al., "Cyclooxygenase in biology and disease," *FASEB Journal* 12:1063-1073 (1998).
Escribano et al., "cDNA from human ocular ciliary epithelium homologous to beta ig-h3 is preferentially expressed as an extracellular protein in the corneal epithelium," *J. Cell Physiol.* 160:511-521 (1994).
Feng et al., "Cloning two isoforms of rat cyclooxygenase: Differential regulation of their expression," *Arch. Biochem. Biophys.* 307:361-368 (1993).
FitzGerald et al., "COX-2 inhibitors and the cardiovascular system," *Clin. Exp. Rheumatol.* 19:S31-S36 (2001).
Funk et al., "Human platelet/erythroleukemia cell prostaglandin G/H synthase: cDNA cloning, expression, and gene chromosomal assignment," *FASEB J.* 5:2304-2312 (1991).
Gierse et al, "A single amino acid difference between cyclooxygenase-1 (COX-1) and -2 (COX-2) reverses the selectivity of COX-2 specific inhibitors," *J. Biol. Chem.* 271:15810-15814 (1996).
Hennan et al., "Effects of selective cyclooxygenase-2 inhibition on vascular responses and thrombosis in canine coronary arteries," *Circulation* 104:820-825 (2001).
Hla, "Molecular characterization of the 5.2 KB isoform of the human cyclooxygenase-1 transcript," *Prostaglandins* 51:81-85 (1996).
Jones, "Practical COX-1 and COX-2 pharmacology: What's it all about?" 1-5. www.vetmedpub.com/cp/pdf/symposium/nov__1.pdf.
Kitzler et al., "Analysis and quantitation of splicing variants of the TPA-inducible PGHS-1 mRNA in rat tracheal epithelial cells," *Arch. Biochem. Biophys.* 316:856-863 (1995).
Marnett et al., "Arachidonic acid oxygenation by COX-1 and COX-2: Mechanisms of catalysis and inhibition," *J. Biol. Chem.* 274:22903-22906 (1999).
Marnett et al., "Mechanism of the stimulation of prostaglandin H synthase and prostacyclin synthase by the antithrombotic and antimetastatic agent, nafazatrom," *Mol. Pharmacol.* 26:328-335 (1984).

(Continued)

*Primary Examiner*—Manjunath N. Rao
*Assistant Examiner*—Iqbal Chowdhury
(74) *Attorney, Agent, or Firm*—Joel B. German; Dean G. Stathakis; Martin A. Voet

(57) ABSTRACT

The invention provides an isolated polypeptide containing the amino acid sequence of SEQ ID NO: 14, 16, 18, 20, 22 or 24. The invention also provides an isolated polypeptide containing a) an amino acid sequence having at least 50% amino acid identity with SEQ ID NO: 10, and b) an amino acid sequence selected from SEQ ID NOS: 14, 16, 18, 20, 22, or 24; or a conservative variant thereof. The invention further provides an isolated polypeptide containing the amino acid sequence of SEQ ID NO: 2, 4, 6, or 8. The invention also provides a method for identifying a compound that modulates a COX-1 variant by contacting an isolated COX-1 variant or a COX-1 variant over-expressed in a genetically engineered cell with a compound and determining the level of an indicator which correlates with modulation of a COX-1 variant, where an alteration in the level of the indicator as compared to a control level indicates that the compound is a compound that modulates the COX-1 variant.

3 Claims, 10 Drawing Sheets

OTHER PUBLICATIONS

Matsuo and Cynader, "The EP2 receptor is the predominant prostanoid receptor in the human ciliary muscle," *Br. J. Ophthalmol.* 77:110-114 (1993).

Merlie et al., "Isolation and characterization of the complementary DNA for sheep seminal vesical prostaglandin endoperoxide synthase (cyclooxygenase)," *J. Biol. Chem.* 263:3550-3553 (1988).

Neddleman et al., "Arachidonic acid metabolism," *Annu. Rev. Biochem.* 55:69-102 (1986).

Olichon et al., "Loss of OPA1 perturbates the mitochondrial inner membrane structure and integrity, leading to cytochrome c release and apoptosis," *J. Biol. Chem.* 278:7743-7746 (2003).

Palmer and Henrich, "Clinical acute renal failure with nonsteroidal anti-inflammatory drugs," *Semin. Nephrol.* 15:214-227 (1995).

Rowlinson et al., "The binding of arachidonic acid in the cyclooxygenase active site of mouse prostaglandin endoperoxide synthase-2 (COX-2). A putative L-shaped binding conformation utilizing the top channel region," *J. Biol. Chem.* 274:23305-23310 (1999).

Schafer, "Effects of nonsteroidal anti-inflammatory drugs on platelet function and systemic hemostasis," *J. Clin. Pharmacol.* 35:209-219 (1995).

Scott et al., "Characterization of the human prostaglandin H synthase 1 gene (PTGS1): Exclusion by genetic linkage analysis as a second modifier gene in familial thrombosis," *Blood Coagulation and Fibrinolysis* 13:519-531 (2002).

Silverstein et al., "Gastrointestinal toxicity with celecoxib vs. nonsteroidal anti-inflammatory drugs for osteoarthritis and rheumatoid arthritis: The Class Study: A randomized controlled trial," *JAMA* 284:1247-1255 (2000).

Trevethick et al., "Non-steroid anti-inflammatory drug-induced gastric damage in experimental animals: Underlying pathological mechanisms," *Gen. Pharmacol.* 26:1455-1459 (1995).

Van Haeringen et al., "Constitutive cyclooxygenase-1 and induced cyclooxygenase-2 in isolated human iris inhibited by S(+) flurbiprofen," *J. Ocul. Pharmacol. Ther.* 16:353-361 (2000).

Vogiagis et al., "Cyclooxygenase-1 and an alternatively spliced mRNA in the rat stomach: Effects of aging and ulcers," *Am. J. Physiol. Gastrointest. Liver Physiol.* 278:G820-G827 (2000).

Vogiagis et al., "Rat colorectal tumours treated with a range of non-steroidal anti-imflammatory drugs show altered cyclooxygenase-2 and cyclooxygenase-1 splice variant mRNA expression levels," *Carcinogenesis* 22:869-874 (2001).

Wallace, "Nonsteroidal anti-inflammatory drugs and gastroenteropathy: The second hundred years," *Gastroenterology* 112:1000-1016 (1997).

Wentzel et al., "Transcription of prostanoid receptor genes and cyclooxygenase enzyme genes in cultivated human iridial melanocytes from eyes of different colours," *Pigment Cell Res.* 16:43-49 (2003).

Xie et al., "Expression of a mitogen-responsive gene encoding prostaglandin synthase is regulated by mRNA splicing," *Proc. Natl. Acad. Sci. USA* 88: 2692-2696 (1991).

Yokoyama and Tanabe, "Cloning of human gene encoding prostaglandin endoperoxide synthase and primary structure of the enzyme," *Biochem. Biophys. Res. Commun.* 165:888-894 (1989).

Zambraski, The effects of nonsteroidal anti-inflammatory drugs on renal function: Experimental studies in animals,*Semin. Nephrol.* 15:205-213 (1995).

Genbank Accession No. AF440204, homo sapiens prostaglandin-endoperoxide synthase 1 (PTGS1) gene, exons 1 through 11 and complete cds.

Genbank Accession No. AF535138, canis familiaris cyclooxygenase mRNA, complete cds.

Genbank Accession No. NM_000962, homo sapiens prostaglandin-endoperoxide synthase 1 (prostaglandin G/H synthase and cyclooxygenase) (PTGS1), transcript variant 1, mRNA.

Genbank Accession No. NM_000963, homo sapiens prostaglandin-endoperoxide synthase 2 (prostaglandin G/H synthase and cyclooxygenase) (PTGS2), mRNA.

Genbank Accession No. NM_080591, homo sapiens prostaglandin-endoperoxide synthase 1 (prostaglandin G/H synthase and cyclooxygenase) (PTGS1), transcript variant 2, mRNA.

Genbank Accession No. NT_017568.11, homo sapiens chromosome 9 genomic contig.

* cited by examiner

Human COX-1 Variant ALT-1

```
atgagccgga gtctcttgct ccggttcttg ctgttcctgc tcctgctccc gccgctccc  60
gtcctgctcg cggacccagg ggcgcccacg ccagggcct ctttgggagg aagccgcagg  120
caccaaggga aatgagttcc ctttctccag cctctaaccg tctgggaacc catcctgatt  180
cccattgcca gtggagaagg tctccctgg tgaagacttc gggagaacat gggagatgga  240
aatacattta ggagccggga tgcttcatct ggggtttaag agatccccat tgagcaaATG  300
aggaaaccga ggctcatgaa tccctgttgt tactatccat gccagcacca gggcatctgt  360
gtccgcttcg gccttgaccg ctaccagtgt gactgcaccc gcacgggcta ttccggcccc  420
aactgcacca tccctggcct gtggacctgg ctccggaatt cactgcggcc cagcccctct  480
ttcacccact tcctgctcac tcacgggcgc tggttctggg agtttgtcaa tgccaccttc  540
atccgagaga tgctcatgcg cctggtactc acagtgcgct ccaaccttat ccccagtccc  600
cccacctaca actcagcaca tgactacatc agctgggagt ctttctccaa cgtgagctat  660
tacactcgta ttctgccctc tgtgcctaaa gattgcccca cacccatggg aaccaaaggg  720
aagaagcagt gccagatgc ccagctcctg gcccgccgct tcctgctcag gaggaagttc  780
atacctgacc cccaaggcac caacctcatg tttgccttct tgcacaaca cttcacccac  840
cagttcttca aaacttctgg caagatgggt cctggcttca ccaaggcctt gggccatggg  900
gtagacctcg ccacatttta tggagacaat ctggagcgtc agtatcaact gcggctcttt  960
aaggatggga aactcaagta ccaggtgctg gatggagaaa tgtacccgcc ctcggtagaa  1020
gaggcgcctg tgttgatgca ctaccccga ggcatcccgc cccagagcca gatggctgtg  1080
ggccaggagg tgtttgggct gcttcctggg ctcatgctgt atgccacgct ctggctacgt  1140
gagcacaacc gtgtgtgtga cctgctgaag gctgagcacc ccacctgggg cgatgagcag  1200
cttttccaga cgacccgcct catcctcata ggggagacca tcaagattgt catcgaggag  1260
tacgtgcagc agctgagtgg ctatttcctg cagctgaaat tgacccaga gctgctgttc  1320
ggtgtccagt ccaataccg caaccgcatt gccatggagt tcaaccatct ctaccactgg  1380
caccccctca tgcctgactc cttcaaggtg gctcccagg agtacagcta cgagcagttc  1440
ttgttcaaca cctccatgtt ggtggactat ggggttgagg ccctggtgga tgccttctct  1500
cgccagattg ctggccggat cggtgggggc aggaacatgg accaccacat cctgcatgtg  1560
gctgtggatg tcatcaggga gtctcgggag atgcggctgc agcccttcaa tgagtaccgc  1620
aagaggtttg gcatgaaacc ctacacctcc ttccaggagc tcgtaggaga aaggagatg  1680
gcagcagagt tggaggaatt gtatggagac attgatgcgt ggagttcta ccctggactg  1740
cttcttgaaa agtgccatcc aaactctatc tttggggaga gtatgataga gattggggct  1800
ccctttttcc tcaagggtct cctagggaat ccatctgtt ctccggagta ctggaagccg  1860
agcacatttg gcggcgaggt gggctttaac attgtcaaga cggccacact gaagaagctg  1920
gtctgcctca acaccaagac ctgtccctac gtttccttcc gtgtgccgga tgccagtcag  1980
gatgatgggc ctgctgtgga gcgaccatcc acagagctcT GA
```

FIGURE 2

Human COX-1 Variant ALT-2

```
atgagccgga gtctcttgct ccggttcttg ctgttcctgc tcctgctccc gccgctcccc  60
gtcctgctcg cggacccagg ggcgcccacg ccaggggcct ctttgggagg aagccgcagg 120
caccaaggga aatgagttcc ctttctccag cctctaaccg tctgggaacc catcctgatt 180
cccattgcca gtggagaagg tctcccctgg tgaagacttc gggagaacat gggagatgga 240
aatacattta ggagccggga tgcttcatct ggggtttaag agatccccat tgagcaaATG 300
aggaaaccga ggctcaggaa gaagcagttg ccagatgccc agctcctggc ccgccgcttc 360
ctgctcagga ggaagttcat acctgacccc caaggcacca acctcatgtt tgccttcttt 420
gcacaacact tcacccacca gttcttcaaa acttctggca agatgggtcc tggcttcacc 480
aaggccttgg ccatggggt agacctcggc cacatttatg gagacaatct ggagcgtcag 540
tatcaactgc ggctctttaa ggatgggaaa ctcaagtacc aggtgctgga tgagaaatg 600
tacccgccct cggtagaaga ggcgcctgtg ttgatgcact accccgagg catcccgccc 660
cagagccaga tggctgtggg ccaggaggtg tttgggctgc ttcctgggct catgctgtat 720
gccacgctct ggctacgtga gcacaaccgt gtgtgtgacc tgctgaaggc tgagcacccc 780
acctggggcg atgagcagct tttccagacg acccgcctca tcctcatagg ggagaccatc 840
aagattgtca tcgaggagta cgtgcagcag ctgagtggct atttcctgca gctgaaattt 900
gacccagagc tgctgttcgg tgtccagttc caataccgca accgcattgc catggagttc 960
aaccatctct accactggca cccctcatg cctgactcct tcaaggtggg ctcccaggag 1020
tacagctacg agcagttctt gttcaacacc tccatgttgg tggactatgg ggttgaggcc 1080
ctggtggatg ccttctctcg ccagattgct ggccggatcg gtggggcag gaacatggac 1140
caccacatcc tgcatgtggc tgtggatgtc atcagggagt ctcgggagat gcggctgcag 1200
cccttcaatg agtaccgcaa gaggtttggc atgaaaccct acacctcctt ccaggagctc 1260
gtaggagaga aggagatggc agcagagttg gaggaattgt atggagacat tgatgcgttg 1320
gagttctacc ctggactgct tcttgaaaag tgccatccaa actctatctt tggggagagt 1380
atgatagaga ttggggctcc cttttccctc aagggtctcc tagggaatcc catctgttct 1440
ccggagtact ggaagccgag cacatttggc ggcgaggtgg ctttaacat tgtcaagacg 1500
gccacactga agaagctggt ctgcctcaac accaagacct gtccctacgt ttccttccgt 1560
gtgccggatg ccagtcagga tgatgggcct gctgtggagc gaccatccac agagctcTGA 1620
ggggcaggaa agcagcattc tggaggggag agctttgtgc ttgtcattcc agagtgctga 1680
ggccagggct gatggtctta aatgctcatt ttctggtttg gcatggtgag tgttggggtt 1740
gacatttaga actttaagtc tcacccatta tctggaatat tgtgattctg tttattcttc 1800
cagaatgctg aactcctt                                               1818
```

FIGURE 3

Human COX-1 Variant ALT-3

```
atgagccgga gtctcttgct ccggttcttg ctgttcctgc tcctgctccc gccgctcccc  60
gtcctgctcg cggacccagg ggcgcccacg ccaggggcct ctttgggagg aagccgcagg  120
caccaaggga aatgagttcc ctttctccag cctctaaccg tctgggaacc catcctgatt  180
cccattgcca gtggagaagg tctcccctgg tgaagacttc gggagaacat gggagatgga  240
aatacattta ggagccggga tgcttcatct ggggtttaag agatccccat tgagcaaATG  300
aggaaaccga ggctcatgaa tccctgttgt tactatccat gccagcacca gggcatctgt  360
gtccgcttcg gccttgaccg ctaccagtgt gactgcaccc gcacgggcta ttccggcccc  420
aactgcacca tccctggcct gtggacctgg ctccggaatt cactgcggcc cagcccctct  480
ttcacccact tcctgctcac tcacgggcgc tggttctggg agtttgtcaa tgccaccttc  540
atccgagaga tgctcatgcg cctggtactc acagtgcgct ccaaccttat ccccagtccc  600
cccacctaca actcagcaca tgactacatc agctgggagt ctttctccaa cgtgagctat  660
tacactcgta ttctgccctc tgtgcctaaa gattgcccca cacccatggg aaccaaaggg  720
aagaagcagt gccagatgc ccagctcctg cccgccgct tcctgctcag gaggaagttc  780
atacctgacc cccaaggcac caacctcatg tttgccttct ttgcacaaca cttcacccac  840
cagttcttca aaacttctgg caagatgggt cctggcttca ccaaggcctt gggccatggg  900
gtagacctcg ccacattta tggagacaat ctggagcgtc agtatcaact gcggctcttt  960
aaggatggga aactcaagta ccaggtgctg atggagaaa tgtacccgcc ctcggtagaa  1020
gaggcgcctg tgttgatgca ctaccccga ggcatcccgc cccagagcca gatggctgtg  1080
ggccaggagg tgtttgggct gcttcctggg ctcatgctgt atgccacgct ctggctacgt  1140
gagcacaacc gtgtgtgtga cctgctgaag gctgagcacc ccacctgggg cgatgagcag  1200
cttttccaga cgacccgcct catcctcata ggggagacca tcaagattgt catcgaggag  1260
tacgtgcagc agctgagtgg ctatttcctg cagctgaaat ttgacccaga gctgctgttc  1320
ggtgtccagt tccaataccg caaccgcatt gccatggagt tcaaccatct ctaccactgg  1380
caccccctca tgcctgactc cttcaagatc ggtgggggca ggaacatgga ccaccacatc  1440
ctgcatgtgg ctgtggatgt catcagggag tctcgggaga tgcggctgca gcccttcaat  1500
gagtaccgca agaggtttgg catgaaaccc tacacctcct ccaggagct cgtaggagag  1560
aaggagatgg cagcagagtt ggaggaattg tatggagaca ttgatgcgtt ggagttctac  1620
cctggactgc ttcttgaaaa gtgccatcca aactctatct tggggagag tatgatagag  1680
attggggctc cctttttccct caagggtctc ctagggaatc ccatctgttc tccggagtac  1740
tggaagccga gcacatttgg cggcgaggtg ggctttaaca ttgtcaagac ggccacactg  1800
aagaagctgg tctgcctcaa caccaagacc tgtccctacg ttccttccg tgtgccggat  1860
gccagtcagg atgatgggcc tgctgtggag cgaccatcca cagagctcTG Aggggcagga  1920
aagcagcatt ctggaggga gagctttgtg cttgtcattc cagagtgctg aggccagggc  1980
tgatggtctt aaatgctcat tttctggttt ggcatggtga gtgttggggt tgacatttag  2040
aactttaagt ctcacccatt atctggaata ttgtgattct gtttattctt ccagaatgct  2100
gaactcctt                                                          2109
```

FIGURE 4

Human COX-1 Variant ALT-4

```
atgagccgga gtctcttgct ccggttcttg ctgttcctgc tcctgctccc gccgctcccc  60
gtcctgctcg cggacccagg ggcgcccacg ccaggggcct ctttgggagg aagccgcagg 120
caccaaggga aatgagttcc ctttctccag cctctaaccg tctgggaacc catcctgatt 180
cccattgcca gtggagaagg tctcccctgg tgaagacttc gggagaacat gggagatgga 240
aatacattta ggagccggga tgcttcatct ggggtttaag agatccccat tgagcaaATG 300
aggaaaccga ggctcagtag gtgccatgat tccccaagct cacaaaatac atggtgggcc 350
caggatctga actcagtgaa tccctgttgt tactatccat gccagcacca gggcatctgt 360
gtccgcttcg gccttgaccg ctaccagtgt gactgcaccc gcacgggcta ttccggcccc 420
aactgcacca tccctggcct gtggacctgg ctccggaatt cactgcggcc cagcccctct 480
ttcacccact tcctgctcac tcacgggcgc tggttctggg agtttgtcaa tgccaccttc 540
atccgagaga tgctcatgcg cctggtactc acagtgcgct ccaaccttat ccccagtccc 600
cccacctaca actcagcaca tgactacatc agctgggagt ctttctccaa cgtgagctat 660
tacactcgta ttctgccctc tgtgcctaaa gattgcccca cccatgggaa ccaaaggg   720
aagaagcagt gccagatgc ccagctcctg gcccgccgct cctgctcag gaggaagttc   780
atacctgacc cccaaggcac caacctcatg tttgccttct ttgcacaaca cttcacccac 840
cagttcttca aaacttctgg caagatgggt cctggcttca ccaaggcctt gggccatggg 900
gtagacctcg ccacatttta tggagacaat ctggagcgtc agtatcaact gcggctcttt 960
aaggatggga aactcaagta ccaggtgctg gatggagaaa tgtacccgcc ctcggtagaa 1020
gaggcgcctg tgttgatgca ctaccccga ggcatcccgc cccagagcca gatggctgtg 1080
ggccaggagg tgtttgggct gcttcctggg ctcatgctgt atgccacgct ctggctacgt 1140
gagcacaacc gtgtgtgtga cctgctgaag gctgagcacc ccacctgggg cgatgagcag 1200
cttttccaga cgacccgcct catcctcata ggggagacca tcaagattgt catcgaggag 1260
tacgtgcagc agctgagtgg ctatttcctg cagctgaaat tgacccaga gctgctgttc 1320
ggtgtccagt ccaataccg caaccgcatt gccatggagt tcaaccatct ctaccactgg 1380
cacccctca tgcctgactc cttcaaggtg gctcccagg agtacagcta cgagcagttc 1440
ttgttcaaca cctccatgtt ggtggactat ggggttgagg ccctggtgga tgccttctct 1500
cgccagattg ctggccggat cggtgggggc aggaacatgg accaccacat cctgcatgtg 1560
gctgtggatg tcatcaggga gtctcgggag atgcggctgc agcccttcaa tgagtaccgc 1620
aagaggtttg gcatgaaacc ctacacctcc ttccaggagc tcgtaggaga aaggagatg  1680
gcagcagagt tggaggaatt gtatggagac attgatgcgt tggagttcta ccctggactg 1740
cttcttgaaa agtgccatcc aaactctatc tttggggaga gtatgataga gattggggct 1800
cccttttccc tcaagggtct cctagggaat cccatctgtt ctccggagta ctggaagccg 1860
agcacatttg gcggcgaggt gggctttaac attgtcaaga cggccacact gaagaagctg 1920
gtctgcctca acaccaagac tgtccctac gttccttcc gtgtgccgga tgccagtcag 1980
gatgatggc ctgctgtgga gcgaccatcc acagagctcT GAgggcagg aaagcagcat 2040
tctggagggg agctttgt gcttgtcatt ccagagtgct gaggccaggg ctgatggtct 2100
taaatgctca ttttctggtt tggcatggt agtgttgggg ttgacattta gaactttaag 2160
tctcacccat tatctggaat attgtgattc tgtttattct tccagaatgc tgaactcctt 2220
```

FIGURE 5

```
COX-1 WT    MSRSLLLRFL LFLLLLPPLP VLLADPGAPT PVNPCCYYPC QHQGICVRFG LDRYQCDCTR TGYSGPNCTI PGLWTWLRNS LRPSPSFTHF
COX-1 ALT-1                                 MRKPR LMNPCCYYPC QHQGICVRFG LDRYQCDCTR TGYSGPNCTI PGLWTWLRNS LRPSPSFTHF
COX-1 ALT-2                           MRKPR LMMPCCYYPC QHQGICVRFG LDRYQCDCTR TGYSGPNCTI PGLWTWLRNS LRPSPSFTHF
COX-1 ALT-3 MRKPR LSRCHDSPSS QNTWAQDLN SVNPCCYYPC QHQGICVRFG LDRYQCDCTR TGYSGPNCTI PGLWTWLRNS LRPSPSFTHF
COX-1 ALT-4

COX-1 WT    LLTHGRWFWE FVNATFIREM LMRLVLTVRS NLIPSPPTYN SAHDYISWES FSNVSYYTRI LPSVPKDCPT PMGTKGKKQL PDAQLLARRF
COX-1 ALT-1 LLTHGRWFWE FVNATFIREM LMRLVLTVRS NLIPSPPTYN SAHDYISWES FSNVSYYTRI LPSVPKDCPT PMGTKGKKQL PDAQLLARRF
COX-1 ALT-2                                                                                    M RKPRLRKKQL PDAQLLARRF
COX-1 ALT-3 LLTHGRWFWE FVNATFIREM LMRLVLTVRS NLIPSPPTYN SAHDYISWES FSNVSYYTRI LPSVPKDCPT PMGTKGKKQL PDAQLLARRF
COX-1 ALT-4 LLTHGRWFWE FVNATFIREM LMRLVLTVRS NLIPSPPTYN SAHDYISWES FSNVSYYTRI LPSVPKDCPT PMGTKGKKQL PDAQLLARRF

COX-1 WT    LLRRKFIPDP QGTNLMFAFF AQHFTHQFFK TSGKMGPGFT KALGHGVDLG HIYGDNLERQ YQLRLFKDGK LKYQVLDGEM YPPSVEEAPV
COX-1 ALT-1 LLRRKFIPDP QGTNLMFAFF AQHFTHQFFK TSGKMGPGFT KALGHGVDLG HIYGDNLERQ YQLRLFKDGK LKYQVLDGEM YPPSVEEAPV
COX-1 ALT-2 LLRRKFIPDP QGTNLMFAFF AQHFTHQFFK TSGKMGPGFT KALGHGVDLG HIYGDNLERQ YQLRLFKDGK LKYQVLDGEM YPPSVEEAPV
COX-1 ALT-3 LLRRKFIPDP QGTNLMFAFF AQHFTHQFFK TSGKMGPGFT KALGHGVDLG HIYGDNLERQ YQLRLFKDGK LKYQVLDGEM YPPSVEEAPV
COX-1 ALT-4 LLRRKFIPDP QGTNLMFAFF AQHFTHQFFK TSGKMGPGFT KALGHGVDLG HIYGDNLERQ YQLRLFKDGK LKYQVLDGEM YPPSVEEAPV

COX-1 WT    LMHYPRGIPP QSQMAVGQEV FGLLPGLMLY ATLWLREHNR VCDLLKAEHP TWGDEQLFQT TRLLLIGETI KIVIEEYVQQ LSGYFLQLKF
COX-1 ALT-1 LMHYPRGIPP QSQMAVGQEV FGLLPGLMLY ATLWLREHNR VCDLLKAEHP TWGDEQLFQT TRLLLIGETI KIVIEEYVQQ LSGYFLQLKF
COX-1 ALT-2 LMHYPRGIPP QSQMAVGQEV FGLLPGLMLY ATLWLREHNR VCDLLKAEHP TWGDEQLFQT TRLLLIGETI KIVIEEYVQQ LSGYFLQLKF
COX-1 ALT-3 LMHYPRGIPP QSQMAVGQEV FGLLPGLMLY ATLWLREHNR VCDLLKAEHP TWGDEQLFQT TRLLLIGETI KIVIEEYVQQ LSGYFLQLKF
COX-1 ALT-4 LMHYPRGIPP QSQMAVGQEV FGLLPGLMLY ATLWLREHNR VCDLLKAEHP TWGDEQLFQT TRLLLIGETI KIVIEEYVQQ LSGYFLQLKF

COX-1 WT    DPELLFGVQF QYRNRIAMEF NHLYHWHPLM PDSFKVGSQE YSYEQFLFNT SMLVDYGVEA LVDAFSRQIA GRIGGGRNMD HHILHVAVDV
COX-1 ALT-1 DPELLFGVQF QYRNRIAMEF NHLYHWHPLM PDSFKVGSQE YSYEQFLFNT SMLVDYGVEA LVDAFSRQIA GRIGGGRNMD HHILHVAVDV
COX-1 ALT-2 DPELLFGVQF QYRNRIAMEF NHLYHWHPLM PDSFKVGSQE YSYEQFLFNT SMLVDYGVEA LVDAFSRQIA GRIGGGRNMD HHILHVAVDV
COX-1 ALT-3 DPELLFGVQF QYRNRIAMEF NHLYHWHPLM PDSFK----- ---------- ---------- ---------- --IGGGRNMD HHILHVAVDV
COX-1 ALT-4 DPELLFGVQF QYRNRIAMEF NHLYHWHPLM PDSFKVGSQE YSYEQFLFNT SMLVDYGVEA LVDAFSRQIA GRIGGGRNMD HHILHVAVDV

COX-1 WT    IRESREMRLQ PFNEYRKRFG MKPYTSFQEL VGEKEMAAEL EELYGDIDAL EFYPGLLLEK CHPNSIFGES MEIGAPFSL KGLLGNPICS
COX-1 ALT-1 IRESREMRLQ PFNEYRKRFG MKPYTSFQEL VGEKEMAAEL EELYGDIDAL EFYPGLLLEK CHPNSIFGES MEIGAPFSL KGLLGNPICS
COX-1 ALT-2 IRESREMRLQ PFNEYRKRFG MKPYTSFQEL VGEKEMAAEL EELYGDIDAL EFYPGLLLEK CHPNSIFGES MEIGAPFSL KGLLGNPICS
COX-1 ALT-3 IRESREMRLQ PFNEYRKRFG MKPYTSFQEL VGEKEMAAEL EELYGDIDAL EFYPGLLLEK CHPNSIFGES MEIGAPFSL KGLLGNPICS
COX-1 ALT-4 IRESREMRLQ PFNEYRKRFG MKPYTSFQEL VGEKEMAAEL EELYGDIDAL EFYPGLLLEK CHPNSIFGES MEIGAPFSL KGLLGNPICS

COX-1 WT    PEYWKPSTFG GEVGFNIVKT ATLKKLVCLN TKTCPYVSFR VPDASQDDGP AVERPSTEL         (SEQ ID NO: 10)
COX-1 ALT-1 PEYWKPSTFG GEVGFNIVKT ATLKKLVCLN TKTCPYVSFR VPDASQDDGP AVERPSTEL         (SEQ ID NO: 2)
COX-1 ALT-2 PEYWKPSTFG GEVGFNIVKT ATLKKLVCLN TKTCPYVSFR VPDASQDDGP AVERPSTEL         (SEQ ID NO: 4)
COX-1 ALT-3 PEYWKPSTFG GEVGFNIVKT ATLKKLVCLN TKTCPYVSFR VPDASQDDGP AVERPSTEL         (SEQ ID NO: 6)
COX-1 ALT-4 PEYWKPSTFG GEVGFNIVKT ATLKKLVCLN TKTCPYVSFR VPDASQDDGP AVERPSTEL         (SEQ ID NO: 8)
```

FIGURE 6

Human Tissue Distribution of COX-1 Variant ALT-4 mRNA

Primers for PCR analysis:

ALT-4 F  TACATTAGGAGCCGGGATG  (SEQ ID NO: 37)
ALT-4 R  TGGTGCTGGCATGGATAGTA  (SEQ ID NO: 38)

Induction of COX-1 Variant ALT-4 by 20% FBS in SK-N-SH Cells

SEQUENCE LISTING

<160> NUMBER OF SEQ ID NOS: 38

<210> SEQ ID NO 1
<211> LENGTH: 2022
<212> TYPE: DNA
<213> ORGANISM: Homo sapiens
<220> FEATURE:
<221> NAME/KEY: CDS
<222> LOCATION: (298)...(2022)

<400> SEQUENCE: 1

```
atgagccgga gtctcttgct ccggttcttg ctgttcctgc tcctgctccc gccgctcccc       60
gtcctgctcg cggacccagg ggcgcccacg ccagggcct ctttgggagg aagccgcagg       120
caccaaggga aatgagttcc ctttctccag cctctaaccg tctgggaacc catcctgatt      180
cccattgcca gtggagaagg tctccctgg tgaagacttc gggagaacat gggagatgga      240
aatacattta ggagccggga tgcttcatct ggggtttaag agatccccat tgagcaa atg    300
                                                                      Met
                                                                       1 agg aaa ccg agg ctc atg aat ccc tgt tgt tac tat cca tgc cag cac        348
Arg Lys Pro Arg Leu Met Asn Pro Cys Cys Tyr Tyr Pro Cys Gln His
          5                  10                  15 cag ggc atc tgt gtc cgc ttc ggc ctt gac cgc tac cag tgt gac tgc        396
Gln Gly Ile Cys Val Arg Phe Gly Leu Asp Arg Tyr Gln Cys Asp Cys
     20                  25                  30 acc cgc acg ggc tat tcc ggc ccc aac tgc acc atc cct ggc ctg tgg        444
Thr Arg Thr Gly Tyr Ser Gly Pro Asn Cys Thr Ile Pro Gly Leu Trp
 35                  40                  45 acc tgg ctc cgg aat tca ctg cgg ccc agc ccc tct ttc acc cac ttc        492
Thr Trp Leu Arg Asn Ser Leu Arg Pro Ser Pro Ser Phe Thr His Phe
 50                  55                  60                  65 ctg ctc act cac ggg cgc tgg ttc tgg gag ttt gtc aat gcc acc ttc        540
Leu Leu Thr His Gly Arg Trp Phe Trp Glu Phe Val Asn Ala Thr Phe
                 70                  75                  80 atc cga gag atg ctc atg cgc ctg gta ctc aca gtg cgc tcc aac ctt        588
Ile Arg Glu Met Leu Met Arg Leu Val Leu Thr Val Arg Ser Asn Leu
             85                  90                  95 atc ccc agt ccc ccc acc tac aac tca gca cat gac tac atc agc tgg        636
Ile Pro Ser Pro Pro Thr Tyr Asn Ser Ala His Asp Tyr Ile Ser Trp
        100                 105                 110 gag tct ttc tcc aac gtg agc tat tac act cgt att ctg ccc tct gtg        684
Glu Ser Phe Ser Asn Val Ser Tyr Tyr Thr Arg Ile Leu Pro Ser Val
    115                 120                 125 cct aaa gat tgc ccc aca ccc atg gga acc aaa ggg aag aag cag ttg        732
Pro Lys Asp Cys Pro Thr Pro Met Gly Thr Lys Gly Lys Lys Gln Leu
130                 135                 140                 145 cca gat gcc cag ctc ctg gcc cgc cgc ttc ctg ctc agg agg aag ttc        780
Pro Asp Ala Gln Leu Leu Ala Arg Arg Phe Leu Leu Arg Arg Lys Phe
                150                 155                 160 ata cct gac ccc caa ggc acc aac ctc atg ttt gcc ttc ttt gca caa        828
Ile Pro Asp Pro Gln Gly Thr Asn Leu Met Phe Ala Phe Phe Ala Gln
            165                 170                 175 cac ttc acc cac cag ttc ttc aaa act tct ggc aag atg ggt cct ggc        876
His Phe Thr His Gln Phe Phe Lys Thr Ser Gly Lys Met Gly Pro Gly
        180                 185                 190 ttc acc aag gcc ttg ggc cat ggg gta gac ctc ggc cac att tat gga        924
Phe Thr Lys Ala Leu Gly His Gly Val Asp Leu Gly His Ile Tyr Gly
    195                 200                 205
```

```
                                                -continued gac aat ctg gag cgt cag tat caa ctg cgg ctc ttt aag gat ggg aaa      972
Asp Asn Leu Glu Arg Gln Tyr Gln Leu Arg Leu Phe Lys Asp Gly Lys
210                 215                 220                 225 ctc aag tac cag gtg ctg gat gga gaa atg tac ccg ccc tcg gta gaa     1020
Leu Lys Tyr Gln Val Leu Asp Gly Glu Met Tyr Pro Pro Ser Val Glu
                230                 235                 240 gag gcg cct gtg ttg atg cac tac ccc cga ggc atc ccg ccc cag agc     1068
Glu Ala Pro Val Leu Met His Tyr Pro Arg Gly Ile Pro Pro Gln Ser
        245                 250                 255 cag atg gct gtg ggc cag gag gtg ttt ggg ctg ctt cct ggg ctc atg     1116
Gln Met Ala Val Gly Gln Glu Val Phe Gly Leu Leu Pro Gly Leu Met
    260                 265                 270 ctg tat gcc acg ctc tgg cta cgt gag cac aac cgt gtg tgt gac ctg     1164
Leu Tyr Ala Thr Leu Trp Leu Arg Glu His Asn Arg Val Cys Asp Leu
275                 280                 285 ctg aag gct gag cac ccc acc tgg ggc gat gag cag ctt ttc cag acg     1212
Leu Lys Ala Glu His Pro Thr Trp Gly Asp Glu Gln Leu Phe Gln Thr
290                 295                 300                 305 acc cgc ctc atc ctc ata ggg gag acc atc aag att gtc atc gag gag     1260
Thr Arg Leu Ile Leu Ile Gly Glu Thr Ile Lys Ile Val Ile Glu Glu
                310                 315                 320 tac gtg cag cag ctg agt ggc tat ttc ctg cag ctg aaa ttt gac cca     1308
Tyr Val Gln Gln Leu Ser Gly Tyr Phe Leu Gln Leu Lys Phe Asp Pro
        325                 330                 335 gag ctg ctg ttc ggt gtc cag ttc caa tac cgc aac cgc att gcc atg     1356
Glu Leu Leu Phe Gly Val Gln Phe Gln Tyr Arg Asn Arg Ile Ala Met
    340                 345                 350 gag ttc aac cat ctc tac cac tgg cac ccc ctc atg cct gac tcc ttc     1404
Glu Phe Asn His Leu Tyr His Trp His Pro Leu Met Pro Asp Ser Phe
355                 360                 365 aag gtg ggc tcc cag gag tac agc tac gag cag ttg ttg ttc aac acc     1452
Lys Val Gly Ser Gln Glu Tyr Ser Tyr Glu Gln Phe Leu Phe Asn Thr
370                 375                 380                 385 tcc atg ttg gtg gac tat ggg gtt gag gcc ctg gtg gat gcc ttc tct     1500
Ser Met Leu Val Asp Tyr Gly Val Glu Ala Leu Val Asp Ala Phe Ser
                390                 395                 400 cgc cag att gct ggc cgg atc ggt ggg ggc agg aac atg gac cac cac     1548
Arg Gln Ile Ala Gly Arg Ile Gly Gly Gly Arg Asn Met Asp His His
        405                 410                 415 atc ctg cat gtg gct gtg gat gtc atc agg gag tct cgg gag atg cgg     1596
Ile Leu His Val Ala Val Asp Val Ile Arg Glu Ser Arg Glu Met Arg
    420                 425                 430 ctg cag ccc ttc aat gag tac cgc aag agg ttt ggc atg aaa ccc tac     1644
Leu Gln Pro Phe Asn Glu Tyr Arg Lys Arg Phe Gly Met Lys Pro Tyr
435                 440                 445 acc tcc ttc cag gag ctc gta gga gag aag gag atg gca gca gag ttg     1692
Thr Ser Phe Gln Glu Leu Val Gly Glu Lys Glu Met Ala Ala Glu Leu
450                 455                 460                 465 gag gaa ttg tat gga gac att gat gcg ttg gag ttc tac cct gga ctg     1740
Glu Glu Leu Tyr Gly Asp Ile Asp Ala Leu Glu Phe Tyr Pro Gly Leu
                470                 475                 480 ctt ctt gaa aag tgc cat cca aac tct atc ttt ggg gag agt atg ata     1788
Leu Leu Glu Lys Cys His Pro Asn Ser Ile Phe Gly Glu Ser Met Ile
        485                 490                 495 gag att ggg gct ccc ttt tcc ctc aag ggt ctc cta ggg aat ccc atc     1836
Glu Ile Gly Ala Pro Phe Ser Leu Lys Gly Leu Leu Gly Asn Pro Ile
    500                 505                 510 tgt tct ccg gag tac tgg aag ccg agc aca ttt ggc ggc gag gtg ggc     1884
Cys Ser Pro Glu Tyr Trp Lys Pro Ser Thr Phe Gly Gly Glu Val Gly
515                 520                 525
```

```
ttt aac att gtc aag acg gcc aca ctg aag aag ctg gtc tgc ctc aac    1932
Phe Asn Ile Val Lys Thr Ala Thr Leu Lys Lys Leu Val Cys Leu Asn
530             535                 540                 545 acc aag acc tgt ccc tac gtt tcc ttc cgt gtg ccg gat gcc agt cag    1980
Thr Lys Thr Cys Pro Tyr Val Ser Phe Arg Val Pro Asp Ala Ser Gln
            550                 555                 560 gat gat ggg cct gct gtg gag cga cca tcc aca gag ctc tga            2022
Asp Asp Gly Pro Ala Val Glu Arg Pro Ser Thr Glu Leu *
            565                 570
```

<210> SEQ ID NO 2
<211> LENGTH: 574
<212> TYPE: PRT
<213> ORGANISM: Homo sapiens

<400> SEQUENCE: 2

```
Met Arg Lys Pro Arg Leu Met Asn Pro Cys Cys Tyr Tyr Pro Cys Gln
1               5                   10                  15

His Gln Gly Ile Cys Val Arg Phe Gly Leu Asp Arg Tyr Gln Cys Asp
                20                  25                  30

Cys Thr Arg Thr Gly Tyr Ser Gly Pro Asn Cys Thr Ile Pro Gly Leu
            35                  40                  45

Trp Thr Trp Leu Arg Asn Ser Leu Arg Pro Ser Pro Ser Phe Thr His
50                  55                  60

Phe Leu Leu Thr His Gly Arg Trp Phe Trp Glu Phe Val Asn Ala Thr
65                  70                  75                  80

Phe Ile Arg Glu Met Leu Met Arg Leu Val Leu Thr Val Arg Ser Asn
                85                  90                  95

Leu Ile Pro Ser Pro Pro Thr Tyr Asn Ser Ala His Asp Tyr Ile Ser
            100                 105                 110

Trp Glu Ser Phe Ser Asn Val Ser Tyr Tyr Thr Arg Ile Leu Pro Ser
        115                 120                 125

Val Pro Lys Asp Cys Pro Thr Pro Met Gly Thr Lys Gly Lys Lys Gln
130                 135                 140

Leu Pro Asp Ala Gln Leu Leu Ala Arg Arg Phe Leu Leu Arg Arg Lys
145                 150                 155                 160

Phe Ile Pro Asp Pro Gln Gly Thr Asn Leu Met Phe Ala Phe Phe Ala
                165                 170                 175

Gln His Phe Thr His Gln Phe Phe Lys Thr Ser Gly Lys Met Gly Pro
            180                 185                 190

Gly Phe Thr Lys Ala Leu Gly His Gly Val Asp Leu Gly His Ile Tyr
        195                 200                 205

Gly Asp Asn Leu Glu Arg Gln Tyr Gln Leu Arg Leu Phe Lys Asp Gly
210                 215                 220

Lys Leu Lys Tyr Gln Val Leu Asp Gly Glu Met Tyr Pro Pro Ser Val
225                 230                 235                 240

Glu Glu Ala Pro Val Leu Met His Tyr Pro Arg Gly Ile Pro Pro Gln
                245                 250                 255

Ser Gln Met Ala Val Gly Gln Glu Val Phe Gly Leu Leu Pro Gly Leu
            260                 265                 270

Met Leu Tyr Ala Thr Leu Trp Leu Arg Glu His Asn Arg Val Cys Asp
        275                 280                 285

Leu Leu Lys Ala Glu His Pro Thr Trp Gly Asp Glu Gln Leu Phe Gln
290                 295                 300

Thr Thr Arg Leu Ile Leu Ile Gly Glu Thr Ile Lys Ile Val Ile Glu
```

-continued

```
            305                 310                 315                 320
Glu Tyr Val Gln Gln Leu Ser Gly Tyr Phe Leu Gln Leu Lys Phe Asp
                        325                 330                 335
Pro Glu Leu Leu Phe Gly Val Gln Phe Gln Tyr Arg Asn Arg Ile Ala
                340                 345                 350
Met Glu Phe Asn His Leu Tyr His Trp His Pro Leu Met Pro Asp Ser
            355                 360                 365
Phe Lys Val Gly Ser Gln Glu Tyr Ser Tyr Glu Gln Phe Leu Phe Asn
        370                 375                 380
Thr Ser Met Leu Val Asp Tyr Gly Val Glu Ala Leu Val Asp Ala Phe
385                 390                 395                 400
Ser Arg Gln Ile Ala Gly Arg Ile Gly Gly Arg Asn Met Asp His
                405                 410                 415
His Ile Leu His Val Ala Val Asp Val Ile Arg Glu Ser Arg Glu Met
            420                 425                 430
Arg Leu Gln Pro Phe Asn Glu Tyr Arg Lys Arg Phe Gly Met Lys Pro
        435                 440                 445
Tyr Thr Ser Phe Gln Glu Leu Val Gly Glu Lys Glu Met Ala Ala Glu
    450                 455                 460
Leu Glu Glu Leu Tyr Gly Asp Ile Asp Ala Leu Glu Phe Tyr Pro Gly
465                 470                 475                 480
Leu Leu Leu Glu Lys Cys His Pro Asn Ser Ile Phe Gly Glu Ser Met
                485                 490                 495
Ile Glu Ile Gly Ala Pro Phe Ser Leu Lys Gly Leu Leu Gly Asn Pro
            500                 505                 510
Ile Cys Ser Pro Glu Tyr Trp Lys Pro Ser Thr Phe Gly Gly Glu Val
        515                 520                 525
Gly Phe Asn Ile Val Lys Thr Ala Thr Leu Lys Lys Leu Val Cys Leu
    530                 535                 540
Asn Thr Lys Thr Cys Pro Tyr Val Ser Phe Arg Val Pro Asp Ala Ser
545                 550                 555                 560
Gln Asp Asp Gly Pro Ala Val Glu Arg Pro Ser Thr Glu Leu
                565                 570
```

<210> SEQ ID NO 3
<211> LENGTH: 1818
<212> TYPE: DNA
<213> ORGANISM: Homo sapiens
<220> FEATURE:
<221> NAME/KEY: CDS
<222> LOCATION: (298)...(1620)

<400> SEQUENCE: 3

```
atgagccgga gtctcttgct ccggttcttg ctgttcctgc tcctgctccc gccgctcccc        60
gtcctgctcg cggacccagg ggcgcccacg ccagggcct cttgggagg aagccgcagg         120 caccaaggga atgagttcc ctttctccag cctctaaccg tctgggaacc catcctgatt        180
cccattgcca gtgagaagg tctcccctgg tgaagacttc gggagaacat gggagatgga        240
aatacattta ggagccggga tgcttcatct ggggtttaag agatccccat tgagcaa atg      300
                                                                   Met
                                                                    1 agg aaa ccg agg ctc agg aag aag cag ttg cca gat gcc cag ctc ctg         348
Arg Lys Pro Arg Leu Arg Lys Lys Gln Leu Pro Asp Ala Gln Leu Leu
          5                  10                  15 gcc cgc cgc ttc ctg ctc agg agg aag ttc ata cct gac ccc caa ggc         396
Ala Arg Arg Phe Leu Leu Arg Arg Lys Phe Ile Pro Asp Pro Gln Gly
     20                  25                  30
```

-continued

```
            20                  25                  30
acc aac ctc atg ttt gcc ttc ttt gca caa cac ttc acc cac cag ttc      444
Thr Asn Leu Met Phe Ala Phe Phe Ala Gln His Phe Thr His Gln Phe
        35                  40                  45 ttc aaa act tct ggc aag atg ggt cct ggc ttc acc aag gcc ttg ggc      492
Phe Lys Thr Ser Gly Lys Met Gly Pro Gly Phe Thr Lys Ala Leu Gly
 50                  55                  60                  65 cat ggg gta gac ctc ggc cac att tat gga gac aat ctg gag cgt cag      540
His Gly Val Asp Leu Gly His Ile Tyr Gly Asp Asn Leu Glu Arg Gln
                 70                  75                  80 tat caa ctg cgg ctc ttt aag gat ggg aaa ctc aag tac cag gtg ctg      588
Tyr Gln Leu Arg Leu Phe Lys Asp Gly Lys Leu Lys Tyr Gln Val Leu
             85                  90                  95 gat gga gaa atg tac ccg ccc tcg gta gaa gag gcg cct gtg ttg atg      636
Asp Gly Glu Met Tyr Pro Pro Ser Val Glu Glu Ala Pro Val Leu Met
         100                 105                 110 cac tac ccc cga ggc atc ccg ccc cag agc cag atg gct gtg ggc cag      684
His Tyr Pro Arg Gly Ile Pro Pro Gln Ser Gln Met Ala Val Gly Gln
     115                 120                 125 gag gtg ttt ggg ctg ctt cct ggg ctc atg ctg tat gcc acg ctc tgg      732
Glu Val Phe Gly Leu Leu Pro Gly Leu Met Leu Tyr Ala Thr Leu Trp
130                 135                 140                 145 cta cgt gag cac aac cgt gtg tgt gac ctg ctg aag gct gag cac ccc      780
Leu Arg Glu His Asn Arg Val Cys Asp Leu Leu Lys Ala Glu His Pro
                150                 155                 160 acc tgg ggc gat gag cag ctt ttc cag acg acc cgc ctc atc ctc ata      828
Thr Trp Gly Asp Glu Gln Leu Phe Gln Thr Thr Arg Leu Ile Leu Ile
            165                 170                 175 ggg gag acc atc aag att gtc atc gag gag tac gtg cag cag ctg agt      876
Gly Glu Thr Ile Lys Ile Val Ile Glu Glu Tyr Val Gln Gln Leu Ser
        180                 185                 190 ggc tat ttc ctg cag ctg aaa ttt gac cca gag ctg ctg ttc ggt gtc      924
Gly Tyr Phe Leu Gln Leu Lys Phe Asp Pro Glu Leu Leu Phe Gly Val
    195                 200                 205 cag ttc caa tac cgc aac cgc att gcc atg gag ttc aac cat ctc tac      972
Gln Phe Gln Tyr Arg Asn Arg Ile Ala Met Glu Phe Asn His Leu Tyr
210                 215                 220                 225 cac tgg cac ccc ctc atg cct gac tcc ttc aag gtg ggc tcc cag gag     1020
His Trp His Pro Leu Met Pro Asp Ser Phe Lys Val Gly Ser Gln Glu
                230                 235                 240 tac agc tac gag cag ttc ttg ttc aac acc tcc atg ttg gtg gac tat     1068
Tyr Ser Tyr Glu Gln Phe Leu Phe Asn Thr Ser Met Leu Val Asp Tyr
            245                 250                 255 ggg gtt gag gcc ctg gtg gat gcc ttc tct cgc cag att gct ggc cgg     1116
Gly Val Glu Ala Leu Val Asp Ala Phe Ser Arg Gln Ile Ala Gly Arg
        260                 265                 270 atc ggt ggg ggc agg aac atg gac cac cac atc ctg cat gtg gct gtg     1164
Ile Gly Gly Gly Arg Asn Met Asp His His Ile Leu His Val Ala Val
    275                 280                 285 gat gtc atc agg gag tct cgg gag atg cgg ctg cag ccc ttc aat gag     1212
Asp Val Ile Arg Glu Ser Arg Glu Met Arg Leu Gln Pro Phe Asn Glu
290                 295                 300                 305 tac cgc aag agg ttt ggc atg aaa ccc tac acc tcc ttc cag gag ctc     1260
Tyr Arg Lys Arg Phe Gly Met Lys Pro Tyr Thr Ser Phe Gln Glu Leu
                310                 315                 320 gta gga gag aag gag atg gca gca gag ttg gag gaa ttg tat gga gac     1308
Val Gly Glu Lys Glu Met Ala Ala Glu Leu Glu Glu Leu Tyr Gly Asp
            325                 330                 335 att gat gcg ttg gag ttc tac cct gga ctg ctt ctt gaa aag tgc cat     1356
Ile Asp Ala Leu Glu Phe Tyr Pro Gly Leu Leu Leu Glu Lys Cys His
```

-continued

```
Ile Asp Ala Leu Glu Phe Tyr Pro Gly Leu Leu Glu Lys Cys His
        340                 345                 350 cca aac tct atc ttt ggg gag agt atg ata gag att ggg gct ccc ttt      1404
Pro Asn Ser Ile Phe Gly Glu Ser Met Ile Glu Ile Gly Ala Pro Phe
        355                 360                 365 tcc ctc aag ggt ctc cta ggg aat ccc atc tgt tct ccg gag tac tgg      1452
Ser Leu Lys Gly Leu Leu Gly Asn Pro Ile Cys Ser Pro Glu Tyr Trp
370                 375                 380                 385 aag ccg agc aca ttt ggc ggc gag gtg ggc ttt aac att gtc aag acg      1500
Lys Pro Ser Thr Phe Gly Gly Glu Val Gly Phe Asn Ile Val Lys Thr
                390                 395                 400 gcc aca ctg aag aag ctg gtc tgc ctc aac acc aag acc tgt ccc tac      1548
Ala Thr Leu Lys Lys Leu Val Cys Leu Asn Thr Lys Thr Cys Pro Tyr
            405                 410                 415 gtt tcc ttc cgt gtg ccg gat gcc agt cag gat gat ggg cct gct gtg      1596
Val Ser Phe Arg Val Pro Asp Ala Ser Gln Asp Asp Gly Pro Ala Val
        420                 425                 430 gag cga cca tcc aca gag ctc tga ggggcaggaa agcagcattc tggaggggag     1650
Glu Arg Pro Ser Thr Glu Leu *
        435                 440 agctttgtgc ttgtcattcc agagtgctga ggccagggct gatggtctta aatgctcatt   1710
ttctggtttg gcatggtgag tgttggggtt gacatttaga actttaagtc tcacccatta   1770
tctggaatat tgtgattctg tttattcttc cagaatgctg aactcctt                1818

<210> SEQ ID NO 4
<211> LENGTH: 440
<212> TYPE: PRT
<213> ORGANISM: Homo sapiens

<400> SEQUENCE: 4

Met Arg Lys Pro Arg Leu Arg Lys Lys Gln Leu Pro Asp Ala Gln Leu
1               5                   10                  15

Leu Ala Arg Arg Phe Leu Leu Arg Arg Lys Phe Ile Pro Asp Pro Gln
            20                  25                  30

Gly Thr Asn Leu Met Phe Ala Phe Phe Ala Gln His Phe Thr His Gln
        35                  40                  45

Phe Phe Lys Thr Ser Gly Lys Met Gly Pro Gly Phe Thr Lys Ala Leu
    50                  55                  60

Gly His Gly Val Asp Leu Gly His Ile Tyr Gly Asp Asn Leu Glu Arg
65                  70                  75                  80

Gln Tyr Gln Leu Arg Leu Phe Lys Asp Gly Lys Leu Lys Tyr Gln Val
                85                  90                  95

Leu Asp Gly Glu Met Tyr Pro Pro Ser Val Glu Glu Ala Pro Val Leu
            100                 105                 110

Met His Tyr Pro Arg Gly Ile Pro Pro Gln Ser Gln Met Ala Val Gly
        115                 120                 125

Gln Glu Val Phe Gly Leu Leu Pro Gly Leu Met Leu Tyr Ala Thr Leu
    130                 135                 140

Trp Leu Arg Glu His Asn Arg Val Cys Asp Leu Leu Lys Ala Glu His
145                 150                 155                 160

Pro Thr Trp Gly Asp Glu Gln Leu Phe Gln Thr Thr Arg Leu Ile Leu
                165                 170                 175

Ile Gly Glu Thr Ile Lys Ile Val Ile Glu Glu Tyr Val Gln Gln Leu
            180                 185                 190

Ser Gly Tyr Phe Leu Gln Leu Lys Phe Asp Pro Glu Leu Leu Phe Gly
        195                 200                 205
```

```
Val Gln Phe Gln Tyr Arg Asn Arg Ile Ala Met Glu Phe Asn His Leu
    210                 215                 220
Tyr His Trp His Pro Leu Met Pro Asp Ser Phe Lys Val Gly Ser Gln
225                 230                 235                 240
Glu Tyr Ser Tyr Glu Gln Phe Leu Phe Asn Thr Ser Met Leu Val Asp
                245                 250                 255
Tyr Gly Val Glu Ala Leu Val Asp Ala Phe Ser Arg Gln Ile Ala Gly
            260                 265                 270
Arg Ile Gly Gly Gly Arg Asn Met Asp His His Ile Leu His Val Ala
        275                 280                 285
Val Asp Val Ile Arg Glu Ser Arg Glu Met Arg Leu Gln Pro Phe Asn
290                 295                 300
Glu Tyr Arg Lys Arg Phe Gly Met Lys Pro Tyr Thr Ser Phe Gln Glu
305                 310                 315                 320
Leu Val Gly Glu Lys Glu Met Ala Ala Glu Leu Glu Leu Tyr Gly
                325                 330                 335
Asp Ile Asp Ala Leu Glu Phe Tyr Pro Gly Leu Leu Leu Glu Lys Cys
            340                 345                 350
His Pro Asn Ser Ile Phe Gly Glu Ser Met Ile Glu Ile Gly Ala Pro
        355                 360                 365
Phe Ser Leu Lys Gly Leu Leu Gly Asn Pro Ile Cys Ser Pro Glu Tyr
370                 375                 380
Trp Lys Pro Ser Thr Phe Gly Gly Glu Val Gly Phe Asn Ile Val Lys
385                 390                 395                 400
Thr Ala Thr Leu Lys Lys Leu Val Cys Leu Asn Thr Lys Thr Cys Pro
                405                 410                 415
Tyr Val Ser Phe Arg Val Pro Asp Ala Ser Gln Asp Asp Gly Pro Ala
            420                 425                 430
Val Glu Arg Pro Ser Thr Glu Leu
        435                 440

<210> SEQ ID NO 5
<211> LENGTH: 2109
<212> TYPE: DNA
<213> ORGANISM: Homo sapiens
<220> FEATURE:
<221> NAME/KEY: CDS
<222> LOCATION: (298)...(1911)

<400> SEQUENCE: 5
atgagccgga gtctcttgct ccggttcttg ctgttcctgc tcctgctccc gccgctcccc      60
gtcctgctcg cggacccagg ggcgcccacg ccagggggcct ctttgggagg aagccgcagg    120
caccaaggga aatgagttcc ctttctccag cctctaaccg tctgggaacc catcctgatt    180
cccattgcca gtgagaaggg tctcccctgg tgaagacttc gggagaacat gggagatgga    240
aatacattta ggagccggga tgcttcatct ggggtttaag agatccccat tgagcaa atg   300
                                                                 Met
                                                                   1 agg aaa ccg agg ctc atg aat ccc tgt tgt tac tat cca tgc cag cac      348
Arg Lys Pro Arg Leu Met Asn Pro Cys Cys Tyr Tyr Pro Cys Gln His
            5                   10                  15 cag ggc atc tgt gtc cgc ttc ggc ctt gac cgc tac cag tgt gac tgc      396
Gln Gly Ile Cys Val Arg Phe Gly Leu Asp Arg Tyr Gln Cys Asp Cys
        20                  25                  30 acc cgc acg ggc tat tcc ggc ccc aac tgc acc atc cct ggc ctg tgg      444
Thr Arg Thr Gly Tyr Ser Gly Pro Asn Cys Thr Ile Pro Gly Leu Trp
```

-continued

| | | | |
|---|---|---|---|
| | 35 | 40 | 45 |

| | | |
|---|---|---|
| acc tgg ctc cgg aat tca ctg cgg ccc agc ccc tct ttc acc cac ttc<br>Thr Trp Leu Arg Asn Ser Leu Arg Pro Ser Pro Ser Phe Thr His Phe<br>50                            55                    60                  65 | 492 |
| ctc ctc act cac ggg cgc tgg ttc tgg gag ttt gtc aat gcc acc ttc<br>Leu Leu Thr His Gly Arg Trp Phe Trp Glu Phe Val Asn Ala Thr Phe<br>                    70                    75                    80 | 540 |
| atc cga gag atg ctc atg cgc ctg gta ctc aca gtg cgc tcc aac ctt<br>Ile Arg Glu Met Leu Met Arg Leu Val Leu Thr Val Arg Ser Asn Leu<br>                85                    90                    95 | 588 |
| atc ccc agt ccc ccc acc tac aac tca gca cat gac tac atc agc tgg<br>Ile Pro Ser Pro Pro Thr Tyr Asn Ser Ala His Asp Tyr Ile Ser Trp<br>               100                  105                110 | 636 |
| gag tct ttc tcc aac gtg agc tat tac act cgt att ctg ccc tct gtg<br>Glu Ser Phe Ser Asn Val Ser Tyr Tyr Thr Arg Ile Leu Pro Ser Val<br>115                           120                  125 | 684 |
| cct aaa gat tgc ccc aca ccc atg gga acc aaa ggg aag aag cag ttg<br>Pro Lys Asp Cys Pro Thr Pro Met Gly Thr Lys Gly Lys Lys Gln Leu<br>130                           135                  140                145 | 732 |
| cca gat gcc cag ctc ctg gcc cgc cgc ttc ctc agg agg aag ttc<br>Pro Asp Ala Gln Leu Leu Ala Arg Arg Phe Leu Leu Arg Arg Lys Phe<br>                   150                  155                160 | 780 |
| ata cct gac ccc caa ggc acc aac ctc atg ttt gcc ttc ttt gca caa<br>Ile Pro Asp Pro Gln Gly Thr Asn Leu Met Phe Ala Phe Phe Ala Gln<br>               165                  170                175 | 828 |
| cac ttc acc cac cag ttc ttc aaa act tct ggc aag atg ggt cct ggc<br>His Phe Thr His Gln Phe Phe Lys Thr Ser Gly Lys Met Gly Pro Gly<br>180                         185                  190 | 876 |
| ttc acc aag gcc ttg ggc cat ggg gta gac ctc ggc cac att tat gga<br>Phe Thr Lys Ala Leu Gly His Gly Val Asp Leu Gly His Ile Tyr Gly<br>195                         200                  205 | 924 |
| gac aat ctg gag cgt cag tat caa ctg cgg ctc ttt aag gat ggg aaa<br>Asp Asn Leu Glu Arg Gln Tyr Gln Leu Arg Leu Phe Lys Asp Gly Lys<br>210                         215                  220                225 | 972 |
| ctc aag tac cag gtg ctg gat gga gaa atg tac ccg ccc tcg gta gaa<br>Leu Lys Tyr Gln Val Leu Asp Gly Glu Met Tyr Pro Pro Ser Val Glu<br>               230                  235                240 | 1020 |
| gag gcg cct gtg ttg atg cac tac ccc cga ggc atc ccg ccc cag agc<br>Glu Ala Pro Val Leu Met His Tyr Pro Arg Gly Ile Pro Pro Gln Ser<br>               245                  250                255 | 1068 |
| cag atg gct gtg ggc cag gag gtg ttt ggg ctg ctt cct ggg ctc atg<br>Gln Met Ala Val Gly Gln Glu Val Phe Gly Leu Leu Pro Gly Leu Met<br>260                         265                  270 | 1116 |
| ctg tat gcc acg ctc tgg cta cgt gag cac aac cgt gtg tgt gac ctg<br>Leu Tyr Ala Thr Leu Trp Leu Arg Glu His Asn Arg Val Cys Asp Leu<br>275                         280                  285 | 1164 |
| ctg aag gct gag cac ccc acc tgg ggc gat gag cag ctt ttc cag acg<br>Leu Lys Ala Glu His Pro Thr Trp Gly Asp Glu Gln Leu Phe Gln Thr<br>290                         295                  300                305 | 1212 |
| acc cgc ctc atc ctc ata ggg gag acc atc aag att gtc atc gag gag<br>Thr Arg Leu Ile Leu Ile Gly Glu Thr Ile Lys Ile Val Ile Glu Glu<br>               310                  315                320 | 1260 |
| tac gtg cag cag ctg agt ggc tat ttc ctg cag ctg aaa ttt gac cca<br>Tyr Val Gln Gln Leu Ser Gly Tyr Phe Leu Gln Leu Lys Phe Asp Pro<br>               325                  330                335 | 1308 |
| gag ctg ctg ttc ggt gtc cag ttc caa tac cgc aac cgc att gcc atg<br>Glu Leu Leu Phe Gly Val Gln Phe Gln Tyr Arg Asn Arg Ile Ala Met<br>               340                  345                350 | 1356 |
| gag ttc aac cat ctc tac cac tgg cac ccc ctc atg cct gac tcc ttc | 1404 |

```
            Glu Phe Asn His Leu Tyr His Trp His Pro Leu Met Pro Asp Ser Phe
                355                 360                 365 aag atc ggt ggg ggc agg aac atg gac cac cac atc ctg cat gtg gct      1452
Lys Ile Gly Gly Gly Arg Asn Met Asp His His Ile Leu His Val Ala
370                 375                 380                 385 gtg gat gtc atc agg gag tct cgg gag atg cgg ctg cag ccc ttc aat      1500
Val Asp Val Ile Arg Glu Ser Arg Glu Met Arg Leu Gln Pro Phe Asn
                390                 395                 400 gag tac cgc aag agg ttt ggc atg aaa ccc tac acc tcc ttc cag gag      1548
Glu Tyr Arg Lys Arg Phe Gly Met Lys Pro Tyr Thr Ser Phe Gln Glu
            405                 410                 415 ctc gta gga gag aag gag atg gca gca gag ttg gag gaa ttg tat gga      1596
Leu Val Gly Glu Lys Glu Met Ala Ala Glu Leu Glu Glu Leu Tyr Gly
        420                 425                 430 gac att gat gcg ttg gag ttc tac cct gga ctg ctt ctt gaa aag tgc      1644
Asp Ile Asp Ala Leu Glu Phe Tyr Pro Gly Leu Leu Leu Glu Lys Cys
    435                 440                 445 cat cca aac tct atc ttt ggg gag agt atg ata gag att ggg gct ccc      1692
His Pro Asn Ser Ile Phe Gly Glu Ser Met Ile Glu Ile Gly Ala Pro
450                 455                 460                 465 ttt tcc ctc aag ggt ctc cta ggg aat ccc atc tgt tct ccg gag tac      1740
Phe Ser Leu Lys Gly Leu Leu Gly Asn Pro Ile Cys Ser Pro Glu Tyr
                470                 475                 480 tgg aag ccg agc aca ttt ggc ggc gag gtg ggc ttt aac att gtc aag      1788
Trp Lys Pro Ser Thr Phe Gly Gly Glu Val Gly Phe Asn Ile Val Lys
                485                 490                 495 acg gcc aca ctg aag aag ctg gtc tgc ctc aac acc aag acc tgt ccc      1836
Thr Ala Thr Leu Lys Lys Leu Val Cys Leu Asn Thr Lys Thr Cys Pro
                500                 505                 510 tac gtt tcc ttc cgt gtg ccg gat gcc agt cag gat gat ggg cct gct      1884
Tyr Val Ser Phe Arg Val Pro Asp Ala Ser Gln Asp Asp Gly Pro Ala
            515                 520                 525 gtg gag cga cca tcc aca gag ctc tga ggggcaggaa agcagcattc            1931
Val Glu Arg Pro Ser Thr Glu Leu  *
530                 535 tggaggggag agctttgtgc ttgtcattcc agagtgctga ggccagggct gatggtctta    1991
aatgctcatt ttctggtttg gcatggtgag tgttggggtt gacatttaga actttaagtc   2051
tcacccatta tctggaatat tgtgattctg tttattcttc agaatgctg aactccctt     2109

<210> SEQ ID NO 6
<211> LENGTH: 537
<212> TYPE: PRT
<213> ORGANISM: Homo sapiens

<400> SEQUENCE: 6

Met Arg Lys Pro Arg Leu Met Asn Pro Cys Cys Tyr Tyr Pro Cys Gln
1               5                   10                  15

His Gln Gly Ile Cys Val Arg Phe Gly Leu Asp Arg Tyr Gln Cys Asp
            20                  25                  30

Cys Thr Arg Thr Gly Tyr Ser Gly Pro Asn Cys Thr Ile Pro Gly Leu
        35                  40                  45

Trp Thr Trp Leu Arg Asn Ser Leu Arg Pro Ser Pro Ser Phe Thr His
    50                  55                  60

Phe Leu Leu Thr His Gly Arg Trp Phe Trp Glu Phe Val Asn Ala Thr
65                  70                  75                  80

Phe Ile Arg Glu Met Leu Met Arg Leu Val Leu Thr Val Arg Ser Asn
                85                  90                  95
```

```
Leu Ile Pro Ser Pro Thr Tyr Asn Ser Ala His Asp Tyr Ile Ser
             100                 105                 110
Trp Glu Ser Phe Ser Asn Val Ser Tyr Tyr Thr Arg Ile Leu Pro Ser
             115                 120                 125
Val Pro Lys Asp Cys Pro Thr Pro Met Gly Thr Lys Gly Lys Gln
130                 135                 140
Leu Pro Asp Ala Gln Leu Leu Ala Arg Arg Phe Leu Leu Arg Arg Lys
145                 150                 155                 160
Phe Ile Pro Asp Pro Gln Gly Thr Asn Leu Met Phe Ala Phe Phe Ala
                 165                 170                 175
Gln His Phe Thr His Gln Phe Phe Lys Thr Ser Gly Lys Met Gly Pro
             180                 185                 190
Gly Phe Thr Lys Ala Leu Gly His Gly Val Asp Leu Gly His Ile Tyr
             195                 200                 205
Gly Asp Asn Leu Glu Arg Gln Tyr Gln Leu Arg Leu Phe Lys Asp Gly
             210                 215                 220
Lys Leu Lys Tyr Gln Val Leu Asp Gly Glu Met Tyr Pro Pro Ser Val
225                 230                 235                 240
Glu Glu Ala Pro Val Leu Met His Tyr Pro Arg Gly Ile Pro Pro Gln
                 245                 250                 255
Ser Gln Met Ala Val Gly Gln Glu Val Phe Gly Leu Leu Pro Gly Leu
             260                 265                 270
Met Leu Tyr Ala Thr Leu Trp Leu Arg Glu His Asn Arg Val Cys Asp
             275                 280                 285
Leu Leu Lys Ala Glu His Pro Thr Trp Gly Asp Glu Gln Leu Phe Gln
             290                 295                 300
Thr Thr Arg Leu Ile Leu Ile Gly Glu Thr Ile Lys Ile Val Ile Glu
305                 310                 315                 320
Glu Tyr Val Gln Gln Leu Ser Gly Tyr Phe Leu Gln Leu Lys Phe Asp
                 325                 330                 335
Pro Glu Leu Leu Phe Gly Val Gln Phe Gln Tyr Arg Asn Arg Ile Ala
                 340                 345                 350
Met Glu Phe Asn His Leu Tyr His Trp His Pro Leu Met Pro Asp Ser
             355                 360                 365
Phe Lys Ile Gly Gly Gly Arg Asn Met Asp His His Ile Leu His Val
             370                 375                 380
Ala Val Asp Val Ile Arg Glu Ser Arg Glu Met Arg Leu Gln Pro Phe
385                 390                 395                 400
Asn Glu Tyr Arg Lys Arg Phe Gly Met Lys Pro Tyr Thr Ser Phe Gln
                 405                 410                 415
Glu Leu Val Gly Glu Lys Glu Met Ala Ala Glu Leu Glu Glu Leu Tyr
             420                 425                 430
Gly Asp Ile Asp Ala Leu Glu Phe Tyr Pro Gly Leu Leu Leu Glu Lys
             435                 440                 445
Cys His Pro Asn Ser Ile Phe Gly Glu Ser Met Ile Glu Ile Gly Ala
             450                 455                 460
Pro Phe Ser Leu Lys Gly Leu Leu Gly Asn Pro Ile Cys Ser Pro Glu
465                 470                 475                 480
Tyr Trp Lys Pro Ser Thr Phe Gly Gly Glu Val Gly Phe Asn Ile Val
                 485                 490                 495
Lys Thr Ala Thr Leu Lys Lys Leu Val Cys Leu Asn Thr Lys Thr Cys
             500                 505                 510
Pro Tyr Val Ser Phe Arg Val Pro Asp Ala Ser Gln Asp Asp Gly Pro
```

```
                515                 520                 525
Ala Val Glu Arg Pro Ser Thr Glu Leu
    530                 535

<210> SEQ ID NO 7
<211> LENGTH: 2280
<212> TYPE: DNA
<213> ORGANISM: Homo sapiens
<220> FEATURE:
<221> NAME/KEY: CDS
<222> LOCATION: (298)...(2082)

<400> SEQUENCE: 7
atgagccgga gtctcttgct ccggttcttg ctgttcctgc tcctgctccc gccgctcccc      60
gtcctgctcg cggacccagg ggcgcccacg ccagggggcct ctttgggagg aagccgcagg     120
```

-continued

| | |
|---|---|
| atg ggt cct ggc ttc acc aag gcc ttg ggc cat ggg gta gac ctc ggc<br>Met Gly Pro Gly Phe Thr Lys Ala Leu Gly His Gly Val Asp Leu Gly<br>210                    215                  220                  225 | 972 |
| cac att tat gga gac aat ctg gag cgt cag tat caa ctg cgg ctc ttt<br>His Ile Tyr Gly Asp Asn Leu Glu Arg Gln Tyr Gln Leu Arg Leu Phe<br>              230                  235                  240 | 1020 |
| aag gat ggg aaa ctc aag tac cag gtg ctg gat gga gaa atg tac ccg<br>Lys Asp Gly Lys Leu Lys Tyr Gln Val Leu Asp Gly Glu Met Tyr Pro<br>                  245                  250                  255 | 1068 |
| ccc tcg gta gaa gag gcg cct gtg ttg atg cac tac ccc cga ggc atc<br>Pro Ser Val Glu Glu Ala Pro Val Leu Met His Tyr Pro Arg Gly Ile<br>260                    265                  270 | 1116 |
| ccg ccc cag agc cag atg gct gtg ggc cag gag gtg ttt ggg ctg ctt<br>Pro Pro Gln Ser Gln Met Ala Val Gly Gln Glu Val Phe Gly Leu Leu<br>     275                  280                  285 | 1164 |
| cct ggg ctc atg ctg tat gcc acg ctc tgg cta cgt gag cac aac cgt<br>Pro Gly Leu Met Leu Tyr Ala Thr Leu Trp Leu Arg Glu His Asn Arg<br>290                    295                  300                  305 | 1212 |
| gtg tgt gac ctg ctg aag gct gag cac ccc acc tgg ggc gat gag cag<br>Val Cys Asp Leu Leu Lys Ala Glu His Pro Thr Trp Gly Asp Glu Gln<br>          310                  315                  320 | 1260 |
| ctt ttc cag acg acc cgc ctc atc ctc ata ggg gag acc atc aag att<br>Leu Phe Gln Thr Thr Arg Leu Ile Leu Ile Gly Glu Thr Ile Lys Ile<br>                  325                  330                  335 | 1308 |
| gtc atc gag gag tac gtg cag cag ctg agt ggc tat ttc ctg cag ctg<br>Val Ile Glu Glu Tyr Val Gln Gln Leu Ser Gly Tyr Phe Leu Gln Leu<br>340                    345                  350 | 1356 |
| aaa ttt gac cca gag ctg ctg ttc ggt gtc cag ttc caa tac cgc aac<br>Lys Phe Asp Pro Glu Leu Leu Phe Gly Val Gln Phe Gln Tyr Arg Asn<br>     355                  360                  365 | 1404 |
| cgc att gcc atg gag ttc aac cat ctc tac cac tgg cac ccc ctc atg<br>Arg Ile Ala Met Glu Phe Asn His Leu Tyr His Trp His Pro Leu Met<br>370                    375                  380                  385 | 1452 |
| cct gac tcc ttc aag gtg ggc tcc cag gag tac agc tac gag cag ttc<br>Pro Asp Ser Phe Lys Val Gly Ser Gln Glu Tyr Ser Tyr Glu Gln Phe<br>          390                  395                  400 | 1500 |
| ttg ttc aac acc tcc atg ttg gtg gac tat ggg gtt gag gcc ctg gtg<br>Leu Phe Asn Thr Ser Met Leu Val Asp Tyr Gly Val Glu Ala Leu Val<br>              405                  410                  415 | 1548 |
| gat gcc ttc tct cgc cag att gct ggc cgg atc ggt ggg ggc agg aac<br>Asp Ala Phe Ser Arg Gln Ile Ala Gly Arg Ile Gly Gly Gly Arg Asn<br>                  420                  425                  430 | 1596 |
| atg gac cac cac atc ctg cat gtg gct gtg gat gtc atc agg gag tct<br>Met Asp His His Ile Leu His Val Ala Val Asp Val Ile Arg Glu Ser<br>435                    440                  445 | 1644 |
| cgg gag atg cgg ctg cag ccc ttc aat gag tac cgc aag agg ttt ggc<br>Arg Glu Met Arg Leu Gln Pro Phe Asn Glu Tyr Arg Lys Arg Phe Gly<br>450                    455                  460                  465 | 1692 |
| atg aaa ccc tac acc tcc ttc cag gag ctc gta gga gag aag gag atg<br>Met Lys Pro Tyr Thr Ser Phe Gln Glu Leu Val Gly Glu Lys Glu Met<br>              470                  475                  480 | 1740 |
| gca gca gag ttg gag gaa ttg tat gga gac att gat gcg ttg gag ttc<br>Ala Ala Glu Leu Glu Glu Leu Tyr Gly Asp Ile Asp Ala Leu Glu Phe<br>                  485                  490                  495 | 1788 |
| tac cct gga ctg ctt ctt gaa aag tgc cat cca aac tct atc ttt ggg<br>Tyr Pro Gly Leu Leu Leu Glu Lys Cys His Pro Asn Ser Ile Phe Gly<br>          500                  505                  510 | 1836 |
| gag agt atg ata gag att ggg gct ccc ttt tcc ctc aag ggt ctc cta<br>Glu Ser Met Ile Glu Ile Gly Ala Pro Phe Ser Leu Lys Gly Leu Leu | 1884 |

```
                515                 520                 525
ggg aat ccc atc tgt tct ccg gag tac tgg aag ccg agc aca ttt ggc    1932
Gly Asn Pro Ile Cys Ser Pro Glu Tyr Trp Lys Pro Ser Thr Phe Gly
530                 535                 540                 545 ggc gag gtg ggc ttt aac att gtc aag acg gcc aca ctg aag aag ctg    1980
Gly Glu Val Gly Phe Asn Ile Val Lys Thr Ala Thr Leu Lys Lys Leu
                550                 555                 560 gtc tgc ctc aac acc aag acc tgt ccc tac gtt tcc ttc cgt gtg ccg    2028
Val Cys Leu Asn Thr Lys Thr Cys Pro Tyr Val Ser Phe Arg Val Pro
            565                 570                 575 gat gcc agt cag gat gat ggg cct gct gtg gag cga cca tcc aca gag    2076
Asp Ala Ser Gln Asp Asp Gly Pro Ala Val Glu Arg Pro Ser Thr Glu
        580                 585                 590 ctc tga gggcaggaa agcagcattc tggaggggag agctttgtgc ttgtcattcc      2132
Leu * agagtgctga ggccagggct gatggtctta aatgctcatt ttctggtttg gcatggtgag  2192
tgttggggtt gacatttaga actttaagtc tcacccatta tctggaatat tgtgattctg  2252
tttattcttc cagaatgctg aactcctt                                     2280

<210> SEQ ID NO 8
<211> LENGTH: 594
<212> TYPE: PRT
<213> ORGANISM: Homo sapiens

<400> SEQUENCE: 8

Met Arg Lys Pro Arg Leu Ser Arg Cys His Asp Ser Pro Ser Ser Gln
1               5                   10                  15

Asn Thr Trp Trp Ala Gln Asp Leu Asn Ser Val Asn Pro Cys Cys Tyr
            20                  25                  30

Tyr Pro Cys Gln His Gln Gly Ile Cys Val Arg Phe Gly Leu Asp Arg
        35                  40                  45

Tyr Gln Cys Asp Cys Thr Arg Thr Gly Tyr Ser Gly Pro Asn Cys Thr
    50                  55                  60

Ile Pro Gly Leu Trp Thr Trp Leu Arg Asn Ser Leu Arg Pro Ser Pro
65                  70                  75                  80

Ser Phe Thr His Phe Leu Leu Thr His Gly Arg Trp Phe Trp Glu Phe
                85                  90                  95

Val Asn Ala Thr Phe Ile Arg Glu Met Leu Met Arg Leu Val Leu Thr
            100                 105                 110

Val Arg Ser Asn Leu Ile Pro Ser Pro Pro Thr Tyr Asn Ser Ala His
        115                 120                 125

Asp Tyr Ile Ser Trp Glu Ser Phe Ser Asn Val Ser Tyr Tyr Thr Arg
    130                 135                 140

Ile Leu Pro Ser Val Pro Lys Asp Cys Pro Thr Pro Met Gly Thr Lys
145                 150                 155                 160

Gly Lys Lys Gln Leu Pro Asp Ala Gln Leu Leu Ala Arg Arg Phe Leu
                165                 170                 175

Leu Arg Arg Lys Phe Ile Pro Asp Pro Gln Gly Thr Asn Leu Met Phe
            180                 185                 190

Ala Phe Phe Ala Gln His Phe Thr His Gln Phe Phe Lys Thr Ser Gly
        195                 200                 205

Lys Met Gly Pro Gly Phe Thr Lys Ala Leu Gly His Gly Val Asp Leu
    210                 215                 220

Gly His Ile Tyr Gly Asp Asn Leu Glu Arg Gln Tyr Gln Leu Arg Leu
225                 230                 235                 240
```

```
Phe Lys Asp Gly Lys Leu Lys Tyr Gln Val Leu Asp Gly Glu Met Tyr
                245                 250                 255

Pro Pro Ser Val Glu Ala Pro Val Leu Met His Tyr Pro Arg Gly
            260                 265                 270

Ile Pro Pro Gln Ser Gln Met Ala Val Gly Gln Glu Val Phe Gly Leu
            275                 280                 285

Leu Pro Gly Leu Met Leu Tyr Ala Thr Leu Trp Leu Arg Glu His Asn
290                 295                 300

Arg Val Cys Asp Leu Leu Lys Ala Glu His Pro Thr Trp Gly Asp Glu
305                 310                 315                 320

Gln Leu Phe Gln Thr Thr Arg Leu Ile Leu Ile Gly Glu Thr Ile Lys
                325                 330                 335

Ile Val Ile Glu Glu Tyr Val Gln Gln Leu Ser Gly Tyr Phe Leu Gln
                340                 345                 350

Leu Lys Phe Asp Pro Glu Leu Leu Phe Gly Val Gln Phe Gln Tyr Arg
            355                 360                 365

Asn Arg Ile Ala Met Glu Phe Asn His Leu Tyr His Trp His Pro Leu
370                 375                 380

Met Pro Asp Ser Phe Lys Val Gly Ser Gln Glu Tyr Ser Tyr Glu Gln
385                 390                 395                 400

Phe Leu Phe Asn Thr Ser Met Leu Val Asp Tyr Gly Val Glu Ala Leu
                405                 410                 415

Val Asp Ala Phe Ser Arg Gln Ile Ala Gly Arg Ile Gly Gly Gly Arg
            420                 425                 430

Asn Met Asp His His Ile Leu His Val Ala Val Asp Val Ile Arg Glu
            435                 440                 445

Ser Arg Glu Met Arg Leu Gln Pro Phe Asn Glu Tyr Arg Lys Arg Phe
450                 455                 460

Gly Met Lys Pro Tyr Thr Ser Phe Gln Glu Leu Val Gly Glu Lys Glu
465                 470                 475                 480

Met Ala Ala Glu Leu Glu Glu Leu Tyr Gly Asp Ile Asp Ala Leu Glu
                485                 490                 495

Phe Tyr Pro Gly Leu Leu Leu Glu Lys Cys His Pro Asn Ser Ile Phe
            500                 505                 510

Gly Glu Ser Met Ile Glu Ile Gly Ala Pro Phe Ser Leu Lys Gly Leu
            515                 520                 525

Leu Gly Asn Pro Ile Cys Ser Pro Glu Tyr Trp Lys Pro Ser Thr Phe
530                 535                 540

Gly Gly Glu Val Gly Phe Asn Ile Val Lys Thr Ala Thr Leu Lys Lys
545                 550                 555                 560

Leu Val Cys Leu Asn Thr Lys Thr Cys Pro Tyr Val Ser Phe Arg Val
                565                 570                 575

Pro Asp Ala Ser Gln Asp Asp Gly Pro Ala Val Glu Arg Pro Ser Thr
            580                 585                 590

Glu Leu

<210> SEQ ID NO 9
<211> LENGTH: 5093
<212> TYPE: DNA
<213> ORGANISM: Homo sapiens
<220> FEATURE:
<221> NAME/KEY: CDS
<222> LOCATION: (136)...(1935)

<400> SEQUENCE: 9
```

-continued

```
aggtgacagc tggagggagg agcggggtg gagccggggg aagggtgggg aggggatggg      60
ctggagctcc gggcagtgtg cgaggcgcac gcacaggagc ctgcactctg cgtcccgcac    120
cccagcagcc gcgcc atg agc cgg agt ctc ttg ctc tgg ttc ttg ctg ttc    171
               Met Ser Arg Ser Leu Leu Leu Trp Phe Leu Leu Phe
                 1               5                  10 ctg ctc ctg ctc ccg ccg ctc ccc gtc ctg ctc gcg gac cca ggg gcg    219
Leu Leu Leu Leu Pro Pro Leu Pro Val Leu Leu Ala Asp Pro Gly Ala
             15                  20                  25 ccc acg cca gtg aat ccc tgt tgt tac tat cca tgc cag cac cag ggc    267
Pro Thr Pro Val Asn Pro Cys Cys Tyr Tyr Pro Cys Gln His Gln Gly
         30                  35                  40 atc tgt gtc cgc ttc ggc ctt gac cgc tac cag tgt gac tgc acc cgc    315
Ile Cys Val Arg Phe Gly Leu Asp Arg Tyr Gln Cys Asp Cys Thr Arg
 45                  50                  55                  60 acg ggc tat tcc ggc ccc aac tgc acc atc cct ggc ctg tgg acc tgg    363
Thr Gly Tyr Ser Gly Pro Asn Cys Thr Ile Pro Gly Leu Trp Thr Trp
                 65                  70                  75 ctc cgg aat tca ctg cgg ccc agc ccc tct ttc acc cac ttc ctg ctc    411
Leu Arg Asn Ser Leu Arg Pro Ser Pro Ser Phe Thr His Phe Leu Leu
             80                  85                  90 act cac ggg cgc tgg ttc tgg gag ttt gtc aat gcc acc ttc atc cga    459
Thr His Gly Arg Trp Phe Trp Glu Phe Val Asn Ala Thr Phe Ile Arg
         95                 100                 105 gag atg ctc atg cgc ctg gta ctc aca gtg cgc tcc aac ctt atc ccc    507
Glu Met Leu Met Arg Leu Val Leu Thr Val Arg Ser Asn Leu Ile Pro
    110                 115                 120 agt ccc ccc acc tac aac tca gca cat gac tac atc agc tgg gag tct    555
Ser Pro Pro Thr Tyr Asn Ser Ala His Asp Tyr Ile Ser Trp Glu Ser
125                 130                 135                 140 ttc tcc aac gtg agc tat tac act cgt att ctg ccc tct gtg cct aaa    603
Phe Ser Asn Val Ser Tyr Tyr Thr Arg Ile Leu Pro Ser Val Pro Lys
                145                 150                 155 gat tgc ccc aca ccc atg gga acc aaa ggg aag aag cag ttg cca gat    651
Asp Cys Pro Thr Pro Met Gly Thr Lys Gly Lys Lys Gln Leu Pro Asp
            160                 165                 170 gcc cag ctc ctg gcc cgc cgc ttc ctg ctc agg agg aag ttc ata cct    699
Ala Gln Leu Leu Ala Arg Arg Phe Leu Leu Arg Arg Lys Phe Ile Pro
        175                 180                 185 gac ccc caa ggc acc aac ctc atg ttt gcc ttc ttt gca caa cac ttc    747
Asp Pro Gln Gly Thr Asn Leu Met Phe Ala Phe Phe Ala Gln His Phe
    190                 195                 200 acc cac cag ttc ttc aaa act tct ggc aag atg ggt cct ggc ttc acc    795
Thr His Gln Phe Phe Lys Thr Ser Gly Lys Met Gly Pro Gly Phe Thr
205                 210                 215                 220 aag gcc ttg ggc cat ggg gta gac ctc ggc cac att tat gga gac aat    843
Lys Ala Leu Gly His Gly Val Asp Leu Gly His Ile Tyr Gly Asp Asn
                225                 230                 235 ctg gag cgt cag tat caa ctg cgg ctc ttt aag gat ggg aaa ctc aag    891
Leu Glu Arg Gln Tyr Gln Leu Arg Leu Phe Lys Asp Gly Lys Leu Lys
            240                 245                 250 tac cag gtg ctg gat gga gaa atg tac ccg ccc tcg gta gaa gag gcg    939
Tyr Gln Val Leu Asp Gly Glu Met Tyr Pro Pro Ser Val Glu Glu Ala
        255                 260                 265 cct gtg ttg atg cac tac ccc cga ggc atc ccg ccc cag agc cag atg    987
Pro Val Leu Met His Tyr Pro Arg Gly Ile Pro Pro Gln Ser Gln Met
    270                 275                 280 gct gtg ggc cag gag gtg ttt ggg ctg ctt cct ggg ctc atg ctg tat   1035
Ala Val Gly Gln Glu Val Phe Gly Leu Leu Pro Gly Leu Met Leu Tyr
285                 290                 295                 300
```

```
gcc acg ctc tgg cta cgt gag cac aac cgt gtg tgt gac ctg ctg aag      1083
Ala Thr Leu Trp Leu Arg Glu His Asn Arg Val Cys Asp Leu Leu Lys
            305                 310                 315 gct gag cac ccc acc tgg ggc gat gag cag ctt ttc cag acg acc cgc      1131
Ala Glu His Pro Thr Trp Gly Asp Glu Gln Leu Phe Gln Thr Thr Arg
        320                 325                 330 ctc atc ctc ata ggg gag acc atc aag att gtc atc gag gag tac gtg      1179
Leu Ile Leu Ile Gly Glu Thr Ile Lys Ile Val Ile Glu Glu Tyr Val
            335                 340                 345 cag cag ctg agt ggc tat ttc ctg cag ctg aaa ttt gac cca gag ctg      1227
Gln Gln Leu Ser Gly Tyr Phe Leu Gln Leu Lys Phe Asp Pro Glu Leu
        350                 355                 360 ctg ttc ggt gtc cag ttc caa tac cgc aac cgc att gcc atg gag ttc      1275
Leu Phe Gly Val Gln Phe Gln Tyr Arg Asn Arg Ile Ala Met Glu Phe
365                 370                 375                 380 aac cat ctc tac cac tgg cac ccc ctc atg cct gac tcc ttc aag gtg      1323
Asn His Leu Tyr His Trp His Pro Leu Met Pro Asp Ser Phe Lys Val
            385                 390                 395 ggc tcc cag gag tac agc tac gag cag ttc ttg ttc aac acc tcc atg      1371
Gly Ser Gln Glu Tyr Ser Tyr Glu Gln Phe Leu Phe Asn Thr Ser Met
        400                 405                 410 ttg gtg gac tat ggg gtt gag gcc ctg gtg gat gcc ttc tct cgc cag      1419
Leu Val Asp Tyr Gly Val Glu Ala Leu Val Asp Ala Phe Ser Arg Gln
            415                 420                 425 att gct ggc cgg atc ggt ggg ggc agg aac atg gac cac cac atc ctg      1467
Ile Ala Gly Arg Ile Gly Gly Gly Arg Asn Met Asp His His Ile Leu
        430                 435                 440 cat gtg gct gtg gat gtc atc agg gag tct cgg gag atg cgg ctg cag      1515
His Val Ala Val Asp Val Ile Arg Glu Ser Arg Glu Met Arg Leu Gln
445                 450                 455                 460 ccc ttc aat gag tac cgc aag agg ttt ggc atg aaa ccc tac acc tcc      1563
Pro Phe Asn Glu Tyr Arg Lys Arg Phe Gly Met Lys Pro Tyr Thr Ser
            465                 470                 475 ttc cag gag ctc gta gga gag aag gag atg gca gca gag ttg gag gaa      1611
Phe Gln Glu Leu Val Gly Glu Lys Glu Met Ala Ala Glu Leu Glu Glu
        480                 485                 490 ttg tat gga gac att gat gcg ttg gag ttc tac cct gga ctg ctt ctt      1659
Leu Tyr Gly Asp Ile Asp Ala Leu Glu Phe Tyr Pro Gly Leu Leu Leu
            495                 500                 505 gaa aag tgc cat cca aac tct atc ttt ggg gag agt atg ata gag att      1707
Glu Lys Cys His Pro Asn Ser Ile Phe Gly Glu Ser Met Ile Glu Ile
        510                 515                 520 ggg gct ccc ttt tcc ctc aag ggt ctc cta ggg aat ccc atc tgt tct      1755
Gly Ala Pro Phe Ser Leu Lys Gly Leu Leu Gly Asn Pro Ile Cys Ser
525                 530                 535                 540 ccg gag tac tgg aag ccg agc aca ttt ggc ggc gag gtg ggc ttt aac      1803
Pro Glu Tyr Trp Lys Pro Ser Thr Phe Gly Gly Glu Val Gly Phe Asn
            545                 550                 555 att gtc aag acg gcc aca ctg aag aag ctg gtc tgc ctc aac acc aag      1851
Ile Val Lys Thr Ala Thr Leu Lys Lys Leu Val Cys Leu Asn Thr Lys
        560                 565                 570 acc tgt ccc tac gtt tcc ttc cgt gtg ccg gat gcc agt cag gat gat      1899
Thr Cys Pro Tyr Val Ser Phe Arg Val Pro Asp Ala Ser Gln Asp Asp
            575                 580                 585 ggg cct gct gtg gag cga cca tcc aca gag ctc tga ggggcaggaa           1945
Gly Pro Ala Val Glu Arg Pro Ser Thr Glu Leu *
        590                 595 agcagcattc tggaggggag agctttgtgc ttgtcattcc agagtgctga ggccagggct    2005
```

-continued

```
gatggtctta aatgctcatt ttctggtttg gcatggtgag tgttggggtt gacatttaga    2065
actttaagtc tcacccatta tctggaatat tgtgattctg tttattcttc cagaatgctg    2125
aactccttgt tagcccttca gattgttagg agtggttctc atttggtctg ccagaatact    2185
gggttcttag ttgacaacct agaatgtcag atttctggtt gatttgtaac acagtcattc    2245
taggatgtgg agctactgat gaaatctgct agaaagttag ggggttctta ttttgcattc    2305
cagaatcttg actttctgat tggtgattca aagtgttgtg ttcctggctg atgatccaga    2365
acagtggctc gtatcccaaa tctgtcagca tctggctgtc tagaatgtgg atttgattca    2425
ttttcctgtt cagtgagata tcatagagac ggagatccta aggtccaaca agaatgcatt    2485
ccctgaatct gtgcctgcac tgagagggca aggaagtggg tgttcttct tgggaccccc     2545 actaagaccc tggtctgagg atgtagagag aacaggtggg ctgtattcac gccattggtt    2605
ggaagctacc agagctctat ccccatccag gtcttgactc atggcagctg tttctcatga    2665
agctaataaa attcgctttc taaagttacc tgttatatat ctcttttggt cccatcctct    2725
aaagcagagg caacactgga acatggctag cctttcttgt agccatggct gggcgtgcta    2785
gaggttgcag catgagactt tctgctggga tccttgggcc catcactgta tagacatgct    2845
accactggta cttcctttct ccctgcgggc caggcactgc ccttttcagg aagctctctt    2905
aaaatacccc ttgccccaga cctggaagat ataacattca gttcccacca tctgattaaa    2965
acaacttcct cccttacaga gcatacaaca gagggggcac ccggggagga gagcacatac    3025
tgtgttccaa tttcacgctt ttaattctca tttgttctca caccaacagt gtgaagtgcg    3085
tggtataatc tccatttcaa accaaggaa gcagcctcag agtggtcgag tgacacacct     3145
cacgcaggct gagtccagag cttgtgctcc tcttgattcc tggtttgact cagttccagg    3205
cctgatcttg cctgtctggc tcagggtcaa agacagaatg gtggagtgta gcctccacct    3265
gatattcagg ctactcattc agtcccaaat atgtattttc ctaagtgttt actatgtgcc    3325
agttcctgta acaggtgtgg ggacacagca gtgagtaatc aatacagaca aggttctgcc    3385
cttatggagc tcacactcca gtggcagaca aacagaccat aaataaggaa acgatgaaat    3445
aagatatata caaggtgagt gtgacttccc ttctaacccc ctctgctctg tcctccccta    3505
ttgcgctctc aagaccagag acccaacagc agtgatctca gggcagacag ccctccactc    3565
cagctctgag acccttttct caggacctct gtaggcagca gagagagagg acagaggggt    3625
aagatgaggg gttgagggaa ggttcttcat gatccacact ttgggcttag tatttctcag    3685 gaaagagctat ggcccagaaa caacagggga actagagtt cggtctgaca gtccttgggg    3745
ttaagtctcc tgtcttatgg tccagaaact cctgtttctc cttagttggc tggaaactgc    3805
tcccatcatt ccttctggcc tctgctgaat gcagggaatg caatccttcc ctgctcttgc    3865
agttgctctg acgtagaaag atccttcggg tgctggaagt ctccatgaag agcttgtgtc    3925
ctgtcctttc ttgcagattc tatttcccct cttctgctaa tacctcttac tttgcttgag    3985
aatcctctcc tttcttatta atttcagtct tggtggttct atcagggtg cattctggcc      4045 aaggggtggg cctgtgaatc aatcctgggc aatcagacac cctctcctta aaaactggcc    4105
cgtggagact gagatcactg actctgactc atccccacag ctggctctga caagatggtc    4165
catttgttcc tgcttccgag atccccaggg cagcctggat ccctgccctt ctcaagactt    4225
tagcttttcc ttccatccgg tggcctattc caggaattcc tcttttgctt aaatcagttg    4285
gagtttgtgt ctgttgcttg taatcaagcc tttatggctg ctgggctgag tgacacaagc    4345
actttaatgg cctggaggga cttttaatca gtgaagatgc aatcagacaa gtgttttgga    4405
```

-continued

```
aagagcaccc tcgagaaggg tggatgacag ggcagagcag gaaggacagg aagctggcag    4465
aacggaggag gctgcagccg tggtccaacc aggagctgat ggcagctggg gctaggggaa    4525
gggctttgag ggtggaagga tgggatgggt tccagaggta ttcctctctt aaatgcaagt    4585
gcctagatta ggtagacttt gcttagtatt gacaactgca catgaaagtt ttgcaaaggg    4645
aaacaggcta aatgcaccaa gaaagcttct tcagagtgaa gaatcttaat gcttgtaatt    4705
taaacatttg ttcctggagt tttgatttgg tggatgtgat ggttggtttt atttgtcagt    4765
ttggttgggc tatagcacac agttatttaa tcaaacagta atctaggtgt ggctgtgaag    4825
gtattttgta gatgtgatta acatctacaa tcagttgact ttaagtgaaa gagattactt    4885
aaataatttg ggtgagctgc acctgattag ttgaaaggcc tcaagaacaa acactgcagt    4945
ttcctggaaa agaagaaact ttgcctcaag actatagcca tcgactcctg cctgagtttc    5005
cagcctgcta gtctgcccta tggatttgaa gtttgccaac cccaacaatt gtgtgaatta    5065
atttctaaaa ataaagctat atacagcc                                       5093
```

<210> SEQ ID NO 10
<211> LENGTH: 599
<212> TYPE: PRT
<213> ORGANISM: Homo sapiens

<400> SEQUENCE: 10

```
Met Ser Arg Ser Leu Leu Leu Trp Phe Leu Leu Phe Leu Leu Leu Leu
1               5                   10                  15

Pro Pro Leu Pro Val Leu Leu Ala Asp Pro Gly Ala Pro Thr Pro Val
            20                  25                  30

Asn Pro Cys Cys Tyr Tyr Pro Cys Gln His Gln Gly Ile Cys Val Arg
        35                  40                  45

Phe Gly Leu Asp Arg Tyr Gln Cys Asp Cys Thr Arg Thr Gly Tyr Ser
    50                  55                  60

Gly Pro Asn Cys Thr Ile Pro Gly Leu Trp Thr Trp Leu Arg Asn Ser
65                  70                  75                  80

Leu Arg Pro Ser Pro Ser Phe Thr His Phe Leu Thr His Gly Arg
                85                  90                  95

Trp Phe Trp Glu Phe Val Asn Ala Thr Phe Ile Arg Glu Met Leu Met
            100                 105                 110

Arg Leu Val Leu Thr Val Arg Ser Asn Leu Ile Pro Ser Pro Pro Thr
        115                 120                 125

Tyr Asn Ser Ala His Asp Tyr Ile Ser Trp Glu Ser Phe Ser Asn Val
    130                 135                 140

Ser Tyr Tyr Thr Arg Ile Leu Pro Ser Val Pro Lys Asp Cys Pro Thr
145                 150                 155                 160

Pro Met Gly Thr Lys Gly Lys Lys Gln Leu Pro Asp Ala Gln Leu Leu
                165                 170                 175

Ala Arg Arg Phe Leu Leu Arg Arg Lys Phe Ile Pro Asp Pro Gln Gly
            180                 185                 190

Thr Asn Leu Met Phe Ala Phe Phe Ala Gln His Phe Thr His Gln Phe
        195                 200                 205

Phe Lys Thr Ser Gly Lys Met Gly Pro Gly Phe Thr Lys Ala Leu Gly
    210                 215                 220

His Gly Val Asp Leu Gly His Ile Tyr Gly Asp Asn Leu Glu Arg Gln
225                 230                 235                 240

Tyr Gln Leu Arg Leu Phe Lys Asp Gly Lys Leu Lys Tyr Gln Val Leu
```

```
                    245                 250                 255
Asp Gly Glu Met Tyr Pro Pro Ser Val Glu Glu Ala Pro Val Leu Met
            260                 265                 270

His Tyr Pro Arg Gly Ile Pro Pro Gln Ser Gln Met Ala Val Gly Gln
            275                 280                 285

Glu Val Phe Gly Leu Leu Pro Gly Leu Met Leu Tyr Ala Thr Leu Trp
            290                 295                 300

Leu Arg Glu His Asn Arg Val Cys Asp Leu Leu Lys Ala Glu His Pro
305                 310                 315                 320

Thr Trp Gly Asp Glu Gln Leu Phe Gln Thr Thr Arg Leu Ile Leu Ile
            325                 330                 335

Gly Glu Thr Ile Lys Ile Val Ile Glu Glu Tyr Val Gln Gln Leu Ser
            340                 345                 350

Gly Tyr Phe Leu Gln Leu Lys Phe Asp Pro Glu Leu Leu Phe Gly Val
            355                 360                 365

Gln Phe Gln Tyr Arg Asn Arg Ile Ala Met Glu Phe Asn His Leu Tyr
            370                 375                 380

His Trp His Pro Leu Met Pro Asp Ser Phe Lys Val Gly Ser Gln Glu
385                 390                 395                 400

Tyr Ser Tyr Glu Gln Phe Leu Phe Asn Thr Ser Met Leu Val Asp Tyr
            405                 410                 415

Gly Val Glu Ala Leu Val Asp Ala Phe Ser Arg Gln Ile Ala Gly Arg
            420                 425                 430

Ile Gly Gly Gly Arg Asn Met Asp His His Ile Leu His Val Ala Val
            435                 440                 445

Asp Val Ile Arg Glu Ser Arg Glu Met Arg Leu Gln Pro Phe Asn Glu
450                 455                 460

Tyr Arg Lys Arg Phe Gly Met Lys Pro Tyr Thr Ser Phe Gln Glu Leu
465                 470                 475                 480

Val Gly Glu Lys Glu Met Ala Ala Glu Leu Glu Leu Tyr Gly Asp
            485                 490                 495

Ile Asp Ala Leu Glu Phe Tyr Pro Gly Leu Leu Leu Glu Lys Cys His
            500                 505                 510

Pro Asn Ser Ile Phe Gly Glu Ser Met Ile Glu Ile Gly Ala Pro Phe
            515                 520                 525

Ser Leu Lys Gly Leu Leu Gly Asn Pro Ile Cys Ser Pro Glu Tyr Trp
            530                 535                 540

Lys Pro Ser Thr Phe Gly Gly Glu Val Gly Phe Asn Ile Val Lys Thr
545                 550                 555                 560

Ala Thr Leu Lys Lys Leu Val Cys Leu Asn Thr Lys Thr Cys Pro Tyr
            565                 570                 575

Val Ser Phe Arg Val Pro Asp Ala Ser Gln Asp Gly Pro Ala Val
            580                 585                 590

Glu Arg Pro Ser Thr Glu Leu
            595

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
ggttcttgct gttcctgctc                                           20
```

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
tcacactggt agcggtcaag                                          20

<210> SEQ ID NO 13
<211> LENGTH: 21
<212> TYPE: DNA
<213> ORGANISM: Homo sapiens
<220> FEATURE:
<221> NAME/KEY: CDS
<222> LOCATION: (1)...(21)

<400> SEQUENCE: 13 atg agg aaa ccg agg ctc atg                                    21
Met Arg Lys Pro Arg Leu Met
 1               5

<210> SEQ ID NO 14
<211> LENGTH: 7
<212> TYPE: PRT
<213> ORGANISM: Homo sapiens

<400> SEQUENCE: 14

Met Arg Lys Pro Arg Leu Met
 1               5

<210> SEQ ID NO 15
<211> LENGTH: 81
<212> TYPE: DNA
<213> ORGANISM: Homo sapiens
<220> FEATURE:
<221> NAME/KEY: CDS
<222> LOCATION: (1)...(81)

<400> SEQUENCE: 15 atg agg aaa ccg agg ctc agt agg tgc cat gat tcc cca agc tca caa    48
Met Arg Lys Pro Arg Leu Ser Arg Cys His Asp Ser Pro Ser Ser Gln
 1               5                  10                  15 aat aca tgg tgg gcc cag gat ctg aac tca gtc                       81
Asn Thr Trp Trp Ala Gln Asp Leu Asn Ser Val
             20                  25

<210> SEQ ID NO 16
<211> LENGTH: 27
<212> TYPE: PRT
<213> ORGANISM: Homo sapiens

<400> SEQUENCE: 16

Met Arg Lys Pro Arg Leu Ser Arg Cys His Asp Ser Pro Ser Ser Gln
 1               5                  10                  15

Asn Thr Trp Trp Ala Gln Asp Leu Asn Ser Val
             20                  25

<210> SEQ ID NO 17
<211> LENGTH: 21
<212> TYPE: DNA
<213> ORGANISM: Homo sapiens
<220> FEATURE:
<221> NAME/KEY: CDS -continued

```
<222> LOCATION: (1)...(21)

<400> SEQUENCE: 17 atg agg aaa ccg agg ctc agg                                          21
Met Arg Lys Pro Arg Leu Arg
 1               5

<210> SEQ ID NO 18
<211> LENGTH: 7
<212> TYPE: PRT
<213> ORGANISM: Homo sapiens

<400> SEQUENCE: 18

Met Arg Lys Pro Arg Leu Arg
 1               5

<210> SEQ ID NO 19
<211> LENGTH: 27
<212> TYPE: DNA
<213> ORGANISM: Homo sapiens
<220> FEATURE:
<221> NAME/KEY: CDS
<222> LOCATION: (1)...(27)

<400> SEQUENCE: 19 aaa ccg agg ctc atg aat ccc tgt tgt                                  27
Lys Pro Arg Leu Met Asn Pro Cys Cys
 1               5

<210> SEQ ID NO 20
<211> LENGTH: 9
<212> TYPE: PRT
<213> ORGANISM: Homo sapiens

<400> SEQUENCE: 20

Lys Pro Arg Leu Met Asn Pro Cys Cys
 1               5

<210> SEQ ID NO 21
<211> LENGTH: 27
<212> TYPE: DNA
<213> ORGANISM: Homo sapiens
<220> FEATURE:
<221> NAME/KEY: CDS
<222> LOCATION: (1)...(27)

<400> SEQUENCE: 21 gat ctg aac tca gtc aat ccc tgt tgt                                  27
Asp Leu Asn Ser Val Asn Pro Cys Cys
 1               5

<210> SEQ ID NO 22
<211> LENGTH: 9
<212> TYPE: PRT
<213> ORGANISM: Homo sapiens

<400> SEQUENCE: 22

Asp Leu Asn Ser Val Asn Pro Cys Cys
 1               5

<210> SEQ ID NO 23
<211> LENGTH: 27
<212> TYPE: DNA
<213> ORGANISM: Homo sapiens
<220> FEATURE:
<221> NAME/KEY: CDS
<222> LOCATION: (1)...(27)
```

```
<400> SEQUENCE: 23 aaa ccg agg ctc agg aag aag cag ttg                                27
Lys Pro Arg Leu Arg Lys Lys Gln Leu
1               5

<210> SEQ ID NO 24
<211> LENGTH: 9
<212> TYPE: PRT
<213> ORGANISM: Homo sapiens

<400> SEQUENCE: 24

Lys Pro Arg Leu Arg Lys Lys Gln Leu
1               5

<210> SEQ ID NO 25
<211> LENGTH: 4465
<212> TYPE: DNA
<213> ORGANISM: Homo sapiens
<220> FEATURE:
<221> NAME/KEY: CDS
<222> LOCATION: (135)...(1946)

<400> SEQUENCE: 25
caattgtcat acgacttgca gtgagcgtca ggagcacgtc caggaactcc tcagcagcgc     60
ctccttcagc tccacagcca gacgccctca gacagcaaag cctaccccg cgccgcgccc    120 tgcccgccgc tcgg atg ctc gcc cgc gcc ctg ctg ctg tgc gcg gtc ctg    170
              Met Leu Ala Arg Ala Leu Leu Leu Cys Ala Val Leu
              1               5                   10 gcg ctc agc cat aca gca aat cct tgc tgt tcc cac cca tgt caa aac    218
Ala Leu Ser His Thr Ala Asn Pro Cys Cys Ser His Pro Cys Gln Asn
        15                  20                  25 cga ggt gta tgt atg agt gtg gga ttt gac cag tat aag tgc gat tgt    266
Arg Gly Val Cys Met Ser Val Gly Phe Asp Gln Tyr Lys Cys Asp Cys
    30                  35                  40 acc cgg aca gga ttc tat gga gaa aac tgc tca aca ccg gaa ttt ttg    314
Thr Arg Thr Gly Phe Tyr Gly Glu Asn Cys Ser Thr Pro Glu Phe Leu
45                  50                  55                  60 aca aga ata aaa tta ttt ctg aaa ccc act cca aac aca gtg cac tac    362
Thr Arg Ile Lys Leu Phe Leu Lys Pro Thr Pro Asn Thr Val His Tyr
                65                  70                  75 ata ctt acc cac ttc aag gga ttt tgg aac gtt gtg aat aac att ccc    410
Ile Leu Thr His Phe Lys Gly Phe Trp Asn Val Val Asn Asn Ile Pro
            80                  85                  90 ttc ctt cga aat gca att atg agt tat gtc ttg aca tcc aga tca cat    458
Phe Leu Arg Asn Ala Ile Met Ser Tyr Val Leu Thr Ser Arg Ser His
        95                  100                 105 ttg att gac agt cca cca act tac aat gct gac tat ggc tac aaa agc    506
Leu Ile Asp Ser Pro Pro Thr Tyr Asn Ala Asp Tyr Gly Tyr Lys Ser
    110                 115                 120 tgg gaa gcc ttc tct aac ctc tcc tat tat act aga gcc ctt cct cct    554
Trp Glu Ala Phe Ser Asn Leu Ser Tyr Tyr Thr Arg Ala Leu Pro Pro
125                 130                 135                 140 gtg cct gat gat tgc ccg act ccc ttg ggt gtc aaa ggt aaa aag cag    602
Val Pro Asp Asp Cys Pro Thr Pro Leu Gly Val Lys Gly Lys Lys Gln
                145                 150                 155 ctt cct gat tca aat gag att gtg gaa aaa ttg ctt cta aga aga aag    650
Leu Pro Asp Ser Asn Glu Ile Val Glu Lys Leu Leu Leu Arg Arg Lys
            160                 165                 170 ttc atc cct gat ccc cag ggc tca aac atg atg ttt gca ttc ttt gcc    698
Phe Ile Pro Asp Pro Gln Gly Ser Asn Met Met Phe Ala Phe Phe Ala
```

-continued

|     | 175 |     |     |     | 180 |     |     |     | 185 |     |     |     |     |
|-----|-----|-----|-----|-----|-----|-----|-----|-----|-----|-----|-----|-----|-----|
| cag | cac | ttc | acg | cat | cag | ttt | ttc | aag | aca | gat | cat | aag | cga | ggg | cca | 746 |
| Gln | His | Phe | Thr | His | Gln | Phe | Phe | Lys | Thr | Asp | His | Lys | Arg | Gly | Pro |

```
cag cac ttc acg cat cag ttt ttc aag aca gat cat aag cga ggg cca        746
Gln His Phe Thr His Gln Phe Phe Lys Thr Asp His Lys Arg Gly Pro
        190             195                 200 gct ttc acc aac ggg ctg ggc cat ggg gtg gac tta aat cat att tac        794
Ala Phe Thr Asn Gly Leu Gly His Gly Val Asp Leu Asn His Ile Tyr
205             210                 215                 220 ggt gaa act ctg gct aga cag cgt aaa ctg cgc ctt ttc aag gat gga        842
Gly Glu Thr Leu Ala Arg Gln Arg Lys Leu Arg Leu Phe Lys Asp Gly
                225                 230                 235 aaa atg aaa tat cag ata att gat gga gag atg tat cct ccc aca gtc        890
Lys Met Lys Tyr Gln Ile Ile Asp Gly Glu Met Tyr Pro Pro Thr Val
            240                 245                 250 aaa gat act cag gca gag atg atc tac cct cct caa gtc cct gag cat        938
Lys Asp Thr Gln Ala Glu Met Ile Tyr Pro Pro Gln Val Pro Glu His
            255                 260                 265 cta cgg ttt gct gtg ggg cag gag gtc ttt ggt ctg gtg cct ggt ctg        986
Leu Arg Phe Ala Val Gly Gln Glu Val Phe Gly Leu Val Pro Gly Leu
270             275                 280 atg atg tat gcc aca atc tgg ctg cgg gaa cac aac aga gta tgc gat       1034
Met Met Tyr Ala Thr Ile Trp Leu Arg Glu His Asn Arg Val Cys Asp
285             290                 295                 300 gtg ctt aaa cag gag cat cct gaa tgg ggt gat gag cag ttg ttc cag       1082
Val Leu Lys Gln Glu His Pro Glu Trp Gly Asp Glu Gln Leu Phe Gln
                305                 310                 315 aca agc agg cta ata ctg ata gga gag act att aag att gtg att gaa       1130
Thr Ser Arg Leu Ile Leu Ile Gly Glu Thr Ile Lys Ile Val Ile Glu
            320                 325                 330 gat tat gtg caa cac ttg agt ggc tat cac ttc aaa ctg aaa ttt gac       1178
Asp Tyr Val Gln His Leu Ser Gly Tyr His Phe Lys Leu Lys Phe Asp
            335                 340                 345 cca gaa cta ctt ttc aac aaa caa ttc cag tac caa aat cgt att gct       1226
Pro Glu Leu Leu Phe Asn Lys Gln Phe Gln Tyr Gln Asn Arg Ile Ala
350             355                 360 gct gaa ttt aac acc ctc tat cac tgg cat ccc ctt ctg cct gac acc       1274
Ala Glu Phe Asn Thr Leu Tyr His Trp His Pro Leu Leu Pro Asp Thr
365             370                 375                 380 ttt caa att cat gac cag aaa tac aac tat caa cag ttt atc tac aac       1322
Phe Gln Ile His Asp Gln Lys Tyr Asn Tyr Gln Gln Phe Ile Tyr Asn
                385                 390                 395 aac tct ata ttg ctg gaa cat gga att acc cag ttt gtt gaa tca ttc       1370
Asn Ser Ile Leu Leu Glu His Gly Ile Thr Gln Phe Val Glu Ser Phe
            400                 405                 410 acc agg caa att gct ggc agg gtt gct ggt ggt agg aat gtt cca ccc       1418
Thr Arg Gln Ile Ala Gly Arg Val Ala Gly Gly Arg Asn Val Pro Pro
            415                 420                 425 gca gta cag aaa gta tca cag gct tcc att gac cag agc agg cag atg       1466
Ala Val Gln Lys Val Ser Gln Ala Ser Ile Asp Gln Ser Arg Gln Met
430             435                 440 aaa tac cag tct ttt aat gag tac cgc aaa cgc ttt atg ctg aag ccc       1514
Lys Tyr Gln Ser Phe Asn Glu Tyr Arg Lys Arg Phe Met Leu Lys Pro
445             450                 455                 460 tat gaa tca ttt gaa gaa ctt aca gga gaa aag gaa atg tct gca gag       1562
Tyr Glu Ser Phe Glu Glu Leu Thr Gly Glu Lys Glu Met Ser Ala Glu
                465                 470                 475 ttg gaa gca ctc tat ggt gac atc gat gct gtg gag ctg tat cct gcc       1610
Leu Glu Ala Leu Tyr Gly Asp Ile Asp Ala Val Glu Leu Tyr Pro Ala
            480                 485                 490 ctt ctg gta gaa aag cct cgg cca gat gcc atc ttt ggt gaa acc atg       1658
```

```
                Leu Leu Val Glu Lys Pro Arg Pro Asp Ala Ile Phe Gly Glu Thr Met
                        495                 500                 505 gta gaa gtt gga gca cca ttc tcc ttg aaa gga ctt atg ggt aat gtt       1706
Val Glu Val Gly Ala Pro Phe Ser Leu Lys Gly Leu Met Gly Asn Val
        510                 515                 520 ata tgt tct cct gcc tac tgg aag cca agc act ttt ggt gga gaa gtg       1754
Ile Cys Ser Pro Ala Tyr Trp Lys Pro Ser Thr Phe Gly Gly Glu Val
525                 530                 535                 540 ggt ttt caa atc atc aac act gcc tca att cag tct ctc atc tgc aat       1802
Gly Phe Gln Ile Ile Asn Thr Ala Ser Ile Gln Ser Leu Ile Cys Asn
                545                 550                 555 aac gtg aag ggc tgt ccc ttt act tca ttc agt gtt cca gat cca gag       1850
Asn Val Lys Gly Cys Pro Phe Thr Ser Phe Ser Val Pro Asp Pro Glu
            560                 565                 570 ctc att aaa aca gtc acc atc aat gca agt tct tcc cgc tcc gga cta       1898
Leu Ile Lys Thr Val Thr Ile Asn Ala Ser Ser Ser Arg Ser Gly Leu
        575                 580                 585 gat gat atc aat ccc aca gta cta cta aaa gaa cgt tcg act gaa ctg       1946
Asp Asp Ile Asn Pro Thr Val Leu Leu Lys Glu Arg Ser Thr Glu Leu
    590                 595                 600 tagaagtcta atgatcatat ttatttattt atatgaacca tgtctattaa tttaattatt     2006
taataatatt tatattaaac tccttatgtt acttaacatc ttctgtaaca gaagtcagta     2066
ctcctgttgc ggagaaagga gtcatacttg tgaagacttt tatgtcacta ctctaaagat     2126
tttgctgttg ctgttaagtt tggaaaacag tttttattct gttttataaa ccagagagaa     2186
atgagttttg acgtcttttt acttgaattt caacttatat tataagaacg aaagtaaaga     2246
tgtttgaata cttaaacact atcacaagat ggcaaaatgc tgaaagtttt tacactgtcg     2306
atgtttccaa tgcatcttcc atgatgcatt agaagtaact aatgtttgaa attttaaagt     2366
acttttggtt attttttctgt catcaaacaa aaacaggtat cagtgcatta ttaaatgaat    2426
atttaaatta gacattacca gtaatttcat gtctactttt taaaatcagc aatgaaacaa     2486
taatttgaaa tttctaaatt catagggtag aatcacctgt aaaagcttgt ttgatttctt     2546
aaagttatta aacttgtaca tataccaaaa agaagctgtc ttggatttaa atctgtaaaa     2606
tcagatgaaa ttttactaca attgcttgtt aaaatatttt ataagtgatg ttccttttc      2666 accaagagta taaaccttt tagtgtgact gttaaaactt cctttttaaat caaaatgcca    2726 aatttattaa ggtggtggag ccactgcagt gttatctcaa aataagaata ttttgttgag    2786
atattccaga atttgtttat atggctggta acatgtaaaa tctatatcag caaaagggtc    2846
tacctttaaa ataagcaata acaaagaaga aaaccaaatt attgttcaaa tttaggttta     2906
aacttttgaa gcaaactttt ttttatcctt gtgcactgca ggcctggtac tcagattttg    2966
ctatgaggtt aatgaagtac aagctgtgc ttgaataacg atatgttttc tcagattttc     3026
tgttgtacag tttaatttag cagtccatat cacattgcaa aagtagcaat gacctcataa    3086
aatacctctt caaaatgctt aaattcattt cacacattaa ttttatctca gtcttgaagc    3146
caattcagta ggtgcattgg aatcaagcct ggctacctgc atgctgttcc ttttcttttc    3206
ttcttttagc cattttgcta agagacacag tcttctcatc acttcgtttc tcctatttg     3266 ttttactagt tttaagatca gagttcactt tcttttggact ctgcctatat tttcttacct   3326
gaacttttgc aagttttcag gtaaacctca gctcaggact gctatttagc tcctcttaag    3386
aagattaaaa gagaaaaaaa aaggcccttt taaaaatagt atacacttat tttaagtgaa    3446
aagcagagaa tttatttat agctaatttt agctatctgt aaccaagatg gatgcaaaga     3506
```

-continued

```
ggctagtgcc tcagagagaa ctgtacgggg tttgtgactg gaaaaagtta cgttcccatt   3566
ctaattaatg ccctttctta tttaaaaaca aaccaaatg atatctaagt agttctcagc    3626
aataataata atgacgataa tacttctttt ccacatctca ttgtcactga catttaatgg   3686
tactgtatat tacttaattt attgaagatt attatttatg tcttattagg acactatggt   3746
tataaactgt gtttaagcct acaatcattg attttttttt gttatgtcac aatcagtata   3806
ttttctttgg ggttacctct ctgaatatta tgtaaacaat ccaaagaaat gattgtatta   3866
agatttgtga ataaattttt agaaatctga ttggcatatt gagatattta aggttgaatg   3926
tttgtcctta ggataggcct atgtgctagc ccacaaagaa tattgtctca ttagcctgaa   3986
tgtgccataa gactgacctt ttaaaatgtt ttgagggatc tgtggatgct tcgttaattt   4046
gttcagccac aatttattga gaaaatattc tgtgtcaagc actgtgggtt ttaatatttt   4106
taaatcaaac gctgattaca gataatagta tttatataaa taattgaaaa aaattttctt   4166
ttgggaagag ggagaaaatg aaataaatat cattaaagat aactcaggag aatcttcttt   4226
acaattttac gtttagaatg tttaaggtta agaaagaaat agtcaatatg cttgtataaa   4286
acactgttca ctgtttttttt taaaaaaaaa acttgatttg ttattaacat tgatctgctg   4346
acaaaacctg ggaatttggg ttgtgtatgc gaatgtttca gtgcctcaga caaatgtgta   4406
tttaacttat gtaaaagata agtctggaaa taaatgtctg tttattttttg tactattta   4465
```

<210> SEQ ID NO 26
<211> LENGTH: 604
<212> TYPE: PRT
<213> ORGANISM: Homo sapiens

<400> SEQUENCE: 26

```
Met Leu Ala Arg Ala Leu Leu Cys Ala Val Leu Ala Leu Ser His
  1               5                  10                  15

Thr Ala Asn Pro Cys Cys Ser His Pro Cys Gln Asn Arg Gly Val Cys
             20                  25                  30

Met Ser Val Gly Phe Asp Gln Tyr Lys Cys Asp Cys Thr Arg Thr Gly
         35                  40                  45

Phe Tyr Gly Glu Asn Cys Ser Thr Pro Glu Phe Leu Thr Arg Ile Lys
     50                  55                  60

Leu Phe Leu Lys Pro Thr Pro Asn Thr Val His Tyr Ile Leu Thr His
 65                  70                  75                  80

Phe Lys Gly Phe Trp Asn Val Val Asn Asn Ile Pro Phe Leu Arg Asn
                 85                  90                  95

Ala Ile Met Ser Tyr Val Leu Thr Ser Arg Ser His Leu Ile Asp Ser
            100                 105                 110

Pro Pro Thr Tyr Asn Ala Asp Tyr Gly Tyr Lys Ser Trp Glu Ala Phe
        115                 120                 125

Ser Asn Leu Ser Tyr Tyr Thr Arg Ala Leu Pro Pro Val Pro Asp Asp
    130                 135                 140

Cys Pro Thr Pro Leu Gly Val Lys Gly Lys Lys Gln Leu Pro Asp Ser
145                 150                 155                 160

Asn Glu Ile Val Glu Lys Leu Leu Leu Arg Arg Lys Phe Ile Pro Asp
                165                 170                 175

Pro Gln Gly Ser Asn Met Met Phe Ala Phe Phe Ala Gln His Phe Thr
            180                 185                 190

His Gln Phe Phe Lys Thr Asp His Lys Arg Gly Pro Ala Phe Thr Asn
        195                 200                 205
```

```
Gly Leu Gly His Gly Val Asp Leu Asn His Ile Tyr Gly Glu Thr Leu
        210                 215                 220

Ala Arg Gln Arg Lys Leu Arg Leu Phe Lys Asp Gly Lys Met Lys Tyr
225                 230                 235                 240

Gln Ile Ile Asp Gly Glu Met Tyr Pro Pro Thr Val Lys Asp Thr Gln
                245                 250                 255

Ala Glu Met Ile Tyr Pro Pro Gln Val Pro Glu His Leu Arg Phe Ala
            260                 265                 270

Val Gly Gln Glu Val Phe Gly Leu Val Pro Gly Leu Met Met Tyr Ala
        275                 280                 285

Thr Ile Trp Leu Arg Glu His Asn Arg Val Cys Asp Val Leu Lys Gln
    290                 295                 300

Glu His Pro Glu Trp Gly Asp Glu Gln Leu Phe Gln Thr Ser Arg Leu
305                 310                 315                 320

Ile Leu Ile Gly Glu Thr Ile Lys Ile Val Ile Glu Asp Tyr Val Gln
                325                 330                 335

His Leu Ser Gly Tyr His Phe Lys Leu Lys Phe Asp Pro Glu Leu Leu
            340                 345                 350

Phe Asn Lys Gln Phe Gln Tyr Gln Asn Arg Ile Ala Ala Glu Phe Asn
        355                 360                 365

Thr Leu Tyr His Trp His Pro Leu Leu Pro Asp Thr Phe Gln Ile His
    370                 375                 380

Asp Gln Lys Tyr Asn Tyr Gln Gln Phe Ile Tyr Asn Asn Ser Ile Leu
385                 390                 395                 400

Leu Glu His Gly Ile Thr Gln Phe Val Glu Ser Phe Thr Arg Gln Ile
                405                 410                 415

Ala Gly Arg Val Ala Gly Gly Arg Asn Val Pro Pro Ala Val Gln Lys
            420                 425                 430

Val Ser Gln Ala Ser Ile Asp Gln Ser Arg Gln Met Lys Tyr Gln Ser
        435                 440                 445

Phe Asn Glu Tyr Arg Lys Arg Phe Met Leu Lys Pro Tyr Glu Ser Phe
    450                 455                 460

Glu Glu Leu Thr Gly Glu Lys Glu Met Ser Ala Glu Leu Glu Ala Leu
465                 470                 475                 480

Tyr Gly Asp Ile Asp Ala Val Glu Leu Tyr Pro Ala Leu Leu Val Glu
                485                 490                 495

Lys Pro Arg Pro Asp Ala Ile Phe Gly Glu Thr Met Val Glu Val Gly
            500                 505                 510

Ala Pro Phe Ser Leu Lys Gly Leu Met Gly Asn Val Ile Cys Ser Pro
        515                 520                 525

Ala Tyr Trp Lys Pro Ser Thr Phe Gly Gly Glu Val Gly Phe Gln Ile
    530                 535                 540

Ile Asn Thr Ala Ser Ile Gln Ser Leu Ile Cys Asn Asn Val Lys Gly
545                 550                 555                 560

Cys Pro Phe Thr Ser Phe Ser Val Pro Asp Pro Glu Leu Ile Lys Thr
                565                 570                 575

Val Thr Ile Asn Ala Ser Ser Ser Arg Ser Gly Leu Asp Asp Ile Asn
            580                 585                 590

Pro Thr Val Leu Leu Lys Glu Arg Ser Thr Glu Leu
        595                 600

<210> SEQ ID NO 27
<211> LENGTH: 21
<212> TYPE: DNA
```

```
<213> ORGANISM: Homo sapiens

<400> SEQUENCE: 27
gcggacccca ggggcgccca c                                              21

<210> SEQ ID NO 28
<211> LENGTH: 20
<212> TYPE: DNA
<213> ORGANISM: Homo sapiens

<400> SEQUENCE: 28
ccgaggctca tgaatccctg                                                20

<210> SEQ ID NO 29
<211> LENGTH: 20
<212> TYPE: DNA
<213> ORGANISM: Homo sapiens

<400> SEQUENCE: 29
ccgaggctca ggaagaagca                                                20

<210> SEQ ID NO 30
<211> LENGTH: 20
<212> TYPE: DNA
<213> ORGANISM: Homo sapiens

<400> SEQUENCE: 30
ctgaactcag tgaatccctg                                                20

<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
tacatttagg agccgggatg                                                20

<210> SEQ ID NO 32
<211> LENGTH: 20
<212> TYPE: DNA
<213> ORGANISM: Artificial Sequence
<220> FEATURE:
<223> OTHER INFORMATION: primer

<400> SEQUENCE: 32
tggtgctggc atggatagta                                                20

<210> SEQ ID NO 33
<211> LENGTH: 20
<212> TYPE: DNA
<213> ORGANISM: Artificial Sequence
<220> FEATURE:
<223> OTHER INFORMATION: primer

<400> SEQUENCE: 33
tacatttagg agccgggatg                                                20

<210> SEQ ID NO 34
<211> LENGTH: 20
<212> TYPE: DNA
<213> ORGANISM: Artificial Sequence
<220> FEATURE:
<223> OTHER INFORMATION: primer
```

```
<400> SEQUENCE: 34
gcatctggca actgcttctt                                              20

<210> SEQ ID NO 35
<211> LENGTH: 20
<212> TYPE: DNA
<213> ORGANISM: Artificial Sequence
<220> FEATURE:
<223> OTHER INFORMATION: primer

<400> SEQUENCE: 35
gccatggagt tcaaccatct                                              20

<210> SEQ ID NO 36
<211> LENGTH: 20
<212> TYPE: DNA
<213> ORGANISM: Artificial Sequence
<220> FEATURE:
<223> OTHER INFORMATION: primer

<400> SEQUENCE: 36
atctcccgag actccctgat                                              20

<210> SEQ ID NO 37
<211> LENGTH: 20
<212> TYPE: DNA
<213> ORGANISM: Artificial Sequence
<220> FEATURE:
<223> OTHER INFORMATION: primer

<400> SEQUENCE: 37
tacatttagg agccgggatg                                              20

<210> SEQ ID NO 38
<211> LENGTH: 20
<212> TYPE: DNA
<213> ORGANISM: Artificial Sequence
<220> FEATURE:
<223> OTHER INFORMATION: primer

<400> SEQUENCE: 38
tggtgctggc atggatagta                                              20
```

HUMAN COX-1 ALTERNATIVELY SPLICED VARIANTS AND METHODS OF USING SAME

FIELD OF THE INVENTION

This invention relates generally to molecular medicine and, more specifically, to alternatively spliced human cyclooxygenase-1 (COX-1).

BACKGROUND INFORMATION

Aspirin has been in use for over 100 years. The mechanism of action of this common drug was not fully appreciated until 1971 when it was discovered that the ability of aspirin to suppress inflammation lies primarily in its ability to inhibit the cyclooxygenase (COX) enzyme. Subsequently, two cyclooxygenase isoforms have been identified, designated as COX-1 and COX-2. The COX enzymes catalyze conversion of arachidonic acid to prostaglandin $G_2$ ($PGG_2$) and prostaglandin $H_2$ ($PGH_2$); (see FIG. 1). $PGH_2$ is then converted to a variety of prostaglandins and other eicosanoids that play a role in inflammation and other disease processes. Aspirin inhibits the action of COX-1 and COX-2 and thereby reduces prostaglandin and other eicosanoid levels and acts as an anti-inflammatory agent.

Prostaglandins (PG) are oxygenated fatty acids that bind to G-protein coupled receptors (GPCRs). Several naturally occurring prostaglandins, $PGD_2$, $PGE_2$, $PGF_{2\alpha}$, and $PGI_2$, have been identified. Prostaglandins produce numerous physiologic and pathophysiologic effects and regulate cellular processes in nearly every tissue. The wide spectrum of prostaglandin action includes effects on immune, endocrine, cardiovascular, renal and reproductive systems as well as the contraction and relaxation of smooth muscle. Accordingly, drugs that effect prostaglandin production such as aspirin and other non-steroidal anti-inflammatory drugs (NSAIDs) have been used to prevent or alleviate a variety of conditions including, for example, cardiovascular disease, discomfort associated with minor injuries and headaches, and of severe pain caused by a variety of inflammatory and degenerative joint diseases.

Given the broad role of prostaglandins in normal human physiology, it is not surprising that systemic suppression of prostaglandin synthesis through inhibition of the COX enzymes can lead to unwanted side effects. In particular, individuals taking NSAIDs for even short periods of time can experience gastrointestinal and renal side effects, in addition to effects on other physiological systems. As many as 25% of individuals using NSAIDs experience some type of side effect, and as many as 5% develop serous health consequences such as gastric bleeding, ulceration, or perforation.

While COX-1 and COX-2 carry out essentially the same catalytic reaction and have similar primary protein structures, the expression patterns of these isoforms are distinct. In general, COX-1 is expressed constitutively in nearly all normal tissues, while COX-2 is expressed at low to undetectable levels in normal tissues but is induced in certain circumstances such as in response to injury or inflammation. Recently, drugs that selectively inhibit COX-2 (coxibs) have been proposed as a safer alternative to traditional NSAIDs. Although some of these selective inhibitors of COX-2 have demonstrated better gastrointestinal safety compared to traditional non-selective NSAIDs, questions remain regarding their effects on renal and cardiovascular systems. In addition, selective inhibitors of COX-2 do not appear to have the protective cardiovascular effect observed with traditional NSAIDs such as aspirin.

A goal of clinical pharmacology and the pharmaceutical industry is the development of more selective drugs with greater efficacy and fewer side effects than those currently in use. In order to more effectively treat conditions where COX-1 modulators can be of benefit, such as inflamation and cardiovascular disease, COX-1 modulatory drugs with greater selectivity must be discovered. New COX-1 variants, such as alternatively spliced COX-1 polypeptides, can be more closely associated with a disease such as cardiovascular disease than the known COX-1 isoform and, thus, can be novel targets for drug discovery efforts, resulting in the discovery of drugs with greater efficacy or fewer side effects than drugs developed against the known COX-1 isoform.

Thus, there exists a need for the discovery of new COX-1 variants which can be used, for example, to design more specific drugs with fewer side effects. The present invention satisfies this need and provides related advantages as well.

SUMMARY OF THE INVENTION

The invention provides an isolated polypeptide containing the amino acid sequence of SEQ ID NO: 14, 16, 18, 20, 22 or 24. The invention also provides an isolated polypeptide containing a) an amino acid sequence having at least 50% amino acid identity with SEQ ID NO: 10, and b) an amino acid sequence selected from SEQ ID NOS: 14, 16, 18, 20, 22 or 24; or a conservative variant thereof. The invention further provides an isolated polypeptide containing the amino acid sequence of SEQ ID NO: 2, 4, 6, or 8. The invention also provides a method for identifying a compound that modulates a COX-1 variant by contacting an isolated COX-1 variant or a COX-1 variant over-expressed in a genetically engineered cell with a compound and determining the level of an indicator which correlates with modulation of a COX-1 variant, where an alteration in the level of the indicator as compared to a control level indicates that the compound is a compound that modulates the COX-1 variant.

BRIEF DESCRIPTION OF THE DRAWINGS

FIG. 2 shows the nucleotide sequence of human COX-1 variant ALT-1 (SEQ ID NO: 1). The underlined sequence indicates a nucleotide sequence which is not present in the known wild-type COX-1 enzyme (SEQ ID NO: 9). The start and stop codons for COX-1 variant ALT-1 are indicated in bolded capital letters.

FIG. 3 shows the nucleotide sequence of human COX-1 variant ALT-2 (SEQ ID NO: 3). The underlined sequence indicates a nucleotide sequence which is not present in known wild-type COX-1 enzyme (SEQ ID NO: 4). The start and stop codons for COX-1 variant ALT-2 are indicated in bolded capital letters.

FIG. 4 shows the nucleotide sequence of human COX-1 variant ALT-3 (SEQ ID NO: 5). The underlined sequence indicates a nucleotide sequence which is not present in the known wild-type COX-1 enzyme (SEQ ID NO: 9). The start and stop codons for COX-1 variant ALT-3 are indicated in bolded capital letters.

FIG. 5 shows the nucleotide sequence of human COX-1 variant ALT-4 (SEQ ID NO: 7). The underlined sequence indicates a nucleotide sequence which is not present in the known wild-type COX-1 enzyme (SEQ ID NO: 9). The start and stop codons for COX-1 variant ALT-4 are indicated in bolded capital letters. The italicized letters indicate a novel nucleotide sequence derived from Exon B as shown in FIG. 7.

FIG. 6 shows a comparison of the amino acid sequences of the known wild-type human COX-1 enzyme (SEQ ID NO: 10), abbreviated as COX-1 WT, with human COX-1 variants ALT-1 (SEQ ID NO: 2), ALT-2 (SEQ ID NO: 4), ALT-3 (SEQ ID NO: 6), and ALT-4 (SEQ ID NO: 8). The first arrow in the amino terminal area of the polypeptides indicates the location where the wild-type human COX-1 enzyme and the COX-1 variants ALT-1, ALT-3 and ALT-4 begin to coincide and the second arrow indicates the location where the wild-type human COX-1 enzyme and COX-1 variant ALT-2 begin to co-incide.

DETAILED DESCRIPTION OF THE INVENTION

The present invention is directed to the exciting discovery of several novel COX-1 variants. Such COX-1 variants can be used to determine and refine the specificity of compounds that bind and modulate the known wild-type COX-1 enzyme. These COX-1 variants also can be used to identify a compound that differentially modulates or binds to a first COX-1 variant in relation to a second COX-1 variant, wild-type COX-1 enzyme, or wild-type COX-2 enzyme. Such a compound can be, for example, a compound that specifically binds to a novel COX-1 variant described herein.

As disclosed herein in Example I, several novel COX-1 variants were identified using the reverse transcription polymerase chain reaction (RT-PCR) and the following COX-1 primers: GGTTCTTGCTGTTCCTGCTC (SEQ ID NO: 11) and TCACACTGGTAGCGGTCAAG (SEQ ID NO: 12). In particular, four novel alternatively spliced human COX-1 variants, designated herein COX-1 variant ALT-1, COX-1 variant ALT-2, COX-1 variant ALT-3, and COX-1 variant ALT-4, were identified as distinct from the wild-type human COX-1 enzyme (see FIGS. 2–6).

Figure 1:
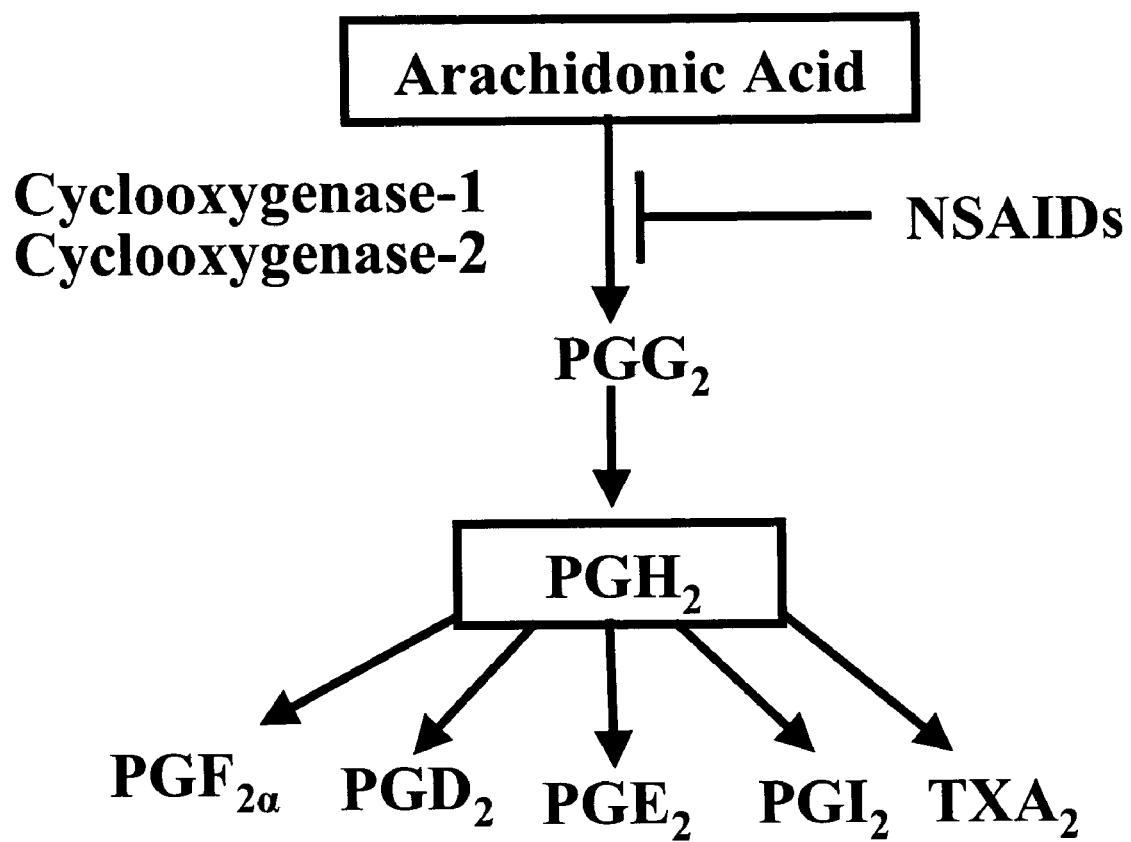
FIG. 1 shows a schematic diagram of the conversion of arachidonic acid to prostaglandins and other eicosanoids by the cyclooxygenase enzymes. The following abbreviations are used in FIG. 1: NSAID: non-steroidal anti-inflammatory drug, $PGG_2$: prostaglandin $G_2$, $PGH_2$: prostaglandin $H_2$, $PGF_2\alpha$: prostaglandin $F_2$ alpha, $PGD_2$: prostaglandin $D_2$, $PGE_2$: prostaglandin $E_2$, $PGI_2$: prostaglandin $I_2$, $TXA_2$: thromboxane $A_2$.
Figure 7:
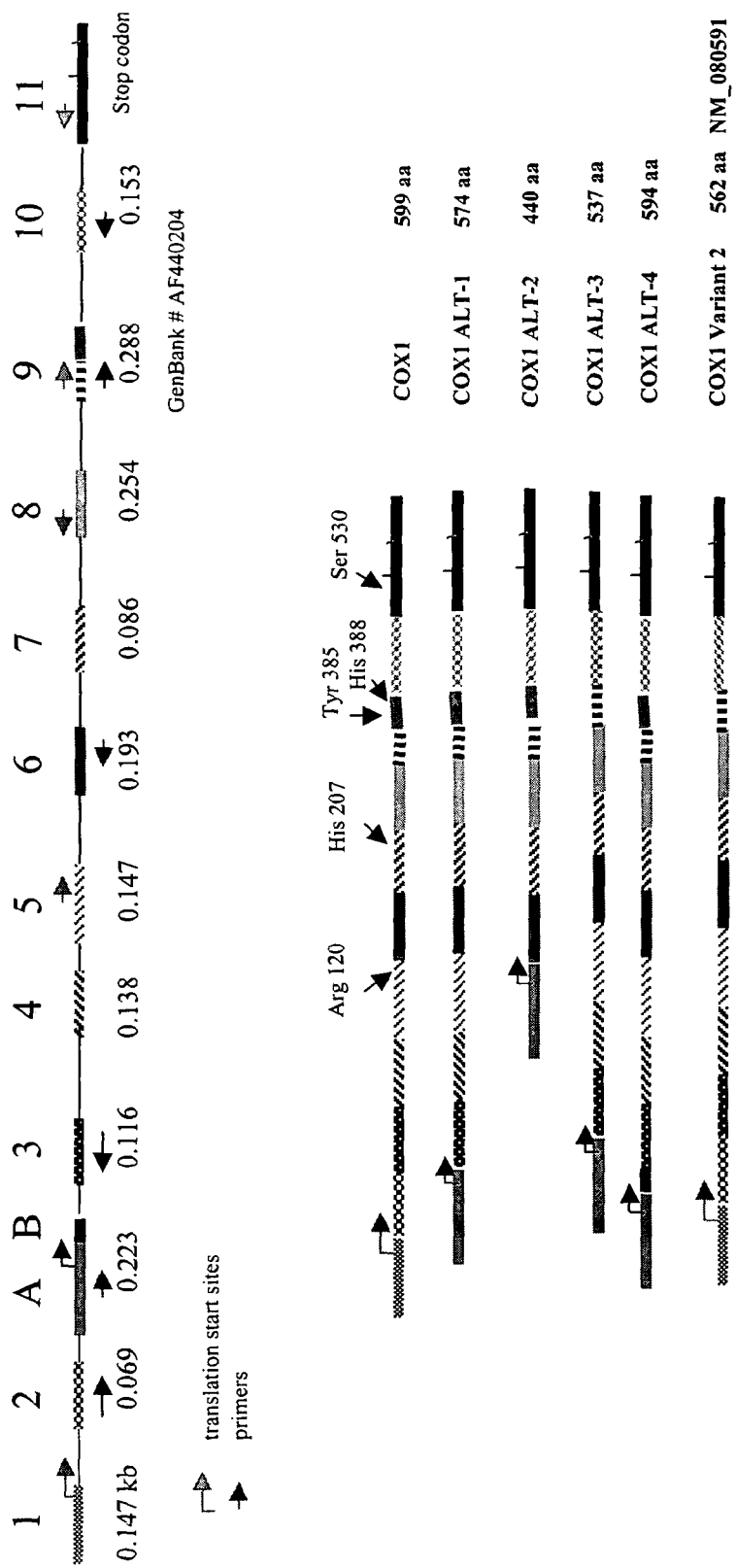
FIG. 7 shows the intron/exon structure of the human COX-1 genomic DNA clone AF440204. The figure schematically indicates which exons are found in COX-1 variants ALT-1 through ALT-4. Arg-120 is located at the opening of the hydrophobic fatty acid binding channel and is the counterion for the carboxylate group of arachidonate. His-388 and His-207 are the proximal and distal heme ligands, respectively. Tyr-385 neighbors the heme group and bound arachidonate and is likely the residue that is converted to a tyrosyl radical and abstracts the (13-pro-S)-hydrogen from arachidonate, thereby initiating cyclooxygenase catalysis. Ser-530 is the site of aspirin acetylation.

As further disclosed herein, sequence analysis of nucleic acid molecules encoding the alternatively spliced COX-1 variants revealed novel amino-terminal amino acid sequences. The amino acid sequences of the wild-type human COX-1 enzyme and the alternatively spliced COX-1 variants are shown in FIG. 6. Comparison of the known wild-type human COX-1 enzyme amino acid sequence (SEQ ID NO: 10) to the alternatively spliced human COX-1 variants identified herein revealed the novel amino acid sequence MRKPRLM (SEQ ID NO: 14) at the amino-terminus of COX-1 variants ALT-1 and ALT-3. As shown in FIG. 7, the start site of COX-1 variants ALT-1 and ALT-3 start sites are located within a newly identified alternatively spliced exon (labeled "A" in FIG. 7) which resides between exon 2 and exon 3 in the wild-type COX-1 enzyme sequence. The amino acid sequence at the junction of newly identified alternatively spliced exon A and exon 3 of the wild-type sequence is KPRLMNPCC (SEQ ID NO: 20), where the first five amino acids are encoded by the alternatively spliced exon A and the remaining four amino acids are residues derived from exon 3 (see FIGS. 6 and 7). As shown in FIGS. 6 and 7, the COX-1 variant ALT-3 differs from COX-1 variant ALT-1 by lacking part of exon 9.

As disclosed herein, the nucleotide sequence of COX-1 variant ALT-2 also contains alternatively spliced exon A (see FIG. 7). In COX-1 variant ALT-2, exon A is spliced to exon 6 of the wild-type human COX-1 sequence whereas in COX-1 variants ALT-1 and COX-1 variant ALT-3, exon A is spliced to exon 3. The start site of COX-1 variant ALT-2 is located in exon A, resulting in the unique amino-terminal sequence MRKPRLR (SEQ ID NO: 18). The amino acid sequence at the junction of newly identified alternatively spliced exon A and exon 6 of the wild-type sequence is KPRLRKKQL (SEQ ID NO: 24), where the first five amino acids are encoded by the alternatively spliced exon A and the remaining four amino acids are derived from exon 6 (see FIGS. 6 and 7).

As further disclosed herein, the nucleotide sequence of COX-1 variant ALT-4 also contains alternatively spliced exon A. In addition, COX-1 variant ALT-4 contains a newly identified alternatively spliced exon (labeled "B" in FIG. 7) which resides 3' to exon A in COX-1 variant ALT-4 and 5' to exon 3 in the wild-type COX-1 enzyme sequence. The start site of COX-1 variant ALT-4 is located in exon A. The inclusion of exon B in COX-1 variant ALT-4 results in an amino-terminal sequence of MRKPRLSRCHDSPSSQNTWWAQDLNSV (SEQ ID NO: 16). The amino acid sequence at the junction between newly identified alternatively spliced exon B and exon 3 of the wild-type sequence is DLNSVNPCC (SEQ ID NO: 22), where the first five amino acids are encoded by the alternatively spliced exon B and the remaining four amino acids are residues derived from exon 3 (see FIGS. 6 and 7).

Figure 8:
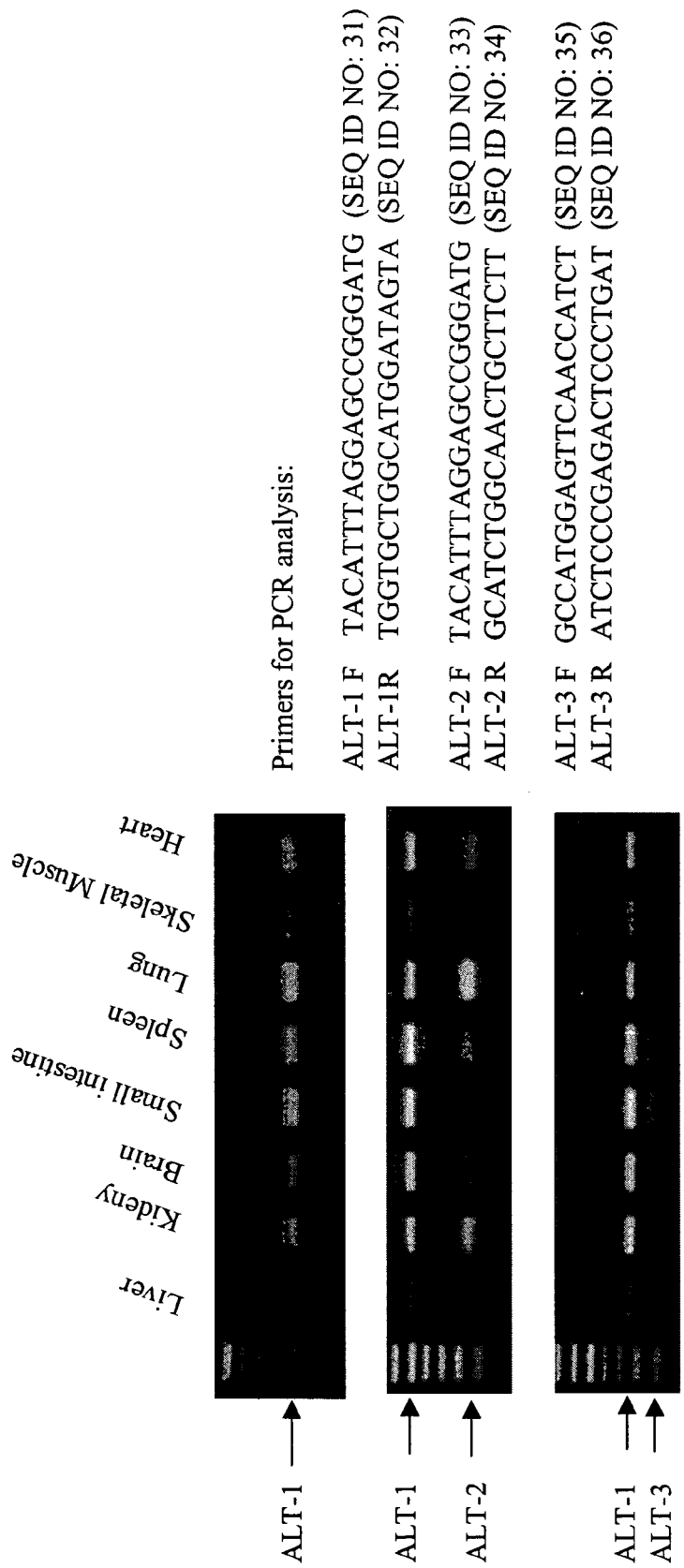
FIG. 8 shows distribution of mRNA from COX-1 variants ALT-1 through ALT-3 in various tissues using a reverse transcriptase-polymerase chain reaction RT-PCR procedure. The location of PCR products of the correct size for COX-1 variants ALT-1 through ALT-3 is indicated by an arrow. Sequences of primers used for PCR analysis are shown.

As further disclosed herein, expression of alternatively spliced human COX-1 variants ALT-1 through ALT-3 can be found in a variety of tissues including liver, kidney, brain, small intestine, spleen, lung, skeletal muscle, and heart (see FIG. 8 and Example III). In particular, COX-1 variant ALT-1 mRNA was expressed in all of the tissue types examined. COX-1 variant ALT-2 was expressed at various levels in the tissues examined, with low to undetectable levels found in skeletal muscle. COX-1 variant ALT-3 also was expressed at various levels in the tissues examined, with low to undetectable levels found in liver, lung, skeletal muscle and heart.

Figure 9:
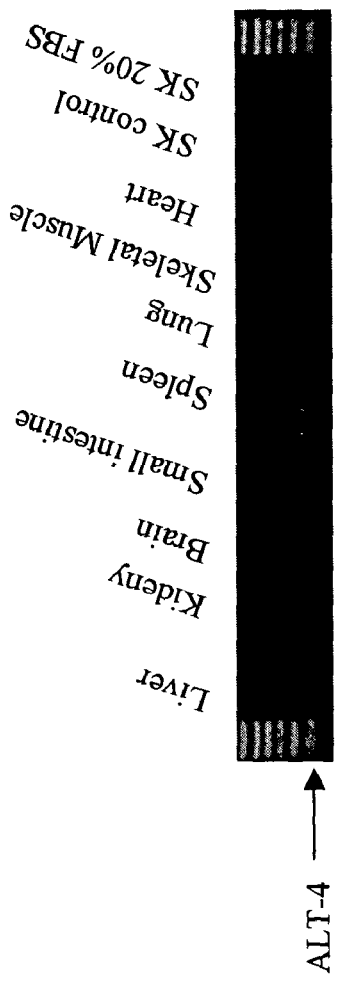
FIG. 9 shows distribution of mRNA from COX-1 variant ALT-4 in various tissues using an RT-PCR procedure. The expression of COX-1 variant ALT-4 mRNA in the neuronal cell line SK-N-SH (SK control) and in SK-N-SH cells cultured with 20% fetal bovine serum (SK 20% FBS) is also shown. The location of a PCR product of the correct size for COX-1 variant ALT-4 is indicated by an arrow. Sequences of primers used for PCR analysis are shown.
Figure 10:
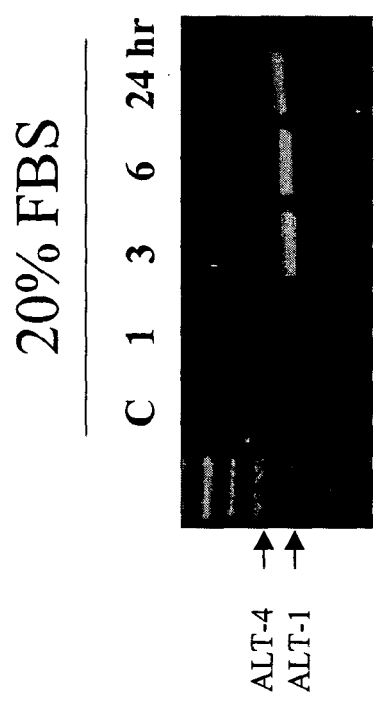
FIG. 10 shows induction of COX-1 variants ALT-1 and ALT-4 mRNA expression in SK-N-SH cells in response to culturing cells with 20% fetal bovine serum (FBS) for varying number of hours. C=control. The primers used in this experiment are identical to those listed in FIGS. 8 and 9.

As shown in FIG. 9, human COX-1 variant ALT-4 mRNA was expressed at various levels in different tissues, with low to undetectable levels found in liver, brain, small intestine, skeletal muscle and heart. In addition, COX-1 variant ALT-4 mRNA was present in low to undetectable levels in the neuronal cell line SK-N-SH, but was induced by 20% fetal bovine serum treatment of these cells (see FIGS. 9 and 10). Induction of COX-1 variant ALT-4 mRNA in SK-N-SH cells was observed by three hours post induction (see FIG. 10). In addition, as shown in FIG. 10, COX-1 variant ALT-1 mRNA is increased in response to 20% fetal bovine serum treatment of SK-N-SH cells.

Based on these discoveries, the present invention provides novel alternatively spliced COX-1 variants and screening methods that rely on these variants. In particular, the invention provides an isolated polypeptide containing an amino acid sequence of SEQ ID NOS: 14, 16, 18, 20, 22 or 24, which represent the unique amino-terminal and junctional portions of newly identified COX-1 variants ALT-1, ALT-2, ALT-3 and ALT-4. The present invention further provides an isolated polypeptide containing an amino acid sequence having at least 50% amino acid identity with SEQ ID NO: 10 and also containing the amino acid sequence of SEQ ID NOS: 14, 16, 18, 20, 22, or 24; or a conservative variant thereof. Also provided herein is an isolated polypeptide containing the amino acid sequence of SEQ ID NO: 2, 4, 6 or 8. Further provided herein is an isolated polypeptide consisting of the amino acid sequence of SEQ ID NO: 2, 4, 6 or 8; or a conservative variant thereof. In one embodiment, the invention provides an isolated polypeptide consisting of the amino acid sequence of SEQ ID NO: 2, 4, 6 or 8.

The present invention further provides a method for identifying a compound that modulates a COX-1 variant by contacting an isolated COX-1 variant or a COX-1 variant over-expressed in a genetically engineered cell with a compound and determining the level of an indicator which correlates with modulation of the COX-1 variant, where an alteration in the level of the indicator as compared to a control level indicates that the compound is a compound that modulates the COX-1 variant. The present invention also provides a method for identifying a compound that specifically binds to a COX-1 variant by contacting an isolated COX-1 variant or a COX-1 variant over-expressed in a genetically engineered cell with a compound and determining specific binding of the compound to the COX-1 variant.

The invention additionally provides a method for identifying a compound that differentially modulates a COX-1 variant by a) contacting an isolated COX-1 variant or a COX-1 variant over-expressed in a genetically engineered cell with a compound; b) determining the level of an indicator which correlates with modulation of the COX-1 variant; c) contacting a second COX enzyme with the compound; d) determining the level of a corresponding indicator which correlates with modulation of the second COX enzyme; and e) comparing the level of the indicator from step (b) with the level of the corresponding indicator from step (d), where a different level of the indicator from step (b) compared to the level of the corresponding indicator from step (d) indicates that the compound is a compound that differentially modulates the COX-1 variant.

Further provided herein is a method for identifying a compound that differentially binds to a COX-1 variant by a) contacting an isolated COX-1 variant or a COX-1 variant over-expressed in a genetically engineered cell with a compound; b) determining specific binding of the compound to the COX-1 variant; c) contacting a second COX enzyme with the compound; d) determining specific binding of the compound to the second COX enzyme; and e) comparing the level of specific binding from step (b) with the level of specific binding from step (d), where a different level of specific binding from step (b) compared to the level of specific binding from step (d) indicates that the compound is a compound that differentially binds to the COX-1 variant.

The methods of the invention can be useful for designing drugs that bind to or modulate a wild-type COX-1 such as human COX-1 (SEQ ID NO: 10) in preference to one or more of the disclosed alternatively spliced COX-1 variants, or for identifying compounds that bind to or modulate one or more COX-1 variants in preference to other known COX-1 variants or either or both of the wild-type COX-1 or COX-2 enzymes. Compounds identified by a method of the invention can be therapeutically useful in preventing or reducing the severity of any of a variety of a conditions where modulation of the COX-1 enzyme or a COX-1 variant is beneficial.

As discussed above, the present invention relates to novel, alternatively spliced COX-1 variants. The COX-1 enzyme is a membrane-bound, heme-containing, homodimer of two 70-kD polypeptides that catalyzes the first two steps in prostaglandin, thromboxane and prostacyclin synthesis (Needleman et al., *Annu. Rev. Biochem.* 55:69–102 (1986)). Specifically, COX-1 catalyzes two separate reactions; the first being the addition of molecular oxygen to arachidonic acid to form PGG (cyclooxygenase reaction), and the second being the further conversion of $PGG_2$ to the more stable $PGH_2$ by a peroxidase reaction (Yokoyama and Tanabe, *Biochem. Biophys. Res. Commun.* 165:888–894 (1989); and Hla, *Prostaglandins* 51:81–85 (1996)). The peroxidase activity of COX-1 catalyzes oxidation of a broad range of substrates. Inhibition of COX-1 cyclooxygenase activity is responsible for decreased levels of prostaglandins and eicosinoids.

The COX-1 enzyme, also called prostaglandin H synthase (PGHS), prostaglandin G/H synthase (PTGS1), or prostaglandin-endoperoxide synthase 1, was first cloned by Needleman's group (Merlie et al., *J. Biol. Chem.* 263:3550–3553 (1988)) and DeWitt and Smith (DeWitt and Smith, *Proc. Natl. Acad. Sci. USA* 85:1412–1416 (1988)). COX-1 has also been cloned from mouse (DeWitt et al., *J. Biol. Chem.* 265:5192–2198 (1990)), human (Funk et al., *FASEB J.* 5:2304–2312 (1991)), avian (Xie et al., *Proc. Natl. Acad. Sci. USA* 88:2692–2696 (1991)) and rat (Feng et al., *Arch. Biochem. Biophys.* 307:361–368 (1993)).

An alternatively spliced form of the human COX-1 gene lacking part of exon 9 has been reported (Diaz, *J. Biol. Chem.* 267:10616–10822 (1992)). This form of COX-1 has been designated PTGS1 transcript variant 2 or COX-1 variant 2 (GenBank Accession No. NM_080591). COX-1 variant 2 contains the same amino-terminal and carboxy-terminal sequences as the wild-type human COX-1 enzyme (SEQ ID NO: 10; GenBank Accession No. NM_000962) but lacks the same part of exon 9 that is missing in COX-1 variant ALT-3 (SEQ ID NO: 6) disclosed herein. As described above, COX-1 variant ALT-3 contains a unique amino-terminal region (SEQ. ID NO: 14) as compared to the wild-type human COX-1 enzyme (SEQ ID NO: 10) and known COX-1 variant 2.

Alternatively spliced forms of the COX-1 gene have also been identified in various species. For example, a form of the rat COX-1 lacking codons 1–36 has been described (Kitzler et al., *Arch. Biochem. and Biophy.* 316:856–863 (1995); Vogiagis et al., *Am. J. Physiol. Gastrointest. Liver Physiol.* 278:G820–G827 (2000); Vogiagis et al., *Carcinogenesis* 22:869–874 (2001)). In addition, three alternatively spliced forms of the canine COX-1 gene have been described (Chandrasekharan et al., *Proc. Natl. Acad. Sci. USA* 21:13926–13931 (2002)). Two of the canine variants retain intron 1 of the COX-1 gene while the third variant does not contain intron 1 and lacks exons 5–8 (Chandrasekharan et al., supra, 2002).

COX-1 has been found in nearly all tissues under basal conditions (Crofford, *J. Rheum.* 24:15–19). Consistent with this broad pattern of expression pattern, one function of COX-1 is to provide prostaglandin precursors for homeostatic regulation in a variety of tissues. A second function of COX-1 is to provide precursors for thromboxane synthesis in blood platelets, (Schafer, *J. Clin. Pharmacol.* 35:209–219). Platelets, which do not have nuclei, cannot produce an inducible enzyme in response to activating conditions. In the presence of an NSAID such as aspirin, platelets are prevented from generating thromboxane during activation and fail to complete successful aggregation, inhibiting their thrombogenic potential. In the adjacent vascular endothelium, prostaglandins and eicosanoids play a different role. The release of eicosanoids by activated platelets may provide both a substrate and stimulus for the generation of prostacyclin ($PGI_2$) by the endothelium. This compound stimulates vasodilatation, counteracting the vasoconstrictor, thromboxane. Prostacyclin formation is a function of COX-2 (Hennan et al., *Circulation* 104:820–825 (2001)).

Because prostacyclin antagonizes the platelet aggregation mediated by thromboxane, selective COX-2 inhibitors can suppress prostacyclin formation without concomitant inhibition of thromboxane, thereby resulting in an increased risk of thrombosis. As an example, a significant increase in thrombotic cardiovascular events was noted in humans treated with rofecoxib, a selective COX-2 inhibitor, in comparison with patients receiving naproxen, a non-selective NSAID (Fitzgerald et al., *Clin. Exp. Rheumatol.* 19 (Suppl 25):S31–S36 (2001)).

COX-1 also functions in other physiological systems where it can lead to vasodilatation in the presence of contractile conditions. For example, in both the kidney and the stomach, normal physiological stimuli are associated with dramatic changes in blood flow. During times of lowered blood volume, the kidney releases angiotensin and other factors to maintain blood pressure by systemic vasoconstriction (Palmer and Henrich, *Semin. Nephrol.* 15:214–227 (1995)). At the same time, angiotensin provokes prostaglandin synthesis in the kidney. COX-1 is expressed in the vasculature, glomeruli, and collecting ducts of the kidney, where it is involved in producing vasodilating prostaglandins, which maintain renal plasma flow and glomerular filtration rate during conditions of systemic vasoconstriction. In the presence of NSAIDs, this protective response can fail, leading to renal ischemia and damage in susceptible individuals (Zambraski, *Semin. Neohrol.* 15:205–213 (1995)). Similarly, in the gastric antrum, NSAID use can lead to ischemia and ultimately mucosal damage and ulceration (Trevethick et al., *Gen. Pharmacol.* 26:1455–1459 (1995)). The enzyme blocked by NSAIDs is thought to be COX-1 (Wallace, *Gastroenterology* 112:1000–1016 (1997)) that-produces prostaglandins, which alter blood flow in the microcirculation of the gastric mucosa.

COX-1 also may play a role in the human eye, where the iris is the major site for producing prostaglandins. In the eye, prostaglandins regulate smooth muscle contraction, blood-aqueous barrier penetration and intraocular pressure (Matsuo and Cynader, *Br. J. Ophthalmol.* 77:110–114 (1993)). Using immunoprecipitation, constitutive COX-1 expression was detected in human iris homogenates, whereas COX-2 was only detected after stimulation with lipopolysaccharide (Van Haeringen et al., *J. Ocul. Pharmacol Ther.* 16:353–361 (2000)). Furthermore, the NSAID S(+)flurbiprofen inhibits COX-1 70-fold more potently in human iris than in human blood (Haeringen et al., supra, 2000). Such a difference could be due, for example, to an alternatively spliced form of COX-1 in human iris or in whole blood. Such alternatively spliced forms of COX-1 can include an isolated polypeptide of the invention, for example, one of the COX-1 variants ALT-1, ALT-2, ALT-3, or ALT-4 disclosed herein.

The invention provides novel COX-1 variants which are alternatively spliced forms of the wild-type COX-1 enzyme. In one embodiment, the invention provides an isolated polypeptide containing the amino acid sequence of SEQ ID NOS: 14, 16, 18, 20, 22 or 24. In another embodiment, the invention provides an isolated polypeptide containing an amino acid sequence having at least 50% amino acid identity with SEQ ID NO: 10 and further containing the amino acid sequence of SEQ ID NOS: 14, 16, 18, 20, 22, or 24; or a conservative variant thereof. In a further embodiment, the invention provides an isolated polypeptide containing the amino acid sequence of SEQ ID NOS: 2, 4, 6 or 8. Further provided herein is an isolated polypeptide consisting of the amino acid sequence of SEQ ID NOS: 2, 4, 6 or 8, or a conservative variant thereof. In one embodiment, the invention provides an isolated polypeptide consisting of the amino acid sequence of SEQ ID NOS: 2, 4, 6 or 8.

The invention further provides a COX-1 variant binding agent which binds the amino acid sequence of SEQ ID NOS: 14, 16 or 18; or an epitope thereof. Such a COX-1 variant binding agent can be, without limitation, an antibody or antigen binding fragment thereof. The invention additionally provides a cell that includes an exogenously expressed polypeptide containing the amino acid sequence of SEQ ID NOS: 14, 16, 18, 20, 22 or 24; a cell which includes an exogenously expressed polypeptide containing an amino acid sequence having at least 50% amino acid identity with SEQ ID NO: 10 and further containing the amino acid sequence of SEQ ID NOS: 14, 16, 18, 20, 22, or 24; or a conservative variant thereof; and a cell which includes an exogenously expressed polypeptide containing the amino acid sequence of SEQ ID NOS: 2, 4, 6 or 8. Further provided herein is an isolated polypeptide consisting of the amino acid sequence of SEQ ID NOS: 2, 4, 6 or 8 or a conservative variant thereof. In one embodiment, the invention provides an isolated polypeptide consisting of the amino acid sequence of SEQ ID NOS: 2, 4, 6 or 8.

The present invention also provides a method for identifying a compound that modulates a COX-1 variant by contacting an isolated COX-1 variant or a COX-1 variant over-expressed in a genetically engineered cell with a compound and determining the level of an indicator which correlates with modulation of a COX-1 variant, where an alteration in the level of the indicator as compared to a control level indicates that the compound is a compound that modulates the COX-1 variant. The alteration can be, for example, an increase or decrease in the level of an indicator such as, without limitation, a prostaglandin such as prostaglandin $E_2$ ($PGE_2$). A method of the invention can be practiced with any of a variety of COX-1 variants such as an isolated polypeptide containing an amino acid sequence having at least 50% amino acid identity with SEQ ID NO: 10 and further containing the amino acid sequence of SEQ ID NOS: 14, 16, 18, 20, 22, or 24; or a conservative variant thereof; an isolated polypeptide containing the amino acid sequence of SEQ ID NOS: 2, 4, 6 or 8; or an isolated polypeptide consisting of the amino acid sequence of SEQ ID NOS: 2, 4, 6 or 8. A method of the invention also can be practiced using any of a variety of COX-1 variants over-expressed or exogenously expressed in a genetically engineered cell. In one embodiment, the COX-1 variant is exogenously over-expressed in the genetically engineered cell. A variety of compounds can be screened according to the methods of the invention including, but not limited to, small molecules and polypeptides.

The present invention further provides a method for identifying a compound that specifically binds to a COX-1 variant by contacting an isolated COX-1 variant or a COX-1 variant over-expressed in a genetically engineered cell with a compound and determining specific binding of the compound to the COX-1 variant. In particular embodiments, a method of the invention is practiced using an isolated COX-1 variant such as a polypeptide containing an amino acid sequence having at least 50% amino acid identity with SEQ ID NO: 10 and further containing the amino acid sequence of SEQ ID NOS: 14, 16, 18, 20, 22, or 24; or a conservative variant thereof; an isolated COX-1 variant containing the amino acid sequence of SEQ ID NOS: 2, 4, 6 or 8; or an isolated COX-1 variant consisting of the amino acid sequence of SEQ ID NOS: 2, 4, 6 or 8. In another embodiment, a method of the invention is practiced using a COX-1 variant over-expressed or exogenously expressed in a genetically engineered cell, for example, a COX-1 variant exogenously over-expressed in a genetically engineered cell. In the methods of the invention, contacting can occur in vivo or in vitro, and the compounds to be screened can include, without limitation, small molecules and polypeptides.

The invention further provides a method for identifying a compound that differentially modulates a COX-1 variant by a) contacting an isolated COX-1 variant or a COX-1 variant over-expressed in a genetically engineered cell with a compound; b) determining the level of an indicator which correlates with modulation of a COX-1 variant; c) contacting a second COX enzyme with the compound; d) determining the level of a corresponding indicator which correlates with modulation of the second COX enzyme; and e) comparing the level of the indicator from step (b) with the level of the corresponding indicator from step (d), where a different level of the indicator from step (b) compared to the level of the corresponding indicator from step (d) indicates that the compound is a compound that differentially modulates the COX-1 variant. The COX enzyme can be, for example, a distinct COX-1 variant or a wild-type COX-1 or COX-2 from the same or a different species, or a functional fragment thereof. The human COX-2 nucleotide sequence (SEQ ID NO: 25) and amino acid sequence (SEQ ID NO: 26) can be found in GenBank at Accession No. NM_000963. The level of the indicator from step (b) can be greater or less than the level of the indicator from step (d) and the indicator can be, for example, prostaglandin $E_2$ ($PGE_2$). In particular embodiments, a method of the invention is practiced using an isolated COX-1 variant containing an amino acid sequence having at least 50% amino acid identity with SEQ ID NO: 10 and further containing the amino acid sequence of SEQ ID NOS: 14, 16, 18, 20, 22, or 24; or a conservative variant thereof; an isolated COX-1 variant containing the amino acid sequence of SEQ ID NOS: 2, 4, 6 or 8; or an isolated COX-1 variant consisting of the amino acid sequence of SEQ ID NOS: 2, 4, 6 or 8. In another embodiment, a method of the invention is practiced using a COX-1 variant over-expressed in a genetically engineered cell, for example, a COX-1 variant exogenously over-expressed or exogenously expressed in a genetically engineered cell. In the methods of the invention, the compounds to be screened can include, without limitation, small molecules and polypeptides.

The invention further provides a method for identifying a compound that differentially binds to a COX-1 variant by a) contacting an isolated COX-1 variant or a COX-1 variant over-expressed in a genetically engineered cell with a compound; b) determining specific binding of the compound to the COX-1 variant; c) contacting a second COX enzyme with the compound; d) determining specific binding of the compound to the second COX enzyme; and e) comparing the level of specific binding from step (b) with the level of specific binding from step (d), where a different level of specific binding from step (b) compared to the level of specific binding from step (d) indicates that the compound is a compound that differentially binds to the COX-1 variant. The second COX enzyme can be, for example, a distinct COX-1 variant or a wild-type COX-1 or COX-2 from the same or a different species, or a functional fragment thereof. The different level of specific binding can be an increased or decreased level of specific binding. In particular embodiments, a method of the invention is practiced using an isolated COX-1 variant containing an amino acid sequence having at least 50% amino acid identity with SEQ ID NO: 10 and further containing the amino acid sequence of SEQ ID NOS: 14, 16, 18, 20, 22, or 24; or a conservative variant thereof; an isolated COX-1 variant containing the amino acid sequence of SEQ ID NOS: 2, 4, 6 or 8; or an isolated COX-1 variant consisting of the amino acid sequence of SEQ ID NOS: 2, 4, 6 or 8. In another embodiment, a method of the invention is practiced using a COX-1 variant over-expressed in a genetically engineered cell, for example, a COX-1 variant exogenously over-expressed in a genetically engineered cell. In the methods of the invention, contacting can occur in vivo or in vitro. One skilled in the art understands that the compounds to be screened include, yet are not limited to, small molecules and polypeptides.

The invention also provides an isolated nucleic acid molecule having a nucleotide sequence that encodes a polypeptide containing an amino acid sequence having at least 50% amino acid identity with SEQ ID NO: 10 and further containing the amino acid sequence of SEQ ID NOS: 20, 22 or 24; or a conservative variant thereof. The invention further provides an isolated nucleic acid molecule containing a nucleotide sequence that encodes the amino acid sequence of SEQ ID NOS: 2, 4, 6 or 8. In addition, the invention provides an isolated nucleic acid molecule consisting of a nucleotide sequence of SEQ ID NOS: 1, 3, 5 or 7. The invention further provides a vector containing a nucleic acid molecule having a nucleotide sequence that encodes a polypeptide containing an amino acid sequence having at least 50% amino acid identity with SEQ ID NO: 10 and further containing the amino acid sequence of SEQ ID NOS: 20, 22 or 24; or a conservative variant thereof; a nucleic acid molecule containing a nucleotide sequence that encodes the amino acid sequence of SEQ ID NOS: 2, 4, 6 or 8; or a nucleic acid molecule consisting of the nucleotide sequence of SEQ ID NOS: 1, 3, 5 or 7. Host cells containing such a vector are further provided herein.

From the foregoing, it is clear that the present invention relates, in part, to the identification of novel COX-1 variants. As used herein, the term "COX-1 variant" means a polypeptide containing an amino acid sequence that has at least 30% amino acid identity with the wild-type human COX-1 enzyme SEQ ID NO: 10 and further containing the amino acid sequence of (SEQ ID NOS: 14, 16, 18, 20, 22, or 24; or a conservative variant thereof. As non-limiting examples, a COX-1 variant can contain an amino acid sequence having, for example, at least 30% amino acid identity, at least 40% amino acid identity, at least 50% amino acid identity, at least 60% amino acid identity, at least 70% amino acid identity, at least 80% amino acid identity, at least 90% amino acid identity, or at least 95% amino acid identity with the amino acid sequence of the wild-type human COX-1 enzyme (SEQ ID NO: 10). As a non-limiting example, a COX-1 variant can contain an amino acid sequence having at least 50% amino acid identity with SEQ ID NOS: 10 and further containing the amino acid sequence of SEQ ID NOS: 14, 16, 18, 20, 22, or 24; or a conservative variant thereof.

Based on the above, it is understood that species homologs of COX-1 variants that contain the amino acid sequence of SEQ ID NOS: 14, 16, 18, 20, 22, or 24; or a conservative variant thereof, are encompassed by the definition of COX-1 variant as used herein. As non-limiting examples, an isolated polypeptide containing the amino acid sequence of SEQ ID NOS: 2, 4, 6 or 8, or consisting of the amino acid sequence of SEQ ID NOS: 2, 4, 6 or 8 or a conservative variant thereof is a COX-1 variant of the invention.

A COX-1 variant differs from the known wild-type human COX-1 polypeptide by containing the amino acid sequence of SEQ ID NOS: 14, 16, 18, 20, 22, or 24; or a conservative variant thereof. As used herein in reference to a specified amino acid sequence such as SEQ ID NOS: 14, 16, 18, 20, 22 or 24, a "conservative variant" is a sequence in which one or more first amino acids are replaced by another amino acid or amino acid analog having at least one biochemical property similar to that of the first amino acid; similar properties include, yet are not limited to, similar size, charge, hydrophobicity or hydrogen-bonding capacity.

As an example, a conservative variant can be a sequence in which a first uncharged polar amino acid is conservatively substituted with a second (non-identical) uncharged polar amino acid such as cysteine, serine, threonine, tyrosine, glycine, glutamine or asparagine or an analog thereof. A conservative variant also can be a sequence in which a first basic amino acid is conservatively substituted with a second basic amino acid such as arginine, lysine, histidine, 5-hydroxylysine, N-methyllysine or an analog thereof. Similarly, a conservative variant can be a sequence in which a first hydrophobic amino acid is conservatively substituted with a second hydrophobic amino acid such as alanine, valine, leucine, isoleucine, proline, methionine, phenylalanine or tryptophan or an analog thereof. In the same way, a conservative variant can be a sequence in which a first acidic amino acid is conservatively substituted with a second acidic amino acid such as aspartic acid or glutamic acid or an analog thereof; a sequence in which an aromatic amino acid such as phenylalanine is conservatively substituted with a second aromatic amino acid or amino acid analog, for example, tyrosine; or a sequence in which a first relatively small amino acid such as alanine is substituted with a second relatively small amino acid or amino acid analog such as glycine or valine or an analog thereof. It is understood that a conservative variant of SEQ ID NOS: 14, 16, 18, 20, 22 or 24 can have one, two, three, four, five, six, seven, eight or more conservative amino acid substitutions relative to the specified sequence and that such a conservative variant can include naturally and non-naturally occurring amino acid analogs.

It is also understood that a fragment of a COX-1 variant containing the amino acid sequence of SEQ ID NOS: 14, 16, 18, 20, 22, or 24; or a conservative variant thereof, can be useful in a method of the invention. As non-limiting examples, a functional fragment of a COX-1 variant such as a heme-binding fragment or a fragment of a COX-1 variant that is involved in aspirin acetylation, such as a fragment containing Ser 530, can be useful in a method of the invention in place of the full-length COX-1 variant. Other fragments useful in the invention include, without limitation, fragments containing Arg 120, which is important for fatty acid and arylalkanoic acid COX inhibitors, and fragments containing Tyr 385, which forms the tyrosyl radical that initiates substrate oxygenation. As further understood by one skilled in the art, a COX-1 variant can optionally include non-homologous amino acid sequence. As non-limiting examples, a COX-1 variant can contain an epitope tag or can be fused to a non-homologous polypeptide such as gluthionine S-transferase.

As discussed above, the COX-1 variants ALT-1, ALT-2, ALT-3, and ALT-4 include an amino acid sequence that is not present in the wild-type COX-1 enzyme SEQ ID NO: 10 (see FIG. 6). For example, the alternatively spliced COX-1 variants ALT-1 and ALT-3 contain unique amino-terminal amino acid sequence disclosed herein as SEQ ID NO: 14, and the alternatively spliced COX-1 variant ALT-4 contains unique amino-terminal amino acid sequence disclosed herein as SEQ ID NO: 16 and the alternatively spliced COX-1 variant ALT-2 contains the unique amino-terminal amino acid sequences disclosed herein as SEQ ID NO: 18. Furthermore, a nine amino acid sequence spanning the junction between newly identified alternatively spliced exon A and exon 3 of the wild-type sequence is disclosed herein as KPRLMNPCC (SEQ ID NO: 20), where the first five amino acids are encoded by the alternatively spliced exon A and the remaining four amino acids are residues derived from exon 3 (see FIGS. 6 and 7). In addition, a nine amino acid sequence spanning the junction between newly identified alternatively spliced exon B and exon 3 is disclosed herein as DLNSVNPCC (SEQ ID NO: 22), where the first five amino acids are encoded by the alternatively spliced exon B and the remaining four amino acids are residues derived from exon 3 (see FIGS. 6 and 7). Further, a nine amino acid sequence spanning the invention between newly identified spliced exon A and exon 6 is disclosed herein as KPRLRKKL (SEQ ID NO: 24), where the first five amino acids are encoded by the alternatively spliced exon A and the remaining four amino acids are residues derived from exon 6. Thus, the invention provides an isolated polypeptide containing the amino acid sequence of SEQ ID NOS: 14, 16, 18, 20, 22 or 24. The invention further provides an isolated polypeptide containing an amino acid sequence having at least 50% amino acid identity with SEQ ID NO: 10 and further containing the amino acid sequence of SEQ ID NOS: 14, 16, 18, 20, 22, or 24; or a conservative variant thereof. As non-limiting examples, the invention provides an isolated polypeptide containing the amino acid sequence of SEQ ID NOS: 2, 6 or 8, or an isolated polypeptide consisting of the amino acid sequence of SEQ ID NOS: 2, 4, 6 or 8.

Further provided herein is an isolated polypeptide containing substantially the same amino acid sequence as SEQ ID NOS: 2, 4, 6 or 8, or consisting of substantially the same amino acid sequence as SEQ ID NOS: 2, 4, 6 or 8. The term "substantially the same," when used herein in reference to an amino acid sequence, means a polypeptide having a similar, non-identical sequence that is considered by those skilled in the art to be a functionally equivalent amino acid sequence. An amino acid sequence that is substantially the same as a reference amino acid sequence can have at least 70%, at least 80%, at least 90%, or at least 95% or more identity to the reference sequence. The term substantially the same also includes amino acid sequences encompassing, for example, modified forms of naturally occurring amino acids such as D-stereoisomers, non-naturally occurring amino acids, amino acid analogs and mimetics, so long as the polypeptide containing such a sequence retains a functional activity of the reference COX-1 variant. A functional activity of a COX-1 variant of the invention can be, without limitation, the ability to convert arachidonic acid to a prostaglandin such as prostaglandin $E_2$ ($PGE_2$), the ability to bind heme, or the ability to be acetylated by aspirin or inhibited by other NSAIDs.

It is understood that minor modifications in primary amino acid sequence can result in a polypeptide that has a substantially equivalent function as compared to a polypeptide of the invention. These modifications can be deliberate, as through site-directed mutagenesis, or may be accidental, produced, for example, through spontaneous mutation. For example, it is understood that only a portion of the entire primary structure of a COX-1 variant can be required in order to, for example, convert arachidonic acid to $PGE_2$ or another prostaglandin. Moreover, functional fragments of a COX-1 variant of the invention containing the amino acid sequence of SEQ ID NOS: 14, 16, 18, 20, 22, or 24; or a conservative variant thereof, similarly are included within the definition of substantially the same amino acid sequence; as set forth above, such functional fragments retain at least one biological function of the COX-1 variant. It is understood that various molecules can be attached to a COX-1 variant or other polypeptide of the invention. These molecules include, without limitation, heterologous polypeptides or peptides, carbohydrates, lipids, liposomes, phage or chemical moieties such as radioactive or fluorescent labels.

The invention further provides a COX-1 variant binding agent which binds the amino acid sequence of SEQ ID NOS: 14, 16 or 18, or an epitope thereof. As discussed above, SEQ ID NO: 14 represents the unique amino-terminal amino acid sequence of alternatively spliced COX-1 variants ALT-1 and ALT-3, SEQ ID NO: 16 represents the unique amino-terminal amino acid sequence of alternatively spliced COX-1 variant ALT-4 and SEQ ID NO: 18 represents the unique amino terminal amino acid sequences of alternatively spliced COX-1 variant ALT-2. A COX-1 variant binding agent of the invention can be, without limitation, an antibody or antigen binding fragment thereof which binds the amino acid sequence of SEQ ID NOS: 14, 16 or 18; or an epitope thereof.

As used herein, the term "COX-1 variant binding agent" means a molecule, such as a simple or complex organic molecule, carbohydrate, peptide, peptidomimetic, protein, glycoprotein, lipoprotein, lipid, nucleic acid molecule, antibody, aptamer or the like that specifically binds, competitively or non-competitively, the unique COX-1 variant amino-terminal amino acid sequence disclosed herein as SEQ ID NOS: 14, 16 or 18; or an epitope thereof. It is understood that such a binding agent does not specifically bind to a wild-type COX-1 such as SEQ ID NO: 10 since a wild-type COX-1 does not contain the unique amino-terminal amino acid sequence disclosed herein as SEQ ID NOS: 14, 16 or 18.

A COX-1 variant binding agent of the invention can be a polypeptide that specifically binds with high affinity or avidity to SEQ ID NOS: 14, 16 or 18, without substantial cross-reactivity to other unrelated sequences. The affinity of a COX-1 variant binding agent of the invention generally is greater than about $10^4$ $M^{-1}$ and can be greater than about $10^6$ $M^{-1}$. A COX-1 variant binding agent of the invention also can bind with high affinity such as an affinity greater than $10^4$ $M^{-1}$ to $10^{10}$ $M^{-1}$. Specific examples of binding agents of the invention include, but are not limited to, polyclonal and monoclonal antibodies that specifically bind an epitope within SEQ ID NOS: 14, 16 or 18; and nucleic acid molecules, nucleic acid analogs, and small organic molecules, identified, for example, by affinity screening of a nucleic acid or small molecule library against SEQ ID NOS: 14, 16 or 18, or an epitope thereof. For certain applications, a COX-1 variant binding agent that preferentially recognizes a particular conformational or post-translationally modified state of SEQ ID NOS: 14, 16 or 18 can be preferred. It is understood that a COX-1 variant binding agent of the invention can be labeled with a detectable moiety, if desired, or rendered detectable by specific binding to a detectable secondary agent.

In one embodiment, a COX-1 variant binding agent of the invention is an antibody or antigen-binding fragment thereof. As used herein, the term "antibody" is used in its broadest sense to mean a polyclonal or monoclonal antibody or an antigen-binding fragment of such an antibody. Such an antibody of the invention is characterized by having specific binding activity for SEQ ID NOS: 14, 16 or 18, or an epitope thereof, of at least about $1 \times 10^5$ $M^{-1}$. Thus, Fab, F(ab')$_2$, Fd and Fv fragments of an antibody, which retain specific binding activity for SEQ ID NOS: 14, 16 or 18, or an epitope thereof, are included within the definition of antibody as used herein. Specific binding activity can be readily determined by one skilled in the art, for example, by comparing the binding activity of the antibody to SEQ ID NOS: 14, 16 or 18, versus a control sequence. Methods of preparing polyclonal or monoclonal antibodies are well known to those skilled in the art. See, for example, Harlow and Lane, *Antibodies: A Laboratory Manual*, Cold Spring Harbor Laboratory Press (1988).

It is understood that the term antibody includes naturally occurring antibodies as well as non-naturally occurring antibodies such as, without limitation, single chain antibodies, chimeric, bi-functional and humanized antibodies, and antigen-binding fragments thereof. Such non-naturally occurring antibodies can be constructed using solid phase peptide synthesis, produced recombinantly or obtained, for example, by screening combinatorial libraries consisting of variable heavy chains and variable light chains as described in Huse et al., *Science* 246:1275–1281 (1989). These and other methods of making, for example, chimeric, humanized, CDR-grafted, single chain, and bi-functional antibodies are well known to those skilled in the art (Winter and Harris, *Immunol. Today* 14:243–246 (1993); Ward et al., *Nature* 341:544–546 (1989); Harlow and Lane, supra, 1988; Hilyard et al., *Protein Engineering: A practical approach* (IRL Press 1992); and Borrabeck, *Antibody Engineering*, 2d ed. (Oxford University Press 1995)).

An antibody of the invention can be prepared using as an antigen a polypeptide or peptide containing SEQ ID NOS: 14, 16 or 18, or an epitope thereof, which can be prepared, for example, from natural sources, produced recombinantly, or chemically synthesized. Such a polypeptide or peptide is a functional antigen if the polypeptide or peptide can be used to generate an antibody that specifically binds SEQ ID NOS: 14, 16 or 18, or an epitope thereof. As is well known in the art, a non-antigenic or weakly antigenic polypeptide or peptide can be made antigenic by coupling the polypeptide or peptide to a carrier molecule such as bovine serum albumin (BSA) or keyhole limpet hemocyanin (KLH). Various other carrier molecules and methods for coupling a polypeptide or peptide to a carrier molecule are well known in the art (see, for example, Harlow and Lane, supra, 1988). An antigenic polypeptide or peptide can also be generated by expressing the polypeptide or peptide as a fusion protein, for example, fused to glutathione S transferase, polyHis or the like. Methods for expressing polypeptide fusions are well known to those skilled in the art as described, for example, in Ausubel et al., *Current Protocols in Molecular Biology* (Supplement 47), John Wiley & Sons, New York (1999).

The present invention also provides a cell that includes an exogenously expressed polypeptide containing the amino acid sequence of SEQ ID NO: 14, 16, 18, 20, 22 or 24. Further provided herein is a cell that includes an exogenously expressed polypeptide containing an amino acid sequence having at least 50% amino acid identity with SEQ ID NO: 10 and further containing the amino acid sequence of SEQ ID NOS: 14, 16, 18, 20, 22, or 24; or a conservative variant thereof. The invention provides, for example, a cell that includes an exogenously expressed polypeptide containing the amino acid sequence of SEQ ID NO: 2, 4, 6, or 8, or consisting of the amino acid sequence of SEQ ID NO: 2, 4, 6 or 8.

A cell of the invention can be generated by expressing a nucleic acid molecule encoding the polypeptide to be exogenously expressed in a suitable host cell, such as, without limitation, a bacterial cell, yeast cell, insect cell, oocyte or other amphibian cell, or mammalian cell, using methods well known in the art. Suitable expression vectors are well known in the art and include vectors in which a nucleic acid molecule is operatively linked to a regulatory element such as a promoter or enhancer region that is capable of regulating expression of a linked nucleic acid molecule. Appropriate expression vectors include, without limitation, those that can be replicated in eukaryotic or prokaryotic cells, those that remain episomal as well as those which integrate into the host cell genome, and those including constitutive, inducible or regulated promoters, enhancers or other regulatory elements.

Suitable expression vectors for prokaryotic or eukaryotic cells are well known to those skilled in the art (see, for example, Ausubel et al., supra, 1999). Eukaryotic expression vectors can contain, for example, a regulatory element such as, but not limited to, the SV40 early promoter, the cytomegalovirus (CMV) promoter, the mouse mammary tumor virus (MMTV) steroid-inducible promoter, the Moloney murine leukemia virus (MMLV) promoter, and the like. One skilled in the art will know or can readily determine an appropriate expression vector for a particular host cell.

Useful expression vectors optionally contain a regulatory element that provides cell or tissue specific expression or inducible expression of the operatively linked nucleic acid molecule. One skilled in the art can readily determine an appropriate tissue-specific promoter or enhancer that allows expression of a polypeptide of the invention in a desired tissue. Furthermore, any of a variety of inducible promoters or enhancers can also be included in an expression vector for regulated expression of a polypeptide of the invention. Such inducible systems include, yet are not limited to, a tetracycline inducible gene regulatory region (Gossen & Bijard, *Proc. Natl. Acad. Sci. USA,* 89:5547–5551 (1992); Gossen et al., *Science,* 268:1766–1769 (1995); Clontech, Palo Alto, Calif.); a metallothionein promoter inducible by heavy metals; an insect steroid hormone responsive gene regulatory region responsive to ecdysone or related steroids such as muristerone (No et al., *Proc. Natl. Acad. Sci. USA,* 93:3346–3351 (1996); Yao et al., *Nature,* 366:476–479 (1993); Invitrogen, Carlsbad, Calif.); a mouse mammory tumor virus (MMTV) gene regulatory region induced by steroids such as glucocortocoid and estrogen (Lee et al., *Nature,* 294:228–232 (1981); and a heat shock promoter.

An expression vector useful in the invention can be a viral vector such as, without limitation, a retrovirus, adenovirus, adeno-associated virus, lentivirus, or herpesvirus vector. Viral based systems provide the advantage of being able to introduce relatively high levels of a heterologous nucleic acid molecule into a variety of cells. Additionally, certain viral vectors can introduce heterologous DNA into non-dividing cells. A variety of suitable viral expression vectors are well known in the art and include, without limitation, herpes simplex virus vectors (U.S. Pat. No. 5,501,979), vaccinia virus vectors (U.S. Pat. No. 5,506,138), cytomegalovirus vectors (U.S. Pat. No. 5,561,063), modified Moloney murine leukemia virus vectors (U.S. Pat. No. 5,693,508), adenovirus vectors (U.S. Pat. Nos. 5,700,470 and 5,731,172), adeno-associated virus vectors (U.S. Pat. No. 5,604,090), constitutive and regulatable retrovirus vectors (U.S. Pat. Nos. 4,405,712; 4,650,764 and 5,739,018, respectively), papilloma virus vectors (U.S. Pat. Nos. 5,674,703 and 5,719,054), and the like.

A cell of the invention transiently or stably expresses the exogenously expressed polypeptide. Expression vectors for transient or stable expression of a polypeptide can be introduced into cells using transfection methods well known to one skilled in the art. Such methods include, without limitation, infection using viral vectors, lipofection, electroporation, particle bombardment and transfection such as calcium-phosphate mediated transfection. Detailed procedures for these methods can be found in Sambrook et al., *Molecular Cloning: A Laboratory Manual* Cold Spring Harbor Laboratory Press (1989), and the references cited therein. Useful mammalian expression vectors and methods of introducing such vectors into mammalian cells either ex vivo or in vivo are well known in the art. As non-limiting examples, a plasmid expression vector can be introduced into a cell by calcium-phosphate mediated transfection, DEAE dextran-mediated transfection, lipofection, polybrene- or polylysine-mediated transfection, electroporation, or by conjugation to an antibody, gramacidin S, artificial viral envelope or other intracellular carrier. A viral expression vector can be introduced into a cell by infection or transduction, for example, or by encapsulation in a liposome. It further is understood that polypeptides can be delivered directly into cells using a lipid-mediated delivery system (Zelphati et al., *J. Biol. Chem.* 276:35103–35110 (2001)) to produce a cell that contains exogenously expressed COX-1 variant.

Exemplary host cells that can be used to exogenously express a polypeptide of the invention include, yet are not limited to, mammalian primary cells; established mammalian cell lines such as COS, CHO, HeLa, NIH3T3, HEK 293, and HEK 293/EBNA cells; amphibian cells such as *Xenopus* embryos and oocytes; and other vertebrate and invertebrate cells. Exemplary host cells further include, without limitation, insect cells such as *Drosophila* and *Spodoptera frugiperda*, including Sf9 cells, Sf21 cells and other cells compatible with baculovirus expression systems (Murakimi et al., *Cytokine,* 13(1):18–24, (2001)); yeast cells such as *Saccharomyces cerevisiae, Saccharomyces pombe,* or *Pichia pastoris*; and prokaryotic cells such as *Escherichia coli.* Following transfection, cells exogenously expressing a polypeptide of the invention can be selected, for example, using drug resistance. A quantitative assay such as, for example, immunoblot analysis, immunoprecipitation or ELISA can determine the amount of a polypeptide of the invention expressed in a transfected cell. Such methods are known to one skilled in the art and can be found, for example, in Ausubel et al., supra, 1989, or in Harlow et al., supra, 1988.

Further provided herein are methods for identifying a compound that modulates a COX-1 variant, identifying a compound that differentially modulates a COX-1 variant, identifying a compound that specifically binds a COX-1 variant, and identifying a compound that differentially binds to a COX-1 variant. In particular, the invention provides a method for identifying a compound that modulates a COX-1 variant by contacting a COX-1 variant with a compound and determining the level of an indicator which correlates with modulation of a COX-1 variant, where an alteration in the level of the indicator as compared to a control level indicates that the compound is a compound that modulates the COX-1 variant. Further provided herein are methods for identifying a compound that modulates a COX-1 variant by contacting an isolated COX-1 variant or a COX-1 variant over-expressed or exogenously expressed in a genetically engineered cell with a compound and determining the level of an indicator which correlates with modulation of a COX-1 variant, where an alteration in the level of the indicator as compared to a control level indicates that the compound is a compound that modulates the COX-1 variant.

As used herein in reference to a COX-1 variant, the term "modulates" means the ability to alter a characteristic of a COX-1 variant. A characteristic of a COX-1 variant that can be altered can include, without limitation, an amount, activity, or physical conformation of a COX-1 variant. As a non-limiting example, a compound that modulates a COX-1 variant can increase or decrease the binding of a COX-1 variant to a compound like aspirin or other NSAID. As a further non-limiting example, a compound can increase or decrease the binding of a COX-1 variant to an intracellular signaling molecule that initiates a signal transduction pathway within a cell. As still further non-limiting examples, a compound that modulates a COX-1 variant can increase or decrease an activity of a COX-1 variant such as, without limitation, cyclooxygenase activity or peroxidase activity. It is understood that compounds that modulate a COX-1 variant include compounds that specifically bind to a COX-1 variant as well as compounds that do not specifically bind to a $COX_7 1$ variant.

A method of the invention for identifying a compound that modulates a COX-1 variant involves determining the level of an indicator which correlates with modulation of the COX-1 variant, where an alteration in the level of the indicator as compared to a control level indicates that the compound modulates the COX-1 variant. As used herein, the term "indicator" means a detectable substance which is altered qualitatively or quantitatively in response to modulation of a COX-1 variant. An indicator can be a substance that is normally present in a cell, for example, an element such as oxygen, a prostaglandin, eicosinoid, or signal transduction molecule, or a substance that is exogenously expressed or otherwise added to a cell, the level of which correlates with modulation of a COX-1 variant. Examples include, without limitation, luciferase and chemiluminescent substrates. Signal transduction molecules are intracellular substances such as, without limitation, cyclic AMP, inositol phosphates and calcium, the level of which can be altered in response to modulation of a COX-1 variant.

As understood by those of skill in the art, assay methods for identifying compounds that modulate a COX-1 variant generally require comparison to a control. For example, in a method of the invention an alteration in the level of an indicator which correlates with modulation of a COX-1 variant is compared to a control level of the indicator. One type of a control is a sample that is treated substantially the same as the COX-1 variant which is contacted with a compound, with the distinction that the control sample is not exposed to the compound. Controls include, but are not limited to, historical reference values and samples that are assayed simultaneously or sequentially in comparison to the COX-1 variant which is contacted with a compound.

In one embodiment, a method of the invention is practiced using a prostaglandin such as prostaglandin $E_2$ ($PGE_2$) as the indicator. In another embodiment, a method of the invention is practiced using a chemiluminescent substrate for COX-1 activity, for example, the chemiluminescent substrate for COX-1 peroxidative activity available from Assay Designs, Inc. (Ann Arbor, Mich.) or Stressgen Biotechnologies (Victoria, British Columbia). Exogenously expressed substances such as, without limitation, luciferase, b-galactosidase and green fluorescent protein (GFP) also can be indicators useful in a method of the invention.

Further provided herein are methods for identifying a compound that specifically binds to a COX-1 variant by contacting a COX-1 variant with a compound and determining specific binding of the compound to the COX-1 variant. Additionally provided herein are methods for identifying a compound that specifically binds to a COX-1 variant by contacting an isolated COX-1 variant or a COX-1 variant over-expressed or exogenously expressed in a genetically engineered cell with a compound and determining specific binding of the compound to the COX-1 variant.

As used herein in reference to a compound and a COX-1 variant, the term "specific binding" means binding with an affinity for the target COX-1 variant that is measurably higher than the affinity for an unrelated polypeptide such as an unrelated enzyme. For example, a polypeptide or small molecule compound that specifically binds a COX-1 variant has an affinity for the COX-1 variant that is measurably higher than its affinity for an unrelated enzyme. Binding affinity can be low or high affinity so long as the binding is sufficient to be detectable. For example, a compound can specifically bind a COX-1 variant with a binding affinity (Kd) of about $10^{-4}$ M or less, $10^{-5}$ M or less, $10^{-6}$ M or less, $10^{-7}$ M or less, $10^{-8}$ M or less, or $10^{-9}$ M or less. In addition, specific binding includes both covalent and non-covalent binding. For example, several enzymes bind to their substrates and catalyze reactions without covalently binding the substrate molecule. Several methods for detecting or measuring specific binding are well known in the art and discussed further below.

The screening methods of the invention can be practiced using, for example, a COX-1 variant over-expressed or exogenously expressed in a genetically engineered cell. As used herein, the term "genetically engineered cell" means a cell having genetic material which is altered by the hand of man. Such a cell can contain a transient or permanent alteration of its genetic material including, for example, an alteration in genomic or episomal genetic material. The genetic material in a genetically engineered cell can be altered using, without limitation, an exogenously expressed nucleic acid molecule, chemical mutagen or transposable element. It is understood that a genetically engineered cell can contain one or multiple man-made alterations, for example, a cell can be co-transfected with more than one expression vector. As used herein in relation to a COX-1 variant in a genetically engineered cell, the term "over-expressed" means having a protein level of a COX-1 variant greater than the level seen in a corresponding non-genetically engineered cell.

A COX-1 variant can be over-expressed in a genetically engineered cell, for example, by exogenously expressing a nucleic acid molecule encoding the COX-1 variant in a cell as described herein above. It is understood that a COX-1 variant can be over-expressed in a cell that does not normally express the COX-1 variant, or in a cell that naturally expresses the endogenous COX-1 variant. As a non-limiting examples, a COX-1 variant can be over-expressed in a cell that expresses the same or a different endogenous COX-1 variant at a low level. In addition, a COX-1 variant can be over-expressed in a genetically engineered cell, for example, by expressing a regulatory molecule in the cell to increase expression of the endogenous COX-1 variant. Another example of a method whereby a COX-1 variant can be over-expressed in a genetically engineered cell is recombination of a heterologous regulatory region such as, without limitation, a promoter, enhancer or 3' regulator, in the cell such that the heterologous regulatory region results in over-expression of endogenous COX-1 variant. As understood by one skilled in the art, over-expression of a COX-1 variant in a genetically engineered cell includes, without limitation, over-expression of the variant on the surface of the cell, within a cell membrane or in the cytosolic portion of the cell.

A COX-1 variant also can be over-expressed in a cell using a chemical agent. Thus, the invention provides a method for identifying a compound that modulates a COX-1 variant by contacting the COX-1 variant with a compound, where the COX-1 variant is over-expressed in a cell using a chemical agent, and determining the level of an indicator which correlates with modulation of the COX-1 variant, where an alteration in the level of the indicator as compared to a control level indicates that the compound is a compound that modulates the COX-1 variant. The invention also provides a method for identifying a compound that specifically binds to a COX-1 variant by contacting the COX-1 variant with a compound, where the COX-1 variant is over-expressed in a cell using a chemical agent, and determining specific binding of the compound to the COX-1 variant. Chemical agents that result in over-expression of a COX-1 variant include, without limitation, chemicals that induce the level or activity of regulatory factor, such as a transcription factor, that is involved in COX-1 variant expression.

As disclosed above, the methods of the invention can be practiced with a cell that over-expresses a COX-1 variant. In addition, it is understood that an extract of a cell that over-expresses a COX-1 variant such as a genetically engineered cell that over-expresses a COX-1 variant can be useful in the methods of the invention. Methods for generating different types of cellular extracts including, without limitation, whole cell extracts, fractionated extracts, membrane extracts, cytosolic extracts and nuclear extracts are well known in the art. As a non-limiting example, COX-1 variant enriched plasma membrane fractions can be obtained by continuous or discontinuous gradients of, for example, sucrose.

An isolated COX-1 variant also can be useful in a screening method of the invention. As used herein in reference to a COX-1 variant, the term "isolated" means the COX-1 variant is substantially separated from other polypeptides. For example, an isolated COX-1 variant derived from a cell can be substantially purified away from other polypeptides in the cell. Furthermore, an isolated COX-1 variant can be a single subunit of the COX-1 variant or can be a homodimer similar to the structure of the known wild-type human COX-1 enzyme. An isolated COX-1 variant also can contain fused heterologous sequences or other associated non-polypeptide components; for example, an isolated COX-1 variant can be associated with a natural or artificial lipid containing membrane. In one embodiment, a method of the invention is practiced with an isolated COX-1 variant that contains an amino acid sequence having at least 50% amino acid identity with SEQ ID NO: 10 and further contains the amino acid sequence of SEQ ID NOS: 14, 16, 18, 20, 22, or 24; or a conservative variant thereof. In another embodiment, a method of the invention is practiced with an isolated COX-1 variant that contains the amino acid sequence of SEQ ID NOS: 2, 4, 6 or 8, or that consists of the amino acid sequence of SEQ ID NOS: 2, 4, 6 or 8.

A COX-1 variant can be prepared in isolated form using conventional biochemical purification methods, starting either from tissues containing the desired COX-1 variant or from recombinant sources. A COX-1 variant can be isolated by any of a variety of methods well-known in the art, including, but not limited to, precipitation, gel filtration, ion-exchange, reverse-phase and affinity chromatography, and combinations thereof. Other well-known methods for protein isolation are described in Deutscher et al., *Guide to Protein Purification: Methods in Enzymology Vol.* 182, (Academic Press, (1990)). Methods suitable for isolation of a COX-1 variant of the invention using biochemical purification are known in the art as described for example, in Rowlinson et al., *J. Biol. Chem.* 274:23305–23310 (1999), and Marnett et al., *Mol. Pharm.* 26:328–335 (1984). Purification of the COX-1 variant can be routinely monitored, for example, by an immunological assay or functional assay such as a cyclooxygenase or peroxidase assay.

An isolated COX-1 variant also can be produced by chemical synthesis. As a non-limiting example, synthetic isolated COX-1 variants, including fragments thereof, can be produced using an Applied Biosystems, Inc. Model 430A or 431A automatic peptide synthesizer (Foster City, Calif.) employing the chemistry provided by the manufacturer. Methods for synthesizing isolated polypeptides are well known in the art (see, for example, Bodanzsky, *Principles of Peptide Synthesis* (1st ed. & 2d rev. ed.), Springer-Verlag, New York, N.Y. (1984 & 1993), see Chapter 7; Stewart and Young, *Solid Phase Peptide Synthesis*, (2d ed.), Pierce Chemical Co., Rockford, Ill. (1984)).

In the methods of the invention for identifying a compound that modulates, or specifically binds to, a COX-1 variant, an isolated COX-1 variant or COX-1 variant over-expressed or exogenously expressed in a genetically engineered cell can be contacted with a compound in a solution under conditions suitable for interaction between the COX-1 variant and compound. Such contact can occur in vitro, such as in an isolated cell in cell culture, in a whole or partially purified cell extract, or with an isolated polypeptide. As used herein, the term "in vitro" means in an artificial environment outside of a living organism or cell. Contacting performed in a test tube, microcentrifuge tube, 96 well plate, 384 well plate, 1536 well plate or other assay format outside of an organism and without using living cells occurs in vitro.

Contact performed in cells or tissues that have been fixed and are therefore dead (sometimes referred to as in situ experiments) or using cell-free extracts from cells occurs in vitro. Contact can also occur in vivo using, for example, whole animals.

Conditions suitable for contacting an isolated COX-1 variant or COX-1 variant over-expressed or exogenously expressed in a genetically engineered cell with a compound are dependent on the characteristics of the COX-1 variant and the compound. For example, the overall charge of the COX-1 variant and the compound can be considered when adjusting the salt concentration or pH of a buffering solution to optimize the specific binding or modulation of the COX-1 variant by the compound. Usually a salt concentration and pH in the physiological range, for example, about 100 mM KCl and pH 7.0 are reasonable starting points. In addition, other components such as glycerol or protease inhibitors can be added to the solution, for example, to inhibit polypeptide degradation. It is understood that the stability of the contact between the COX-1 variant and the compound can be effected by the salt concentration and temperature at which such contact occurs and that the optimal salt concentration and temperature for contact can be routinely determined by those skilled in the art. For example, reactions can be performed on ice (4° C.), at room temperature (about 25° C.) or at body temperature (37° C.). Suitable conditions can be similar or identical to conditions used for binding of a compound to the wild-type human COX-1. Such conditions are known in the art and include, for example, preincubating cells that express the COX-1 variant with compound for 30 minutes at 25° C., then adding arachidonic acid at a final concentration of 5 or 30 mM for an additional 10 minute incubation at 37° C., as described in Chadrasekharan et al., supra, 2002 (see also Example II). Assayed can then be performed for cyclooxygenase (COX) activity, for example, by radioimmunoassay for $PGE_2$.

The screening methods of the invention are useful for identifying compounds that modulate or differentially modulate, or that specifically bind or differentially bind a COX-1 variant. As used herein, the term "compound" means a molecule of natural or synthetic origin. A compound can be, without limitation, a small organic or inorganic molecule, polypeptide, peptide, peptidomimetic, non-peptidyl compound, carbohydrate, lipid, antibody or antibody fragment, aptamer, or nucleic acid molecule. In one embodiment, the compound is a small organic molecule. It is understood that a compound can have a known or unknown structure, and can be assayed as an isolated molecule or as part of a population of compounds such as in a pool or as a portion of a library.

As is understood by one skilled in the art, a compound can specifically bind to a COX-1 variant without modulating the COX-1 variant; specifically bind to a COX-1 variant, thereby modulating the COX-1 variant; or modulate a COX-1 variant without specifically binding the COX-1 variant. Compounds that specifically bind to a COX-1 variant can include, without limitation, arachidonic acid or other fatty acids, and aspirin or other NSAIDs; such molecules can be identical or similar to, or structurally distinct from those that specifically bind the wild-type COX-1 isoform. A compound that modulates a COX-1 variant but does not directly bind to the COX-1 variant can be, for example, a compound that binds to or effects the activity of a polypeptide in a cell, where that polypeptide increases or decreases the level of a COX-1 variant. Such compounds include, without limitation, transcription or translation regulatory factors, signal transduction polypeptides; kinases and phosphatases; and anti-sense oligonucleotides, inhibitor RNA molecules and ribozymes, that act on the nucleic acid that encodes the COX-1 variant; and molecules that affect the expression or activity of COX-1 inhibitors.

Compounds that modulate or specifically bind to a COX-1 variant further include, but are not limited to, agonists and antagonists for other proteins. Agonists and antagonists for proteins such as receptors are well known in the art.

A library of compounds can be useful in the screening methods of the invention. Such a library can be a random collection of compounds or a focused collection of compounds, for example, compounds that are rationally designed or pre-selected based on one or more physical or functional characteristics. For example, a library of compounds related to aspirin or one or more other compounds can be useful in the screening methods of the invention. A variety of NSAID compounds are known in the art and include, without limitation, aspirin, flurbiprofen, ketoprofen, etodolac, ibuprofen, piroxicam, carprofen, celecoxib, diclofenac, flunixin, meloxicam, deracoxib, NS-398, DUP-697, and SC-58125.

Libraries useful in the methods of the invention include, yet are not limited to, natural product libraries derived from, without limitation, microorganisms, animals, plants, and marine organisms; combinatorial chemical or other chemical libraries such as those containing randomly synthesized compounds; combinatorial libraries containing structural analogs of NSAIDs or other known compounds, or random or biased assortments of, for example, small organic molecules, polypeptides, oligonucleotides, and combinations thereof. Still other libraries of interest include peptidomimetic, multiparallel synthetic collections, and recombinatorial libraries. Combinatorial and other chemical libraries are known in the art, as described, for example, in Myers, *Curr. Opin. Biotechnol.* 8:701–707 (1997). Appropriate libraries can be assembled from catalog sources such as Cayman Chemical Co. (Ann Arbor, Mich.), BIOMOL Research Laboratories, Inc. (Plymouth Meeting, Pa.), Tocris Cooksoon Inc. (Ellisville, Mo.), and others. In addition to NSAID-related compounds, these libraries can include, without limitation, fatty acids, fatty acid amides and esters, and eicosanoids.

In a screening method of the invention, the members of a library of compounds can be assayed for activity individually, in pools, or en masse. An example of en masse screening to identify a compound that modulates or specifically binds to a COX-1 variant is as follows: a library of compounds is assayed in pools for the ability to modulate or specifically bind a COX-1 variant; the sub-population which modulates or specifically binds the COX-1 variant is subdivided; and the assay is repeated as needed in order to isolate an individual compound or compounds from the library that modulate or specifically bind the COX-1 variant.

The methods of the invention can utilize high throughput screening (HTS) techniques to identify compounds that modulate or specifically bind to a COX-1 variant. HTS assays permit screening of large numbers of compounds in an efficient manner. Cell-based high throughput screening systems include, but are not limited to, yeast-based assay systems and mammalian cell expression systems (Jayawickreme and Kost, *Curr. Opin. Biotechnol.* 8:629–634 (1997)). Automated and miniaturized high throughput screening assays are also useful in the methods of the invention (Houston and Banks, *Curr. Opin. Biotechnol.* 8:734–740 (1997)). High throughput screening assays are designed to identify "hits" or "lead compounds" having the desired modulating or specific binding activity, from which modified compounds can be prepared to improve a property of the initial lead compound. Chemical modification of the "hit" or "lead compound" can be based on an identifiable structure/activity relationship (SAR) between the "hit" and a COX-1 variant of the invention. It is understood that assays such as the conversion of arachidonic acid to a prostaglandin such as $PGE_2$ and other assays of cyclooxygenase or peroxidase activity can be performed as conventional or high throughput screening assays to identify a compound that modulates or specifically binds to a COX-1 variant according to a method of the invention. In addition, as understood by one skilled in the art, a radioligand binding or other assay can be modified, for example, by using two COX-1 inhibitors that bind COX-1 in a competition assay.

Various types of assays can be useful for identifying a compound that modulates or specifically binds to a COX-1 variant in a method of the invention. For example, several assays can be used to measure specific binding of a compound to a COX-1 variant in a method of the invention. An assay that can be used for measuring specific binding of a compound to a COX enzyme is a radioligand binding assay. Radioligand binding assays can be performed on cells or in solution, for example, using isolated cell membranes. As a non-limiting example, cells or cell membranes that transiently or stably over-express a COX-1 variant can be incubated with a ligand including a novel or known ligand such as a radioactively labeled NSAID. After washing away any unbound radioactively labeled NSAID, compounds of interest can be incubated with the cells. After incubation, the solution around the cells is collected and the amount of radioactively labeled NSAID in the solution is determined using, for example, a scintillation counter. Compounds that specifically bind to the COX-1 variant displace the radioactively labeled NSAID from the COX enzyme and thereby increase radioactively labeled NSAID in solution. As understood by one skilled in the art, a ligand such as a NSAID also can be labeled with a non-radioactive moiety such as a fluorescent moiety.

A variety of other assays well known in the art can be used to determine specific binding of a compound to a COX-1 variant in a method of the invention. Such methods for determining specific binding to a COX-1 variant include, without limitation, detecting specific binding of a labeled compound to a COX-1 variant which is immobilized. For example, a compound can be conjugated to a radiolabel, fluorescent label or enzyme label such as alkaline phosphatase, horse radish peroxidase or luciferase. Labeled compound can then bind to a COX-1 variant, for example a COX-1 variant membrane preparation, which is immobilized, for example, on a solid support such as a latex bead. Unbound compound is washed away, and the amount of specifically bound compound can be detected based on its label. Fluorescently labeled compound can also be bound to a COX-1 variant in solution and bound complexes detected, for example using a fluorescence polarization assay (Degterev et al., *Nature Cell Biology* 3:173–182 (2001)). Such assays also can be performed where the COX-1 variant is labeled and the compound is immobilized or in solution. One skilled in the art understands that a variety of additional means can be used to determine specific binding to a COX-1 variant; as non-limiting examples, specific binding of a compound to a $^{15}N$-labeled COX-1 variant can be detected using nuclear magnetic resonance (NMR), or specific binding can be determined using an antibody that specifically recognizes a ligand-bound COX-1 variant. In addition, binding of a compound to a COX-1 variant can be determined or confirmed using X-ray crystallography. Conditions for crystallography can be based on those used to solve the crystal structure of wild-type sheep seminal vesicle COX-1 (Picot et al, *Nature* 367:243–249 (1994)).

High-throughput assays for determining specific binding to a COX-1 variant further include, but are not limited to, scintillation proximity assays (Alouani, *Methods Mol. Biol.* 138:135-41 (2000)). Scintillation proximity assays involve the use of a fluomicrosphere coated with an acceptor molecule, such as an antibody, to which an antigen will bind selectively in a reversible manner. For example, a compound can be bound to a fluomicrosphere using an antibody that specifically binds to the compound, and contacted with a $^3H$ or $^{125}I$ labeled COX-1 variant. If the labeled COX-1 variant specifically binds to the compound, the radiation energy from the labeled COX-1 variant is absorbed by the fluomicrosphere, thereby producing light which is easily measured. Such assays can also be performed where the COX-1 variant is bound to the fluomicrosphere, and the compound is labeled.

Additional assays suitable for determining specific binding of a compound to a COX-1 variant in a screening method of the invention include, without limitation, UV or chemical cross-linking assays (Fancy, *Curr. Opin. Chem. Biol.* 4:28–33 (2000)) and biomolecular interaction analyses (Weinberger et al., *Pharmacogenomics* 1:395–416 (2000)). Specific binding of a compound to a COX-1 variant can be determined by cross-linking the compound and variant, if they are in contact with each other, using UV or a chemical cross-linking agent. In addition, a biomolecular interaction analysis (BIA) can detect whether two components are in contact with each other. In such an assay, one component, such as a COX-1 variant, for example, an isolated COX-1 variant or a membrane preparation containing a COX-1 variant, is bound to a BIA chip, and a second component such as a compound is passed over the chip. If the two components specifically bind, the contact results in an electrical signal, which is readily detected.

In addition, virtual computational methods and the like can be used to identify compounds that modulate or specifically bind to a COX-1 variant in a screening method of the invention. Exemplary virtual computational methodology involves virtual docking of small-molecule compounds on a virtual representation of a COX-1 variant structure in order to determine or predict specific binding. See, for example, Shukur et al., supra, 1996; Lengauer et al., *Current Opinions in Structural Biology* 6:402–406 (1996); Choichet et al., *Journal of Molecular Biology* 221:327–346 (1991); Cherfils et al., *Proteins* 11:271–280 (1991); Palma et al., *Proteins* 39:372–384 (2000); Eckert et al., *Cell* 99:103–115 (1999); Loo et al., *Med. Res. Rev.* 19:307–319 (1999); and Kramer et al., *J. Biol. Chem.* (2000).

Assays useful in the methods of the invention that do not directly measure binding to a COX-1 variant include, for example, assays that measure COX-1 enzyme activity. Such assays include, without limitation, measurement of uptake of oxygen using an oxygraph, measurement of the conversion of arachidonic acid to prostaglandins or eicosinoids, and measurement of a chemiluminescent substrate for COX-1 peroxidase activity. Prostaglandin or eicosinoid synthesis from arachiodonic acid or other precursors can be measured using any standard detection method known in the art such as, for example, radioimmunoassays (RIAs) or enzyme-linked immunosorbent assays (ELISAs). A prostaglandin synthesis assay is described in Example II as is an assay that measures the turn-over of a COX-1 substrate or co-substrate such as N,N,N,N'-tetramethyl-p-phenylenediamine (TMPD). In addition, an example of a chemiluminescent assay for COX-1 peroxidase activity such as available from Assay Designs, Inc. (Ann Arbor, Mich.) or Stressgen Biotechnologies (Victoria, British Columbia) is described in Example II.

In addition to the methods described above for identifying a compound that modulates or specifically binds a COX-1 variant, the invention also provides related methods for identifying a compound that differentially modulates or differentially binds to a COX-1 variant. It is understood that the COX-1 variants, cells, compounds, indicators, conditions for contacting, and assays described above also can be applied to methods for identifying a compound that differentially modulates or differentially binds to a COX-1 variant.

In particular, the invention provides a method for identifying a compound that differentially modulates a COX-1 variant by a) contacting an isolated COX-1 variant or a COX-1 variant over-expressed or exogenously expressed in a genetically engineered cell with a compound; b) determining the level of an indicator which correlates with modulation of a COX-1 variant; c) contacting a second COX enzyme with the compound; d) determining the level of a corresponding indicator which correlates with modulation of the second COX enzyme; and e) comparing the level of the indicator from step (b) with the level of the corresponding indicator from step (d), where a different level of the indicator from step (b) compared to the level of the corresponding indicator from step (d) indicates that the compound is a compound that differentially modulates the COX-1 variant.

As described above, an indicator is a detectable substance which is altered qualitatively or quantitatively in response to modulation of a COX-1 variant. A "corresponding indicator" is an indicator that can be compared to the indicator which correlates with modulation of the COX-1 variant in step (b). For example, a corresponding indicator can be the same indicator as the indicator which correlates with modulation of the COX-1 variant in step (b). A corresponding indicator also can be a different indicator as the indicator which correlates with modulation of the COX-1 variant in step (b) so long as the corresponding indicator can be compared to the indicator which correlates with modulation of the COX-1 variant in step (b). As a non-limiting example, the indicator in step (b) can be prostaglandin $E_2$ ($PGE_2$), and the corresponding indicator can be a substance whose amount is directly correlated with prostaglandin $E_2$ ($PGE_2$) level, such as a breakdown product of $PGE_2$. As a further non-limiting example, the indicator in step (b) and corresponding indicator in step (d) can be related molecules, such as two different fluorophores. In one embodiment, the level of the indicator which correlates with modulation of the COX-1 variant in step (b) is greater than the level of the corresponding indicator from step (d). In another embodiment, the level of the indicator which correlates with modulation of the COX-1 variant in step (b) is less than the level of the corresponding indicator from step (d).

The invention also provides a method for identifying a compound that differentially binds to a COX-1 variant by a) contacting an isolated COX-1 variant or a COX-1 variant over-expressed or exogenously expressed in a genetically engineered cell with a compound; b) determining specific binding of the compound to the COX-1 variant; c) contacting a second COX enzyme with the compound; d) determining specific binding of the compound to the second COX enzyme; and e) comparing the level of specific binding from step (b) with the level of specific binding from step (d), where a different level of specific binding from step (b) compared to the level of specific binding from step (d) indicates that the compound is a compound that differentially binds to the COX-1 variant. In one embodiment, the different level of specific binding is an increased level of binding of the compound to the COX-1 variant as compared to the second COX enzyme. In another embodiment, the different level of specific binding is a decreased level of binding of the compound to the COX-1 variant as compared to the second COX enzyme.

As disclosed above in regard to other methods, a COX-1 variant useful in a method of the invention for identifying a compound that differentially modulates or differentially binds a COX-1 variant can be any of a variety of COX-1 variants such as an isolated polypeptide containing an amino acid sequence having at least 50% amino acid identity with SEQ ID NO: 10 and further having the amino acid sequence of SEQ ID NOS: 14, 16, 18, 20, 22, or 24; or a conservative variant thereof; an isolated polypeptide containing the amino acid sequence of SEQ ID NO: 2, 4, 6 or 8; or an isolated polypeptide consisting of the amino acid sequence of SEQ ID NOS: 2, 4, 6 or 8. In addition, the COX-1 variant can be over-expressed or exogenously expressed in a genetically engineered cell. For example, the COX-1 variant can be exogenously over-expressed in a genetically engineered cell.

In the methods of the invention for identifying a compound that differentially modulates or differentially binds a COX-1 variant, the second COX enzyme can be any COX enzyme of interest. For example, the second COX enzyme can be, without limitation, any other COX enzyme such as a different COX-1 variant, a wild-type COX-1, wild-type COX-2, a known variant of COX-1 or COX-2, or a functional fragment of these polypeptides. In one embodiment, the second COX enzyme contains the amino acid sequence SEQ ID NO: 10, or a functional fragment thereof. It is understood that the second COX enzyme can be, for example, expressed in a cell endogenously or exogenously or can be an isolated COX enzyme polypeptide.

In one embodiment, a method of the invention is practiced using a COX-1 variant and second COX enzyme which are expressed in different cells of the same or different cell-type. In addition, the methods of the invention can be practiced using a COX-1 variant and second COX enzyme which are expressed in the same cell, for example, where the COX-1 variant does not have identical binding and signal transduction effects as the co-expressed second COX enzyme.

As understood by one skilled in the art, in the methods of the invention for identifying a compound that modulates, differentially modulates, specifically binds, or differentially binds a COX-1 variant the order of the steps can be changed. In addition, steps can be performed simultaneously or sequentially.

The invention further provides an isolated nucleic acid molecule having a nucleotide sequence that encodes a polypeptide containing an amino acid sequence having at least 50% amino acid identity with SEQ ID NO: 10 and further containing the amino acid sequence of SEQ ID NOS: 20, 22 or 24, or a conservative variant thereof. The invention also provides an isolated nucleic acid molecule containing a nucleotide sequence that encodes the amino acid sequence of SEQ ID NO: 2, 4, 6 or 8. The invention further provides an isolated nucleic acid molecule consisting of a nucleotide sequence of SEQ ID NO: 1, 3, 5 or 7.

An isolated nucleic acid molecule can be a DNA or RNA molecule and further can have a sense or complementary anti-sense strand or both. It is understood that an isolated nucleic acid molecule of the invention can be a double-stranded or a single-stranded molecule, an RNA or DNA molecule, and can optionally include non-coding sequence. DNA molecules of the invention include cDNA molecules as well as wholly or partially chemically synthesized DNA sequences.

The nucleic acid molecules of the invention optionally include heterologous nucleic acid sequences that are not part of the COX-1 variant-encoding sequence in nature. Such a heterologous nucleic acid sequence can be optionally separated from the COX-1 variant-encoding sequence by an encoded cleavage site that facilitates removal of non-COX-1 variant polypeptide sequences from the expressed fusion protein. Heterologous nucleic acid sequences include, without limitation, sequences encoding poly-histidine sequences, FLAG tags and other epitopes; glutathione-S-transferase, thioredoxin, and maltose binding protein domains or other domains or sequences that facilitate purification or detection of a fusion protein containing a COX-1 variant of the invention.

An isolated nucleic acid molecule of the invention encoding SEQ ID NOS: 20, 22 or 24 has a nucleotide sequence that is distinct from the nucleotide sequence of the human COX-1 genomic clone AF440204 since the nucleotide sequence which encodes the amino acid sequence SEQ ID NOS: 20, 22 or 24 spans the junction between newly identified alternatively spliced exons and conserved exons 3 or 6. The intron/exon structure of the human COX-1 genomic clone AF440204 is shown in FIG. 7 along with the intron/exon structure of COX-1 variants ALT-1, ALT-2, ALT-3 and ALT-4. As understood by one skilled in the art, an intron starts with the dinucleotide GT and ends with the dinucleotide AG.

The invention further provides a vector containing a nucleic acid molecule having a nucleotide sequence that encodes a polypeptide containing an amino acid sequence having at least 50% amino acid identity with SEQ ID NO: 10 and that includes the amino acid sequence of SEQ ID NOS: 20, 22 or 24, or a conservative variant thereof. The invention also provides a vector which includes a nucleic acid molecule containing a nucleotide sequence that encodes the amino acid sequence of SEQ ID NO: 2, 4, 6 or 8, or conservative variants thereof, or consisting of the amino acid sequence of SEQ ID NO: 2, 4, 6, or 8. In addition, the invention provides a vector containing the nucleotide sequence of SEQ ID NO: 1, 3, 5, or 7, or consisting of the nucleotide sequence of SEQ ID NO: 1, 3, 5 or 7. The invention further provides a host cell including a vector which contains a nucleic acid molecule of the invention.

Vectors are useful, for example, for subcloning and amplifying a nucleic acid molecule encoding a polypeptide of the invention and for recombinantly expressing the encoded COX-1 variant or other polypeptide. Vectors of the invention include, without limitation, viral vectors such as bacteriophage, baculovirus and retrovirus vectors; cosmids and plasmids; and, particularly for cloning large nucleic acid molecules, bacterial artificial chromosome vectors (BACs) and yeast artificial chromosome vectors (YACs). Such vectors are commercially available, and their uses are well known in the art. Vectors further encompass expression vectors such as those discussed herein above.

The invention also provides an isolated nucleic acid molecule containing a nucleotide sequence that encodes the amino acid sequence of SEQ ID NOS: 20, 22 or 24. Such a nucleic acid molecule of the invention can be used, without limitation, in recombinant cloning methods or as a nucleic acid probe. The amino acid sequence of SEQ ID NO: 20 or 22 contains nine amino acids which begin with five amino acid residues that correspond to the amino acid sequence present in newly identified exon A or B and and end with four amino acid residues that correspond to the amino acid sequence in exon 3, an exon which is present in human wild-type COX-1 as well as the COX-1 variants ALT-1, ALT-3, and ALT-4. The amino acid sequence of SEQ ID NO: 24 contains nine amino acids which begin with five amino acid residues that correspond to the amino acid sequence present in newly identified exon A and end with four amino acid residues that correspond to the amino acid sequence in exon 6.

As non-limiting examples, nucleic acid molecules of the invention can be derived from the unique nucleotide sequence which surrounds the junction between newly identified alternatively spliced exon A and conserved exon 3 present in COX-1 variants ALT-1 and ALT-3, and can include, for example, 20 nucleotides spanning the splice junction. The COX-1 variants ALT-1 and ALT-3 include the nucleic acid sequence gcggacccaggggcgcccac (SEQ ID NO: 27) at the 5' splice junction and ccgaggctcatgaatccctg (SEQ ID NO: 28) at the 3' splice junction. The COX-1 variant ALT-2 also includes the nucleic acid sequence gcggaccaggggcgcccac (SEQ ID NO: 27) at the 5' splice junction. This variant, in which exon A is spliced to exon 6, contains the nucleic acid sequence ccgaggctcaggaagaagca (SEQ ID NO: 29) at the 3' splice junction.

In addition, nucleic acid molecules of the invention can be derived from the unique nucleotide sequence which surrounds the COX-1 variant ALT-4 junction between newly identified alternatively spliced exon B and conserved exon 3. For example, nucleic acid molecules containing 20 nucleotides spanning the splice junction are as follows. The COX-1 variant ALT-4 includes the nucleic acid sequence gcggacccaggggcgcccac (SEQ ID NO: 27) at the 5' splice junction, just as for COX-1 variants ALT-1, ALT-2 and ALT-3, but contains ctgaactcagtgaatccctg (SEQ ID NO: 30) at the 3' splice junction.

As is understood by one skilled in the art, a nucleic acid molecule of the invention can incorporate nucleotide sequence in addition to the nucleotide sequence of SEQ ID NOS: 27, 28, 29 or 30. For example, a nucleic acid molecule of the invention can include further naturally occurring sequence at the 5' or 3' end of SEQ ID NOS: 27, 28, 29 or 30. Also, for example, a nucleic acid molecule of the invention can include one or more additional heterologous sequences such as nucleotide sequences encoding restriction enzyme sites or epitope tags. As non-limiting examples, nucleic acid molecules of the invention can be used in hybridization reactions such as Southern and Northern blots, to encode polypeptide sequence in recombinant cloning methods, or as primers in polymerase chain reactions.

The invention also provides an isolated nucleic acid molecule having a nucleotide sequence that encodes a polypeptide containing or consisting of substantially the same amino acid sequence as SEQ ID NO: 2, 4, 6 or 8 as described above. In addition, the invention provides an isolated nucleic acid molecule containing or consisting of substantially the same nucleotide sequence as SEQ ID NO: 1, 3, 5 or 7.

The invention further provides a method for preventing or reducing the severity of a disease associated with COX-1 or a COX-1 variant in a subject by introducing into the subject a compound that modulates or differentially modulates a COX-1 variant or another compound identified by a method of the invention. The invention also provides a method for preventing or reducing the severity of a cardiovascular disorder in a subject by introducing into the subject a compound that modulates or differentially modulates a COX-1 variant or another compound identified by a method of the invention. In addition, the invention provides a method for preventing or reducing the severity of ocular hypertension in a subject by introducing into the subject a compound that modulates or differentially modulates a COX-1 variant or another compound identified by a method of the invention. Such a compound can be used, without limitation, to prevent or reduce the severity of glaucoma.

As used herein, a "disease associated with COX-1 or a COX-1 variant" means any disease or condition in which modulation of the activity of the wild-type COX-1 enzyme or a COX-1 variant can be beneficial. It is understood that the underlying cause of the disease or condition may or may not be due to an abnormality in expression or activity of a wild-type COX-1 enzyme or a COX-1 variant.

A disease or condition associated with COX-1 or a COX-1 variant can be, without limitation, pain, fever, a cardiovascular disorder or an ocular disorder such as glaucoma, ocular hypertension, uveitis, allergic conjunctivitis and related disorders. Additional diseases or conditions associated with COX-1 or a COX-1 variant can include, without limitation, diseases involving inflamation, for example, rheumatoid arthritis, ankylosing spondylitis, osteoarthritis, bursitis, tendinitis, and gout. As non-limiting examples, such a compound can be used in humans for prophylatic treatment of a cardiovascular disorder or to prevent or treat pain such as headache, muscle ache, or pain caused by any of a variety of inflammatory or degenerative joint diseases.

As discussed above, the iris is the major site in the human eye for production of prostaglandins, which regulate smooth muscle contraction, blood-aqueous barrier penetration and intraocular pressure (Matsuo and Cynader, supra, 1993). COX-1 appears to be constitutively expressed in the human iris, whereas COX-2 expression is triggered by lipopolysaccharides (Van Haeringen et al., supra, 2000). Furthermore, the NSAID S(+)flurbiprofen inhibits COX-170-fold more potently in human iris than in human blood (Haeringen et al., supra, 2000), a difference which may be due to expression of an alternatively spliced form of COX-1 in human iris or whole blood.

Thus, a compound identified by the methods of the invention can be used, without limitation, to prevent or reduce the severity of uveitis, which is inflammation of the uvea or the middle layer of the eye. The role of prostaglandins in uveitis is established. The uvea consists of three structures: the iris, the ciliary body and the choroid. Inflammation occurring in any of these three structures is termed uveitis. Inflammation in uveitis may involve any, but not necessarily all, of these three structures. Depending upon which structures are inflamed, uveitis can be further subcatergorzied into one of three main diagnoses including: 1) iritis or anterior uveitis, 2) cyclitis or intermediate uveitis, and 3) choroiditis or posterior uveitis.

Furthermore, a compound that modulates or differentially modulates a COX-1 variant or which is otherwise identified by a method of the invention can be used alone or in combination with one or more different compounds or other therapeutic agents or procedures for treatment of uveitis. Agents that are currently used in the treatment of uveitis include, but are not limited to, steroids, mydriatics, and immunosuppressants such as cyclosporin, azathioprine, methohextrate, mycophenolate, mofetil (cellcept), tacrolimus and anti-tumor necrosis factor (TNF).

Other ocular conditions that can be prevented or treated with a compound that modulates or differentially modulates a COX-1 variant by a method of the invention include, without limitation, diabetic retinopathy; macular edema such as that associated with diabetes; conditions of retinal degeneration such as glaucoma, macular degeneration such as age-related macular degeneration (ARMD) and retinitis pigmentosa; retinal dystrophies; inflammatory disorders of the retina; vascular occlusive conditions of the retina such as retinal vein occlusions or branch or central retinal artery occlusions; retinopathy of prematurity; retinopathy associated with blood disorders such as sickle cell anemia; elevated intraocular pressure; ocular itch; damage following retinal detachment; damage or insult due to vitrectomy, retinal or other surgery; and other retinal damage including therapeutic damage such as that resulting from laser treatment of the retina, for example, pan-retinal photocoagulation for diabetic retinopathy or photodynamic therapy of the retina, for example, for age-related macular degeneration. Ocular conditions that can be prevented or treated with a compound that modulates or differentially modulates a COX-1 variant by a method of the invention further include, without limitation, genetic and acquired optic neuropathies such as optic neuropathies characterized primarily by loss of central vision, for example, Leber's hereditary optic neuropathy (LHON), autosomal dominant optic atrophy (Kjer disease) and other optic neuropathies such as those involving mitochondrial defects, aberrant dynamin-related proteins or inappropriate apoptosis; and optic neuritis such as that associated with multiple sclerosis, retinal vein occlusions or photodynamic or laser therapy. See, for example, Carelli et al., *Neurochem. Intl.* 40:573–584 (2002); and Olichon et al., *J. Biol. Chem.* 278:7743–7746 (2003).

A compound that modulates or differentially modulates a COX-1 variant or another compound identified by a method of the invention also can be useful for preventing or treating pain. The term pain, as used herein, includes, without limitation, inflammatory pain, headache pain, muscle pain, visceral pain, neuropathic pain, and referred pain. Pain can be continuous or intermittent, of short duration such as acute pain, or of long duration such as chronic pain. Chronic pain is distinguished from acute pain, which is immediate, generally high threshold, pain brought about by injury such as a cut, crush, burn, or by chemical stimulation such as that experienced upon exposure to capsaicin, the active ingredient in chili peppers.

The methods of the invention further can be used, without limitation, to treat chronic or other headache pain such as pain associated with cluster headaches, tension headaches or chronic daily headaches; muscle pain including, but not limited to, that associated with back or other spasm; inflammatory pain or other symptoms resulting, for example, from spondylitis or arthritis such as rheumatoid arthritis, gouty arthritis, or osteoarthritis; gout; bursitis; painful menstruation and fever. In addition, the methods of the invention can be used, for example, to treat pain associated with injury, surgery, dental procedures, dysmenorrhea, labor and other pain associated with the female reproductive system, and systemic illness such as, without limitation, cancer. It is understood that these and other conditions which may respond to NSAIDs can be prevented or treated using a compound that modulates or differentially modulates a COX-1 variant disclosed herein.

As described above, a compound that modulates or differentially modulates a COX-1 variant or another compound identified by a method of the invention also can be useful for preventing or treating an immune disease, for example, without limitation, uveitis. In addition, such a compound can be used to prevent or treat a disease associated with allergy, such as, without limitation, allergic conjunctivitis.

A compound that modulates or differentially modulates a COX-1 variant or another compound identified by a method of the invention also can be useful for preventing or treating a cardiovascular disorder. Such cardiovascular diseases include, but are not limited to, atherosclerosis; thrombosis; restenosis; vasculitis including autoimmune and viral vasculitis such as polyarteritis nodosa, Churg-Strass syndrome, Takayasu's arteritis, Kawasaki Disease and Rickettsial vasculitis; atherosclerotic aneurisms; myocardial hypertrophy; congenital heart diseases (CHD); ischemic heart disease and anginas; acquired valvular/endocardial diseases; primary myocardial diseases including myocarditis; arrhythmias; and cardiac tumors.

In the methods of the invention for preventing or reducing the severity of ocular and other disease associated with a COX-1 or COX-1 variant, a compound can optionally be formulated together-with a pharmaceutically acceptable carrier for delivery to the subject to be treated. Suitable pharmaceutically acceptable carriers are well known in the art and include, for example, aqueous or organic solvents such as physiologically buffered saline, glycols, glycerol, oils or injectable organic esters. A pharmaceutically acceptable carrier can also contain a physiologically acceptable agent that acts, for example, to stabilize or increase solubility of a pharmaceutical composition. Such a physiologically acceptable agent can be, for example, a carbohydrate such as glucose, sucrose or dextrans; an antioxidant such as ascorbic acid or glutathione; a chelating agent; a low molecular weight polypeptide; or another stabilizer or excipient. Pharmaceutically acceptable carriers including solvents, stabilizers, solubilizers and preservatives, are well known in the art as described, for example, in Martin, *Remington's Pharm. Sci.*, 15th Ed. (Mack Publ. Co., Easton, 1975).

Ophthalmic compositions can be useful in the methods of the invention for preventing or alleviating an ocular condition. An ophthalmic composition contains an ophthalmically acceptable carrier, which is any carrier that has substantially no long term or permanent detrimental effect on the eye to which it is administered. Examples of ophthalmically acceptable carriers include, without limitation, water, such as distilled or deionized water; saline; and other aqueous media. An ophthalmic composition useful in the invention can include, for example, a soluble $\alpha$-2/$\alpha$-1 selective agonist, or an $\alpha$-2/$\alpha$-1 selective agonist as a suspension in a suitable carrier.

Topical ophthalmic compositions useful for alleviating an ocular condition include, without limitation, ocular drops, ocular ointments, ocular gels and ocular creams. Such ophthalmic compositions are easy to apply and deliver the active compound effectively.

A preservative can be included, if desired, in an ophthalmic composition useful in a method of the invention. Such a preservative can be, without limitation, benzalkonium chloride, chlorobutanol, thimerosal, phenylmercuric acetate, or phenylmercuric nitrate. Vehicles useful in a topical ophthalmic composition include, yet are not limited to, polyvinyl alcohol, povidone, hydroxypropyl methyl cellulose, poloxamers, carboxymethyl cellulose, hydroxyethyl cellulose and purified water.

A tonicity adjustor also can be included, if desired, in an ophthalmic composition administered to alleviate an ocular condition without concomitant sedation according to a method of the invention. Such a tonicity adjustor can be, without limitation, a salt such as sodium chloride, potassium chloride, mannitol or glycerin, or another pharmaceutically or ophthalmically acceptable tonicity adjustor.

Various buffers and means for adjusting pH can be used to prepare an ophthalmic composition useful in the invention, provided that the resulting preparation is ophthalmically acceptable. Such buffers include, but are not limited to, acetate buffers, citrate buffers, phosphate buffers and borate buffers. It is understood that acids or bases can be used to adjust the pH of the composition as needed. Ophthalmically acceptable antioxidants useful in preparing an ophthalmic composition include, yet are not limited to, sodium metabisulfite, sodium thiosulfate, acetylcysteine, butylated hydroxyanisole and butylated hydroxytoluene.

Those skilled in the art can formulate a compound that modulates, differentially modulates, specifically binds, or differentially binds a COX-1 variant to ensure proper compound distribution and bioavailablility in vivo. For example, some regions of the eye can be inaccessible to some systemically administered drugs, and as a result topical drug delivery can be used. Polymers can be added to ophthalmic solutions to increase bioavailability (Ludwig and Ootenhgm, *S.T.P. Pharm. Sci.*, 2:81–87 (1992)). In addition, colloidal systems such as, without limitation, liposomes, microparticles or nanoparticules can be used to increase penetration of a compound into the eye. Ocular drug absorption also can be enhanced using, for example, iontophoresis, prodrugs, and cyclodextrins.

Methods of ensuring appropriate distribution in vivo also can be provided by rechargeable or biodegradable devices, particularly where concentration gradients or continuous delivery is desired. Various slow release polymeric devices are known in the art for the controlled delivery of drugs, and include both biodegradable and non-degradable polymers and hydrogels. Polymeric device inserts can allow for accurate dosing, reduced systemic absorption and in some cases, better patient compliance resulting from a reduced frequency of administration. Those skilled in the art understand that the choice of the pharmaceutical formulation and the appropriate preparation of the compound will depend on the intended use and mode of administration.

A compound that modulates or specifically binds to a COX-1 variant, or that is otherwise identified by a screening method of the invention can be administered to a subject by any effective route. Suitable routes of administration include, but are not limited to, oral, topical, intraocular, intradermal, parenteral, intranasal, intravenous, intramuscular, intraspinal, intracerebral and subcutaneous routes. The present invention also provides compounds containing an acceptable carrier such as any of the standard pharmaceutical carriers, including phosphate buffered saline solution, water and emulsions such as an oil and water emulsion, and various types of wetting agents.

A method of the invention is practiced by peripherally administering to a subject an effective amount of a compound that modulates or differentially modulates a COX-1 variant or another compound identified by a method of the invention. As used herein in reference to such a compound, the term "peripherally administering" or "peripheral administration" means introducing the compound into a subject outside of the central nervous system. Thus, peripheral administration encompasses any route of administration other than direct administration to the spine or brain.

An effective amount of a compound of the invention can be peripherally administered to a subject by any of a variety of means depending, for example, on the type of condition to be alleviated, the pharmaceutical formulation, and the history, risk factors and symptoms of the subject. Routes of peripheral administration suitable for the methods of the invention include both systemic and local administration. As non-limiting examples, an effective amount of a compound of the invention can be administered orally; parenterally; by subcutaneous pump; by dermal patch; by intravenous, intra-articular, subcutaneous or intramuscular injection; by topical drops, creams, gels or ointments; as an implanted or injected extended release formulation; or by subcutaneous minipump or other implanted device, and by inhalation by aerosol and similar devices.

One skilled in the art understands that peripheral administration can be local or systemic. Local administration results in significantly more of a compound of the invention being delivered to and about the site of local administration than to regions distal to the site of administration. Systemic administration results in delivery of a compound of the invention essentially throughout at least the entire peripheral system of the subject.

Routes of peripheral administration useful in the methods of the invention encompass, without limitation, oral administration, topical administration, intravenous or other injection, and implanted minipumps or other extended release devices or formulations. A compound of the invention can be peripherally administered, without limitation, orally in any acceptable form such as in a tablet, pill, capsule, powder, liquid, suspension, emulsion or the like; an aerosol; as a suppository; by intravenous, intraperitoneal, intramuscular, subcutaneous or parenteral injection; by transdermal diffusion or electrophoresis; topically in any acceptable form such as in drops, creams, gels or ointments; and by minipump or other implanted extended release device or formulation. A compound of the invention optionally can be packaged in unit dosage form suitable for single administration of precise dosages, or in sustained release dosage form for continuous controlled administration.

Chronic pain and other chronic conditions such as, without limitation, chronic neurological conditions can be alleviated using any of a variety of forms of repeated or continuous administration as necessary. In the methods of the invention for alleviating chronic pain or another chronic condition, means for repeated or continuous peripheral administration include, without limitation, repeated oral or topical administration, and administration via subcutaneous minipump. As non-limiting examples, a method of the invention can be practiced by continuous intravenous administration via implanted infusion minipump, or using an extended release formulation.

It is understood that slow-release formulations can be useful in the methods of the invention for alleviating chronic pain or other chronic conditions such as, without limitation, a chronic neurodegenerative conditions. It is further understood that the frequency and duration of dosing will be dependent, in part, on the alleviation desired and the half-life of the compound of the invention and that a variety of routes of administration are useful for delivering slow-release formulations, as detailed hereinabove.

A compound of the invention can be peripherally administered to a subject to alleviate an ocular condition by any of a variety of means depending, in part, on the characteristics of the compound to be administered and the history, risk factors and symptoms of the subject. Peripheral routes of administration suitable for alleviating an ocular condition in a method of the invention include both systemic and local administration. In particular embodiments, a pharmaceutical composition containing a compound of the invention is administered topically, or by local injection, or is released from an intraocular or periocular implant.

Systemic and local routes of administration useful in alleviating an ocular condition according to a method of the invention encompass, without limitation, oral gavage; intravenous injection; intraperitoneal injection; intramuscular injection; subcutaneous injection; transdermal diffusion and electrophoresis; topical eye drops and ointments; periocular and intraocular injection including subconjunctival injection; extended release delivery devices such as locally implanted extended release devices; and intraocular and periocular implants including bioerodible and reservoir-based implants.

In one embodiment, a method of the invention for alleviating an ocular condition is practiced by administering an ophthalmic composition containing a compound of the invention topically to the eye. The $\alpha$-2/$\alpha$-1 selective agonist can be administered, for example, in an ophthalmic solution (ocular drops). In another embodiment, an ophthalmic composition containing a compound of the invention is injected directly into the eye. In a further embodiment, an ophthalmic composition containing a compound of the invention is released from an intraocular or periocular implant such as a bioerodible or reservoir-based implant.

As indicated above, an ophthalmic composition containing a compound of the invention can be administered locally via an intraocular or periocular implant, which can be, without limitation, bioerodible or reservoir-based. An implant refers to any material that does not significantly migrate from the insertion site following implantation. An implant can be biodegradable, non-biodegradable, or composed of both biodegradable and non-biodegradable materials; a non-biodegradable implant can include, if desired, a refillable reservoir. Implants useful in a method of the invention for alleviating an ocular condition include, for example, patches, particles, sheets, plaques, microcapsules and the like, and can be of any shape and size compatible with the selected site of insertion, which can be, without limitation, the posterior chamber, anterior chamber, suprachoroid or subconjunctiva of the eye. It is understood that an implant useful in the invention generally releases the implanted pharmaceutical composition at an effective dosage to the eye of the subject over an extended period of time. A variety of ocular implants and extended release formulations suitable for ocular release are well known in the art, as described, for example, in U.S. Pat. Nos. 5,869,079 and 5,443,505.

An effective dose of a compound for use in a method of the invention can be determined, for example, by extrapolation from the concentration required in a COX-1 or COX-1 variant binding or activity assay such as one of the assays disclosed herein above. An effective dose of a compound for the treatment of a disease associated with COX-1 or a COX-1 variant also can be determined from appropriate animal models, such as transgenic mice. As non-limiting examples, animal models for pathologies such as cardiovascular disease and ocular diseases are well-known in the art. An effective dose for preventing or reducing the severity of a disease is a dose that results in either partial or complete alleviation of at least one symptom of the disease. The appropriate dose of a compound for treatment of a human subject can be determined by those skilled in the art, and is dependent, for example, on the particular disease being treated, nature and bioactivity of the particular compound, the desired route of administration, the gender, age and health of the individual, and the number of doses and duration of treatment.

It is understood that modifications which do not substantially affect the activity of the various embodiments of this invention are also included within the definition of the invention provided herein. Accordingly, the following examples are intended to illustrate but not limit the present invention.

EXAMPLE I

Identification of Alternatively Spliced COX-1 Variants

This example describes the molecular cloning of several alternatively spliced COX-1 variants and their expression in cell culture.

Total RNA derived from human heart, brain, lung, spleen, small intestine, skeletal muscle, kidney and liver tissue were purchased from Clontech. Total RNA was isolated from human eyes (NDRI; Philadelphia, Pa.) and human ocular tissues (ciliary smooth muscles, trabecular meshwork, ODM-2) using a Qiagen total RNA isolation kit, according to the manufacturer's instructions. The ODM-2 cell line is derived from human non-pigmented ciliary epithelial cells (Escribano et al., *J. Cell. Physiol.* 160:511–521 (1994)). Using 5 μg of human total RNA, first strand cDNA was synthesized using SuperScript II RNase H reverse transcriptase (Life Technologies; Carlsbad, Calif.). Reactions (20 μl) containing 5 μg of RNA, 250 ng of oligo (dT), and 100 units of reverse transcriptase were incubated at 42° C. for 1 hour and terminated by incubation at 100° C. for 3 minutes. The PCR buffer contained 10 mM Tris-HCl, pH 8.3, 50 mM KCl, 2 mM MgCl, 2.5 units AmpliTaq DNA polymerase, 0.2 μM upstream and downstream primers, in a final volume of 50 μl. After an initial incubation for 5 minutes at 94° C., samples were subjected to 30 cycles of 30 seconds at 95° C., 30 seconds at 58° C., and 30 seconds at 72° C. in a PE 9700 thermal cycler.

The primers used for detection of alternatively spliced COX-1 variants were as follows:

(SEQ ID NO: 11)
Human COX-1 Forward: GGTTCTTGCTGTTCCTGCTC
and (SEQ ID NO: 12)
Human COX-1 Reverse: TCACACTGGTAGCGGTCAAG The PCR products were isolated from a 1.5% lower melting agarose gel, and subcloned into the TOPO PCRII vector (Invitrogen; Carlsbad, Calif.). Nucleotide sequencing of the vectors was performed by Sequetech (Mountain View, Calif.).

Full length cDNAs for COX-1 variants ALT-1 to ALT-4 were isolated and subcloned into TOPO pcDNA3.1 PCR cloning vector (Invitrogen; Carlsbad, Calif.) or pCEP4 expression vector (Invitrogen) to create Alt COX1/pcDNA3.1 plasmids or Alt COX1/pCEP4 plasmids. Alt COX1/pcDNA3.1 plasmids were used for transient transfection, and Alt COX1/pCEP4 plasmids were used for stable transfection. Full length $G\alpha_{16}$ cDNA was subcloned into the pcDNA3.1 vector. The plasmids were sequenced by Sequetech.

Chinese Hamster Ovary (CHO) and COS-7 cells were obtained from the American Type Culture Collection (ATCC). These cells were routinely maintained in DMEM with 10% fetal bovine serum, 1% glutamine, 0.5% penicillin/streptomycin. Cells. were kept in humidified 5% $CO_2$, 95% air at 37° C. For stable transfection, Alt COX1/pCEP4 plasmids were transfected into CHO and COS-7 cells using Fugene 6 (Roche Diagnostics Corp., Inc.; Indianapolis, Ind.), according to the manufacture's instructions, and then 200 mg/ml hygromycin was used to select cell clones that stably expressed the plasmid.

In addition, the COX-1 variants were cloned into the baculovirus expression vector pBlueBac 4.5/V5-His (Invitrogen) to crease Alt COX1/pBlueBac plasmids. Baculovirus expression was performed in Sf9 or Sf21 cells obtained from Invitrogen. Briefly, Sf9 or Sf21 cells were maintained in Grace's insect media and media supplements (TC yeastolate, lactalbumin hydrolysate and L-glutamine) in humidified 5% $CO_2$, 95% air at 25° C. Sf9 or Sf21 cells ($1\times10^6$) were infected with viral stocks at a multiplicity of infection of 3 for expression of COX-1 variants. In stable transfection, tunicamycin was added to a final concentration of 10 mg/ml to insect cells one hour after infection, and cells were cultured and harvested after 48 hours.

EXAMPLE II

Screening Assays Using Alternatively Spliced COX-1 Variants

This example describes assays based on enzyme activity for identifying compounds that modulate alternatively spliced COX-1 variants.

A. Prostaglandin Synthesis Assays

After 48 hours of transfection, HEK 293/EBNA or Sf9 or Sf21 cells are preincubated with a compound for 30 minutes at 25° C. Arachidonic acid (100 μl, final concentrations 5 or 30 μM) is then added for an additional 10 minute incubation at 37° C. Supernatants are assayed for COX activity by radioimmunoassay (RIA) or enzyme immunoassay (Cayman Chemical Inc.) for $PGE_2$ accumulation. Assays are performed multiple times in triplicate. Inhibition curves are constructed and $IC_{50}$ values are determined using KaleidaGraph 3.5.

One example of the $PGE_2$ assay is as follows. Compounds (0.001–100 μM) are preincubated with enzyme for 20 minutes in 50 mM $KPO_4$, pH 7.5, 1 μM heme, 0.01% phenol, 0.3 mM epinephrine. Following a 10 minute incubation of arachidonic acid, $PGE_2$ formed as a function of COX activity is detected by ELISA (Caymen, Ann Arbor, Mich.).

B. N,N,N,N'-tetramethyl-p-phenylenediamine (TMPD) Turnover Assay

Another assay that can be used for screening compounds against alternatively spliced COX-1 variants is a substrate turn-over assay such as a TMPD turn-over assay. Half-maximal inhibition ($IC_{50}$) is determined by measuring the turnover of TMPD in a spectrophotometric assay. Arachidonic acid is used as a hydroperoxide source, along with the peroxidase substrate TMPD as a co-substrate. Compounds are incubated for 1 minute with purified COX-1 or COX-1 variants in 1 mM heme, 0.1 M Tris-HCl, pH 8.1. The reaction is started by addition of 100 mM arachidonic acid, 170 μM TMPD and measured by a change in absorbance at 611 nm. Either the initial rate (linear for approximately 10 seconds) is measured or time points at 1 and 5 minutes are taken. Time-dependent inactivation curves are made by incubating 10 mM compound with enzyme for 5 seconds to 2 minutes. Kits for determining COX-1 activity using the TMPD turn-over assay are commercially available, for example, from Cayman Chemical Inc. (Ann Arbor, Mich.).

Chemiluminesent Assay for COX-1 Peroxidase Activity

A chemiluminescent substrate can be used to detect the peroxidative activity of a COX-1 variant or other COX enzyme. After inhibition by NSAIDs, the direct residual activity of COX is measured by addition of arachidonic acid and a luminescent substrate. Light emission, directly proportional to the COX-1 variant activity in the sample, is measured over 5 seconds.

A sample protocol is as follows:
1. Prepare enzyme dilutions, buffers and Arachidonic Acid Stock Solution.
2. Pipet buffer, hematin and COX-I or COX-II and inhibitor into duplicate tubes or wells and incubate.
3. Simultaneously pipet or inject the Substrate and Acachidonic Acid into the tubes or wells.
4. Immediately read in a suitable luminometer or chemiluminescent detector for 5 seconds.
5. Calculate COX-1 variant or other COX enzyme concentration from the Standard Curve.

Kits for determining COX-1 activity using a chemiluminescent assay for COX-1 peroxidase activity are commercially available, for example, from Assay Designs, Inc. (Ann Arbor, Mich.), Calbiochem (San Diego, Calif.) or Stressgen Biotechnologies (Victoria, British Columbia).

EXAMPLE III

Tissue Distribution of Alternatively Spliced COX-1 Variants

This example shows the tissue distribution of alternatively spliced COX-1 variant ALT-1 to ALT-4 mRNA using RT-PCR.

Human multiple tissue RNA samples were purchased from BD Biosciences (Clontech). Using 5 µg of human total RNA, first strand cDNA was synthesized by SuperScript II Rnase H reverse transcriptase (Life Technologies). Reactions (20 µl) containing 5 µl of RNA, 250 ng of oligo (dT), and 100 units of reverse transcriptase were incubated at 42° C. for 1 hour and terminated by 100° C. for 3 minutes.

PCR reactions contained the following: PCR buffer (10 mM Tris-HCl, pH 8.3, 50 mM KCl, 2 mM MgCl), 2.5 units AmpliTaq DNA polymerase, 0.2 µM forward and reverse primers, in a final volume of 50 µl. After an initial incubation for 5 minutes at 94° C., samples were subjected to 30 cycles of 30 seconds at 95° C., 30 seconds at 58° C., and 30 seconds at 72° C. in a PE 9700 thermal cycler.

Multiple tissue RT-PCR analysis was performed to detect alternatively spliced COX-1 variant mRNA using the following primers, where F stands for forward primer and R stands for reverse primer:

```
ALT-1 F TACATTTAGGAGCCGGGATG (SEQ ID NO: 31)
ALT-1 R TGGTGCTGGCATGGATAGTA (SEQ ID NO: 32)
```

-continued
```
ALT-2 F TACATTTAGGAGCCGGGATG (SEQ ID NO: 33)
ALT-2 R GCATCTGGCAACTGCTTCTT (SEQ ID NO: 34)
ALT-3 F GCCATGGAGTTCAACCATCT (SEQ ID NO: 35)
ALT-3 R ATCTCCCGAGACTCCCTGAT (SEQ ID NO: 36)
ALT-4 F TACATTTAGGAGCCGGGATG (SEQ ID NO: 37)
ALT-4 R TGGTGCTGGCATGGATAGTA (SEQ ID NO: 38)
```

The results of these assays are shown in FIGS. 8 and 9. In particular, COX-1 variant ALT-1 mRNA was expressed in all of the tissue types examined. COX-1 variant ALT-2 was expressed at various levels in the tissues examined, with low to undetectable levels found in skeletal muscle. COX-1 variant ALT-3 also was expressed at various levels in the tissues examined, with low to undetectable levels found in liver, lung, skeletal muscle and heart. In addition, human COX-1 variant ALT-4 mRNA was expressed at various levels in different tissues, with low to undetectable levels found in liver, brain, small intestine, skeletal muscle and heart. In addition, COX-1 variant ALT-4 mRNA was present in low to undetectable levels in the neuronal cell line SK-N-SH, but was induced by 20% fetal bovine serum treatment of these cells (see FIGS. 9 and 10).

EXAMPLE IV

Induction of COX-1 Variant ALT-4 in Response to Fetal Bovine Serum

This example shows alternatively spliced COX-1 variant ALT-4 mRNA is induced in SK-N-SH cells in response to treatment with 20% fetal bovine serum (FBS).

The neuronal cell line SK-N-SH was used in the following experiment. SK-N-SH cells were treated with 20% FBS for 3 hours. At 1, 3, 6, and 24 hours post-treatment with cell culture media containing 20% FBS, cells were harvested and total RNA was isolated using the Qiagen total RNA Isolation kit. RT-PCR was then performed using the procedure and primers disclosed above for COX-1 variants ALT-1 and ALT-4.

As shown in FIG. 10, induction of COX-1 variant ALT-4 mRNA in SK-N-SH cells was observed by as three hours post induction.

All journal article, reference and patent citations provided herein, including referenced sequence accession numbers of nucleotide and amino acid sequences contained in various databases, in parentheses or otherwise, whether previously stated or not, are incorporated herein by reference in their entirety.

Although the invention has been described with reference to the disclosed embodiments, those skilled in the art will readily appreciate that the specific experiments detailed are only illustrative of the invention. It should be understood that various modifications can be made without departing from the spirit of the invention.

What is claimed is:

1. An isolated nucleic acid molecule, comprising a nucleotide sequence that encodes the amino acid sequence of SEQ ID NO: 2.

2. A vector, comprising the isolated nucleic acid molecule of claim 1.

3. An isolated host cell, comprising the vector of claim 2.

* * * * *